United States Patent
Kawano et al.

(10) Patent No.: US 8,192,346 B2
(45) Date of Patent: Jun. 5, 2012

(54) HOUSING APPARATUS

(75) Inventors: Hironao Kawano, Hino (JP); Hironobu Takizawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1013 days.

(21) Appl. No.: 12/163,189

(22) Filed: Jun. 27, 2008

(65) Prior Publication Data

US 2008/0297291 A1    Dec. 4, 2008

Related U.S. Application Data

(63) Continuation of application No. PCT/JP2006/326138, filed on Dec. 27, 2006.

(30) Foreign Application Priority Data

Dec. 28, 2005  (JP) ................... 2005-380456

(51) Int. Cl.
    *A61N 2/00*    (2006.01)
(52) U.S. Cl. ........................... 600/9
(58) Field of Classification Search ............... 600/9–15; 128/897–898
    See application file for complete search history.

(56) References Cited

U.S. PATENT DOCUMENTS

| | | |
|---|---|---|
| 2003/0018280 A1 | 1/2003 | Lewkowicz et al. |
| 2005/0124875 A1 | 6/2005 | Kawano et al. |

FOREIGN PATENT DOCUMENTS

| | | |
|---|---|---|
| EP | 1 057 539 A1 | 12/2000 |
| JP | 2003-325682 | 11/2003 |
| JP | 2004-017022 | 1/2004 |
| JP | 2004-255174 | 9/2004 |
| JP | 2004-529718 | 9/2004 |
| JP | 2005-285857 | 10/2005 |
| WO | WO 2005/032370 A1 | 4/2005 |

OTHER PUBLICATIONS

European Supplementary Search Report dated Aug. 31, 2011 from corresponding European Patent Application No. 06 84 3520.5.

*Primary Examiner* — John Lacyk

(74) *Attorney, Agent, or Firm* — Scully, Scott, Murphy & Presser, P.C.

(57) ABSTRACT

A housing apparatus includes housing units in which a plurality of permanent magnets are housed, respectively; binding units which are arranged in the housing units, respectively, and bind the permanent magnets in the housing units, respectively; permanent magnet detectors which are arranged in the housing units, respectively, and detect whether the permanent magnets are housed in the housing units, respectively; and a control unit which controls the binding units to selectively keep the permanent magnets in a binding state or a nonbinding state on the basis of detection results of the permanent magnet detectors.

18 Claims, 36 Drawing Sheets

HOUSING APPARATUS

CROSS-REFERENCE TO RELATED APPLICATIONS

This application is a continuation of PCT international application Ser. No. PCT/JP2006/326138 filed Dec. 27, 2006 which designates the United States, incorporated herein by reference, and which claims the benefit of priority from Japanese Patent Application No. 2005-380456, filed Dec. 28, 2005, incorporated herein by reference.

BACKGROUND OF THE INVENTION

1. Field of the Invention

The present invention relates to a housing apparatus which houses a magnet to guide a body-insertable apparatus which is inserted into a subject to pick up an image in the subject.

2. Description of the Related Art

In recent years, in the field of an endoscope, a capsule body-insertable apparatus (for example, a capsule endoscope) in which an imaging function and a radio communication function are set is proposed, and a body-insertable apparatus system which acquires an image in a subject by using the capsule endoscope is developed. In order to observe (examine) the inside of the subject, for example, the capsule endoscope is swallowed from the mouth of the subject. Thereafter, until the capsule endoscope is naturally discharged, the capsule endoscope is moved by peristaltic motion in a body cavity, for example, in an internal organ such as a stomach or a small intestine, and the capsule endoscope functions to pick up an image in the subject at, for example, 0.5-sec intervals.

While the capsule endoscope moves in the subject, images picked by the capsule endoscope are received by an external image display apparatus through an antenna arranged on the body surface of the subject. The image display apparatus has a radio communication function to the capsule endoscope and a memory function for images, and the images received from the capsule endoscope in the subject are sequentially stored in a memory. A doctor or a nurse displays images accumulated in the image display apparatus, i.e., images of the inside of the gastrointestinal tract of the subject on a display to make it possible to observe (examine) the inside of the subject and to give a diagnosis.

As the body-insertable apparatus system, for example, a medical apparatus guidance system which spirally forms a projecting member on an outer surface of a casing and inserts a capsule endoscope having a magnet fixed to the inside of the casing into a subject, forms a rotating magnetic field for the capsule endoscope from the outside of the subject, and controls the rotating magnetic field to guide the capsule endoscope to a desired portion in the subject is known. In the medical apparatus guidance system, the position and direction of the capsule endoscope inserted into the subject are changed by the rotating magnetic field applied from the outside of the subject (see Japanese Unexamined Patent Publication No. 2004-255174).

When a permanent magnet is used as a means that guides the capsule endoscope, the body-insertable apparatus system which guides the capsule endoscope can be realized with a simple configuration. In this case, the permanent magnet is brought close, from the outside of a subject, to the capsule endoscope inserted into the subject, and the posture and the position of the capsule endoscope in the subject can be changed by an operation of a magnetic field generated by the permanent magnet. The permanent magnet to be brought close (i.e., a magnetic field is generated for the capsule endoscope) to the capsule endoscope in the subject is selected from a plurality of permanent magnets having different magnetisms.

A doctor sequentially displays a series of images picked throughout a desired region in a gastrointestinal tract serving as an observed region on a display to observe the inside of a desired gastrointestinal tract of a subject. In this case, the doctor must guide the capsule endoscope inserted into the gastrointestinal tract to change an imaging field of view in the gastrointestinal tract and cause the capsule endoscope to pick up images throughout a desired region in the gastrointestinal tract.

SUMMARY OF THE INVENTION

A housing apparatus according to an aspect of the present invention includes a plurality of housing units in which a plurality of permanent magnets are housed, respectively; a plurality of binding units which are arranged in the plurality of housing units, respectively, and bind the plurality of permanent magnets in the plurality of housing units, respectively; a plurality of permanent magnet detectors which are arranged in the plurality of housing units, respectively, and detect whether the plurality of permanent magnets are housed in the plurality of housing units, respectively; and a control unit which controls the plurality of binding units to selectively keep the plurality of permanent magnets in a binding state or a nonbinding state on the basis of detection results of the plurality of permanent magnet detectors.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferable embodiments of a body-insertable apparatus system and a permanent magnet housing apparatus according to the invention will be described in detail. The invention is not limited to the embodiment.

Figure 1:
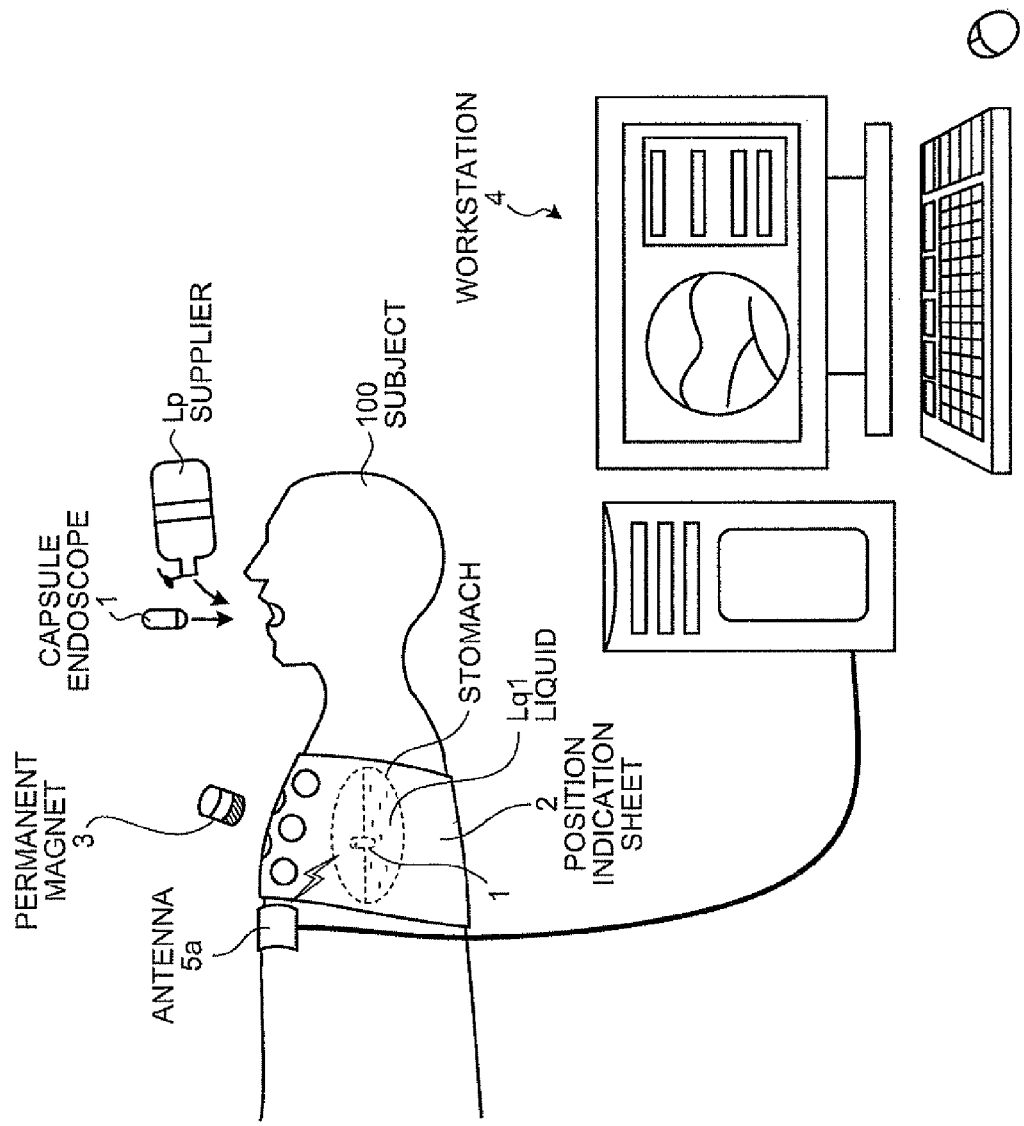
FIG. 1 is a schematic diagram typically showing one configuration of a body-insertable apparatus system according to a first embodiment of the invention.

FIG. 1 is a schematic diagram typically showing one configuration of a body-insertable apparatus system according to a first embodiment of the invention. As shown in FIG. 1, a body-insertable apparatus system according to the first embodiment has a capsule endoscope 1 which is inserted into a subject 100 and picks up an image of an inside of a gastrointestinal tract of the subject 100, a supplier Lp which inserts a liquid Lq1 which floats the capsule endoscope 1 into the subject 100, a permanent magnet 3 to control at least one of a position and an posture of the capsule endoscope 1 floated in the liquid Lq1, a position indication sheet 2 which represents a position on a body surface where the permanent magnet 3 is brought close to the subject 100, and a workstation 4 which displays an image picked by the capsule endoscope 1 on a display.

The capsule endoscope 1 has an imaging function of imaging the inside of the subject 100 and a radio communication function of transmitting various pieces of information of the picked images or the like to the workstation 4. The capsule endoscope 1 is formed to have such a size that the capsule endoscope 1 can be easily inserted into the subject 100 and has a specific gravity which is equal to or less than the liquid Lq1. When the capsule endoscope 1 is swallowed by the subject 100, the capsule endoscope 1 moves in a gastrointestinal tract by peristaltic motion or the like of the subject 100 and sequentially picks images in the gastrointestinal tract at predetermined intervals, for example 0.5-second intervals. The capsule endoscope 1 transmits the picked images of the inside of the gastrointestinal tract to the workstation 4.

The supplier Lp is for supplying the liquid Lq1 which floats the capsule endoscope 1 into the subject 100. More specifically, the supplier Lp contains a desired liquid Lq1 such as water or a normal saline solution and supplies the liquid Lq1 from the mouse of the subject 100 into the body. The liquid Lq1 supplied by the supplier Lp is inserted into the stomach or the like of the subject 100 to float the capsule endoscope 1 in the subject 100.

The permanent magnet 3 functions as a magnetic generator which changes at least one of the position and the posture of the capsule endoscope 1 in the subject 100. More specifically, the permanent magnet 3 generates a magnetic field to the capsule endoscope 1 inserted into the inside (for example, the inside of the stomach) of the subject 100 and controls an operation (i.e., motion of the casing) of the capsule endoscope 1 in the liquid Lq1 by the magnetism of the magnetic field. The permanent magnet 3 controls the operation of the capsule endoscope 1 to control at least one of the position and the posture of the capsule endoscope 1 in the subject 100 and changes at least one of the position and the posture of the capsule endoscope 1. In this case, the capsule endoscope 1 incorporates a magnet which moves the casing in response to the magnetism applied by the permanent magnet 3.

As the permanent magnet 3, a single magnet having a predetermined magnetism may be used. However, it is possible that a plurality of permanent magnets having different magnetisms are prepared, and a permanent magnet selected from the plurality of permanent magnets is used. In this case, as the permanent magnet 3, a permanent magnet which generates an appropriate magnetic field may be selected depending on a body shape (for example, a height, a weight, a waistline, or the like) or an operation (for example, movement, oscillation, or both the operations) of the capsule endoscope 1 to be controlled.

The position indication sheet 2 functions as a position display unit which shows a position (to be referred to as a proximity position hereinafter) where the permanent magnet 3 is brought close to the subject 100 to an examiner such as a doctor or a nurse. More specifically, when the position indication sheet 2 is attached to the subject 100, the position indication sheet 2 shows the proximity position of the permanent magnet 3 on the body surface of the subject 100 to the examiner. The permanent magnet 3 brought close to the proximity position generates a magnetic field to the capsule endoscope 1 in the gastrointestinal tract, and can control at least one of the position and the posture of the capsule endoscope 1 by the magnetism. More specifically, when the examiner changes at least one of the position and the posture of the capsule endoscope 1 in the subject 100 by using the permanent magnet 3, the permanent magnet 3 is brought close to the proximity position indicated by the position indication sheet 2 to control the operation of the capsule endoscope 1 in the subject 100. The operation of the permanent magnet 3 which changes at least one of the position and the posture of the capsule endoscope 1 in the subject 100 will be described later.

The workstation 4 has a radio communication function of receiving various pieces of information of images or the like picked by the capsule endoscope 1 and a display function of displaying the images or the like received from the capsule endoscope 1 on a display. More specifically, the workstation 4 has an antenna 5a which transmits and receives a radio signal to/from the capsule endoscope 1, and, for example, acquires various pieces of information from the capsule endoscope 1 through the antenna 5a arranged on the body surface of the subject 100. In this case, the workstation 4 functions as an image display apparatus which displays the image of the inside of the subject 100 picked by the capsule endoscope 1 on the display. The workstation 4 can transmit a control signal (for example, a control signal to control the start or stop of the imaging operation of the capsule endoscope 1) to control drive control of the capsule endoscope 1 through the antenna 5a.

The antenna 5a is realized by using, for example, a loop antenna and can transmit and receive a radio signal between the capsule endoscope 1 and the workstation 4. More specifically, the antenna 5a, as illustrated in FIG. 1, is arranged at a predetermined position of the body surface of the subject 100, for example at a position near the stomach of the subject 100. In this case, the antenna 5a makes it possible to perform radio communication between the capsule endoscope 1 inserted into the stomach of the subject 100 and the workstation 4. The antenna 5a may be arranged on the body surface of the subject 100 corresponding to a path of the capsule endoscope 1 in the subject 100. The number of antennas 5a as described above is not limited to one, and a plurality of antennas 5a may be used.

Figure 2:
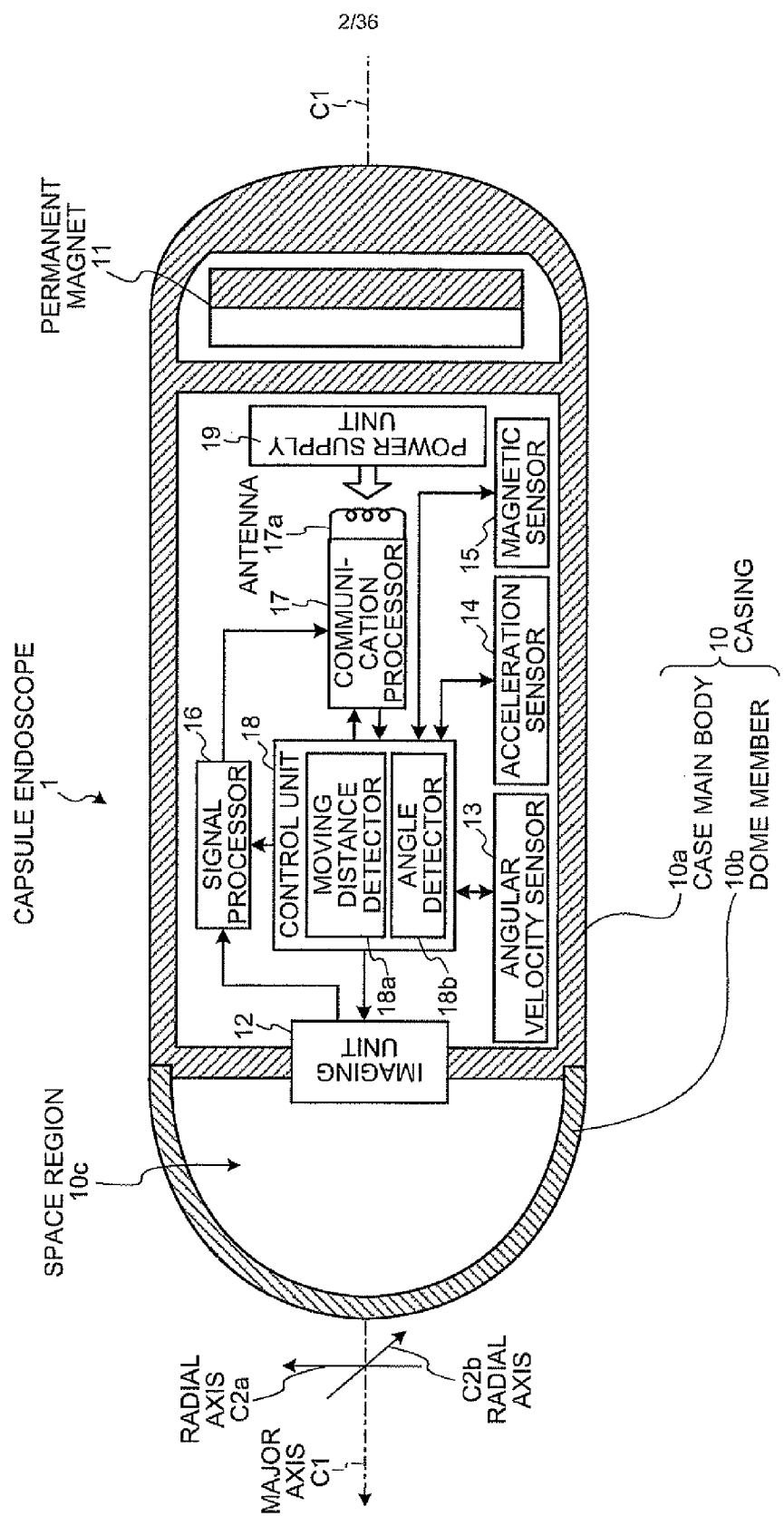
FIG. 2 is a schematic diagram typically showing one configuration of a capsule endoscope according to the first embodiment.

A configuration of the capsule endoscope 1 serving as one example of the body-insertable apparatus system according to the embodiment will be described below. FIG. 2 is a schematic diagram showing one configuration of the capsule endoscope 1. As shown in FIG. 2, the capsule endoscope 1 has a capsule casing 10 formed to have such a size that the capsule casing 10 can be easily inserted into the subject 100 and a permanent magnet 11 which operates the casing 10 by a magnetism of the permanent magnet 3. The capsule endoscope 1 has an imaging unit 12 to image the inside of the subject 100, an angular velocity sensor 13 which detects an angular velocity obtained when the capsule casing 10 is oscillated, an acceleration sensor 14 which detects an acceleration obtained when the casing 10 moves, and a magnetic sensor 15 to detect a strength of a magnetic field applied to the capsule endoscope 1. Furthermore, the capsule endoscope 1 has a signal processor 16 which generates an image signal corresponding to an image picked by the imaging unit 12, an antenna 17a which transmits and receives a radio signal to/from the antenna 5a, and a communication processor 17 which modulates various signals such as image signals transmitted to the external workstation 4 into radio signals or demodulates the radio signal received through the antenna 17a. The capsule endoscope 1 has a control unit 18 which controls drive of the respective components of the capsule endoscope 1 and a power supply unit 19 which supplies a drive force to the respective components of the capsule endoscope 1.

The casing 10 is a capsule member formed to have such a size that the member can be easily inserted into the subject 100, and is realized by a case main body 10a which incorporates the respective components of the capsule endoscope 1 and a dome member 10b which forms a front-end portion of the casing 10. The case main body 10a, for example, as shown in FIG. 2, has the permanent magnet 11 and the power supply unit 19 on a rear-end side relative to the center of the casing 10 and has the imaging unit 12 on the front-end portion. The dome member 10b is a substantially transparent having optical transparency, and is fixed to the front-end portion of the case main body 10a to cover the imaging unit 12. In this case, the dome member 10b forms a space region 10c surrounded by the inner wall of the dome member 10b and the front-end portion of the case main body 10a. The casing 10 formed by the case main body 10a and the dome member 10b has a specific gravity which is almost equal to or less than that of the liquid Lq1 and a center of gravity on the rear-end side.

The permanent magnet 11 is for operating the casing 10 by the magnetism of an externally generated magnetic field. More specifically, when the permanent magnet 11 is magnetized in the longitudinal direction of the casing 10, for example, when the external permanent magnet 3 generates a magnetic field to the permanent magnet 11, the permanent magnet 11 moves or oscillates the casing 10 in the liquid Lq1 on the basis of a magnetism applied by the magnetic field. Accordingly, the permanent magnet 11 can change at least one of the posture and the position of the capsule endoscope 1 in the liquid Lq1 by the magnetism.

The posture of the capsule endoscope 1 mentioned here is the posture of the casing 10 in a predetermined spatial coordinate system xyz. More specifically, when a major axis C1 in a direction extending from the rear-end portion to the front-end portion is set as an axial vector on a central axis along the longitudinal direction of the casing 10, the posture of the capsule endoscope 1 is determined by the direction of the major axis C1 in the spatial coordinate system xyz. The position (mentioned here) of the capsule endoscope 1 is determined by position coordinates of the casing 10 in the spatial coordinate system xyz. More specifically, when the capsule endoscope 1 is inserted into the subject 100, the posture of the capsule endoscope 1 in the subject 100 is determined by the direction of the major axis C1 in the spatial coordinate system xyz, and the position of the capsule endoscope 1 in the subject 100 is determined by the position coordinates of the casing 10 in the spatial coordinate system xyz.

The imaging unit 12 is for picking an image of the inside of a gastrointestinal tract of the subject 100. More specifically, the imaging unit 12 is realized by an imaging device such as a CCD or a CMOS, a light-emitting element such as an LED which illuminates an imaging field of view of the imaging device, and an optical system such as a lens which focuses a reflected beam from the imaging field of view on the imaging device. The imaging unit 12 is fixed to the front-end portion of the case main body 10a as described above, focuses a reflected beam from an imaging field of view received through the dome member 10b, and picks an image of the inside of a gastrointestinal tract of the subject 100. The imaging unit 12 transmits obtained image information to the signal processor 16. The optical system of the imaging unit 12 desirably has a wide angle. In this manner, the imaging unit 12 has a field angle of, for example, about 100° to 140° and can widen the imaging field of view. The body-insertable apparatus system according to the first embodiment of the present invention uses the capsule endoscope 1 having the wide imaging field of view to make it possible to improve observability.

A direction of the imaging field of view of the imaging unit 12 fixed and arranged inside the casing 10 is determined by the direction of the casing 10 in the spatial coordinate system xyz. More specifically, a light-receiving surface of the imaging unit 12 is arranged perpendicularly to a predetermined direction related to the casing 10, for example, the major axis C1. In this case, a central axis (i.e., optical axis) of the imaging field of view of the imaging unit 12 almost coincides with the major axis C1, and the light-receiving surface of the imaging unit 12 is parallel to two radial axes C2a and C2b serving as axial vectors perpendicular to the major axis C1. The radial axes C2a and C2b are axial vectors in the radial direction of the casing 10, and the major axis C1 and the radial axes C2a and C2b are orthogonal to each other. In the imaging unit 12, a normal direction of the light-receiving surface, i.e., the direction of the imaging field of view is determined by the direction of the major axis C1 in the spatial coordinate system xyz, and a rotating angle of the light-receiving surface, i.e., the rotating angle of the imaging field of view having the major axis C1 as a center of rotation is determined by a rotating angle of the radial axis C2a having the major axis C1 as a center of rotation.

The angular velocity sensor 13 is for detecting an angular velocity of the casing 10 when the posture of the capsule endoscope 1 changes. More specifically, the angular velocity sensor 13 is realized by using a MEMS gyro or the like and detects an angular velocity at which the casing 10 oscillates, i.e., the angular velocity of the major axis C1 the direction of which changes in the spatial coordinate system xyz. The angular velocity sensor 13 detects an angular velocity of the casing 10 when the casing 10 rotates about the major axis C1. In this case, the angular velocity sensor 13 detects an angular velocity of the radial axis C2a rotating about the major axis C1. The angular velocity sensor 13 transmits detection results of the angular velocity to the control unit 18.

The acceleration sensor 14 is for detecting an acceleration of the casing 10 when the capsule endoscope 1 displaces. More specifically, the acceleration sensor 14 detects an acceleration at which the casing 10 moves, i.e., an acceleration of the casing 10 the position coordinates of which change in the spatial coordinate system xyz. In this case, the acceleration sensor 14 detects a magnitude and a direction of the acceleration of the casing 10. The acceleration sensor 14 transmits a detection result of the acceleration to the control unit 18.

The magnetic sensor 15 is for detecting a strength of an external magnetic field acting on the capsule endoscope 1. More specifically, when the external permanent magnet 3 generates a magnetic field to the capsule endoscope 1, the magnetic sensor 15 detects a strength of a magnetic field applied to the capsule endoscope 1 by the permanent magnet 3. The magnetic sensor 15 transmits a detection result of the magnetic field strength to the control unit 18.

The signal processor 16 is to generate an image signal corresponding to an image picked by the imaging unit 12. More specifically, the signal processor 16 generates an image signal including image information received from the imaging unit 12. Furthermore, the signal processor 16 includes motion information (will be described later) of the casing 10 received from the control unit 18 in a blanking period of an image signal. In this manner, the signal processor 16 associates an image picked by the imaging unit 12 with the motion information of the casing 10 at the time of imaging. The signal processor 16 transmits the image signal including the image information and the motion information to the communication processor 17.

The communication processor 17 performs a predetermined modulating process or the like to the image signal received from the signal processor 16 to modulate the image signal into a radio signal. Almost similarly, the communication processor 17 modulates a magnetic field detection signal (will be described later) received from the control unit 18 into a radio signal. The communication processor 17 outputs the radio signal generated as described above to the antenna 17a. The antenna 17a is, for example, a coil antenna and transmits the radio signal received from the communication processor 17 to, for example, the external antenna 5a. In this case, the radio signal is received by the workstation 4 through the antenna 5a. On the other hand, the communication processor 17 receives a radio signal from, for example, the workstation 4 through the antenna 17a. In this case, the communication processor 17 performs a predetermined demodulating process or the like to the radio signal received through the antenna 17a, and demodulates the radio signal into a control signal from, for example, the workstation 4. Thereafter, the communication processor 17 transmits the obtained control signal and the like to the control unit 18.

The control unit 18 controls the drives of the imaging unit 12, the angular velocity sensor 13, the acceleration sensor 14, the magnetic sensor 15, the signal processor 16, and the communication processor 17 and performs input/output control of signals in the components. In this case, the control unit 18 controls operation timings of the imaging unit 12, the angular velocity sensor 13, and the acceleration sensor 14 such that the angular velocity and the acceleration of the casing 10 when the imaging unit 12 picks an image are detected. When the control unit 138 receives the control signal from the workstation 4 from the communication processor 17, the drives of the imaging unit 12 is started or stopped on the basis of the control signal. In this case, the control unit 18 controls the drive of the imaging unit 12 on the basis of the control signal of the start of the imaging operation to pick images of the inside of the subject 100 at predetermined intervals, for example, 0.5-second intervals and stops the drive of the imaging unit 12 on the basis of a control signal of the stop of the imaging operation. Furthermore, the control unit 18 recognizes the strength of an external magnetic field on the basis of a detection result received from the magnetic sensor 15 and transmits a magnetic field detection signal corresponding to the magnetic strength to the communication processor 17.

The control unit 18 may control the drive of the imaging unit 12 on the basis of the control signal from the workstation 4 as described above or may start drive control of the imaging unit 12 a predetermined period of time after a drive power is supplied by the power supply unit 19.

The control unit 18 has a moving distance detector 18a which detects a moving distance of the casing 10 when the capsule endoscope 1 is displaced and an angle detector 18b which detects a rotating angle of the casing 10 when the posture of the capsule endoscope 1 changes. The moving distance detector 18a performs a predetermined integration process to an acceleration detected by the acceleration sensor 14 to calculate a moving distance of the casing 10 in the spatial coordinate system xyz. The moving distance calculated by the moving distance detector 18a is a vector quantity representing a moving distance and a moving direction of the casing 10 in the spatial coordinate system xyz. On the other hand, the angle detector 18b performs a predetermined integration process to the angular velocity detected by the angular velocity sensor 13 to calculate a rotating angle of the major axis C1 and a rotating angle of the radial axis C2a in the spatial coordinate system xyz. The control unit 18 transmits the moving distance detected by the moving distance detector 18a and the rotating angles detected by the angle detector 18b to the signal processor 16 as motion information of the casing 10.

Figure 3:
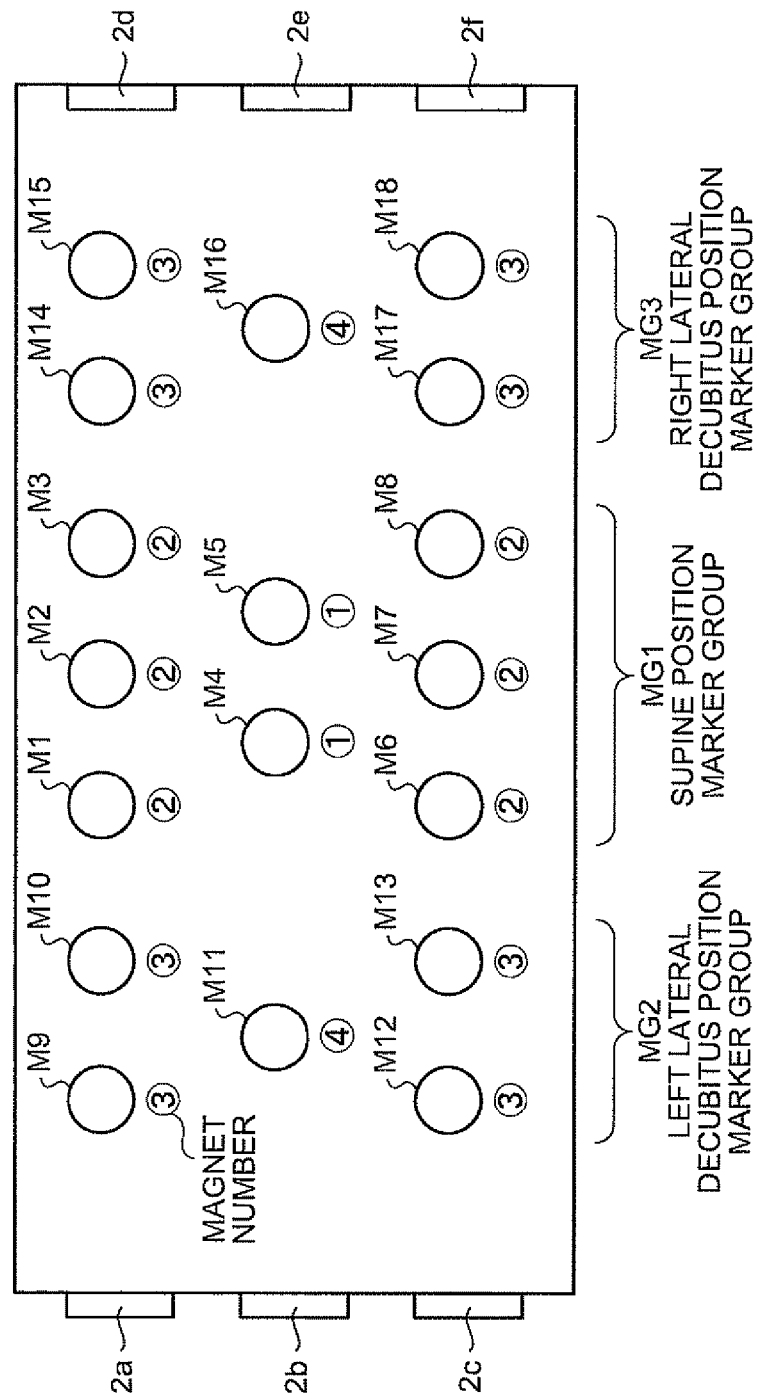
FIG. 3 is a schematic diagram typically showing one configuration of a position indication sheet according to the first embodiment.

The details of the position indication sheet 2 of the body-insertable apparatus system according to the first embodiment of the present invention will be described below. FIG. 3 is a schematic diagram typically showing one configuration of the position indication sheet 2. As shown in FIG. 3, the position indication sheet 2 is a sheet-like member on which a plurality of markers are formed to show the proximity position to an examiner. More specifically, the position indication sheet 2 is a sheet member which consists of cloth, paper, a resin, or the like and can be freely curved. For example, as shown in FIG. 3, a plurality of markers M1 to M18 representing the proximity positions are formed. The number of proximity positions indicated by the position indication sheet 2 is not limited to 18, and at least one proximity position may be used.

The markers M1 to M18 are for showing a proximity position on a body surface where the permanent magnet 3 is brought close to the subject 100 to an examiner. More specifically, the markers M1 to M18 are formed to have desired shapes such as circular forms. When the position indication sheet 2 is attached to the subject 100, the position indication sheet 2 shows proximity positions on the body surface of the subject 100. The markers M1 to M18 are grouped depending on body positions of the subject 100 such as a supine position and indicate different proximity positions depending on the body positions of the subject 100. In this case, the markers M1 to M18 are divided into three groups, for example, a supine position marker group MG1, a left lateral decubitus position marker group MG2, and a right lateral decubitus position marker group MG3.

The supine position marker group MG1 indicates a proximity position when the permanent magnet 3 is brought close to the subject 100 the body position of which is a supine position. The supine position marker group MG1 includes the markers M1 to M8. The left lateral decubitus position marker group MG2 indicates a proximity position when the permanent magnet 3 is brought close to the subject 100 the body position of which is a left lateral decubitus position. The left lateral decubitus position marker group MG2 includes, for example, the markers M9 to M13. The right lateral decubitus position marker group MG3 indicates a proximity position when the permanent magnet 3 is brought close to the subject 100 the body position of which is a right lateral decubitus position. The right lateral decubitus position marker group MG3 includes, for example, the markers M14 to M18. An examiner brings the permanent magnet 3 close to all the proximity positions indicated by the markers M1 to M18 once to change at least one of the position and the posture of the capsule endoscope 1 in the liquid Lq1 inserted into a desired gastrointestinal tract (for example, a stomach or the like) in the subject 100, thereby changing an imaging field of view over the nearly entire region in the gastrointestinal tract. The examiner can cause the capsule endoscope 1 to pick a series of images over the nearly entire region in the gastrointestinal tract.

On the position indication sheet 2, for example, as shown in FIG. 3, magnet numbers are added to positions near the markers M1 to M18, respectively. The magnet numbers are for specifying the plurality of permanent magnets, respectively, and are examples of pieces of selection information for selecting the permanent magnet 3 brought close to the subject 100 from the plurality of permanent magnets. More specifically, when the examiner brings the permanent magnet 3 close to a proximity position indicated by any one of the markers M1 to M18, the permanent magnet specified by the magnetic number added to the position near the marker of the proximity position is selected from the plurality of permanent magnets. For example, when the examiner brings the permanent magnet close to the proximity position indicated by the marker M9, the examiner selects a permanent magnet specified by magnet number 3 from the plurality of prepared permanent magnets and brings the permanent magnet of magnet number 3 close to the marker M9.

The selection information added to a position near the marker is not limited to the magnet number described above. Information such as a symbol or a diagram of another mode which specifies a permanent magnet may be used, or information representing a strength of a magnetic field to be generated or a magnetism of the magnetic field may be used. In this case, the examiner may select a permanent magnet having a magnetism or a magnetic field strength indicated by the selection information from the plurality of permanent magnets. As the selection information, the shapes of the illustrated markers are changed depending on the permanent magnets, the markers themselves indicate proximity positions, and pieces of selection information of permanent magnets brought close to the proximity positions may be indicated by shapes.

Figure 4:
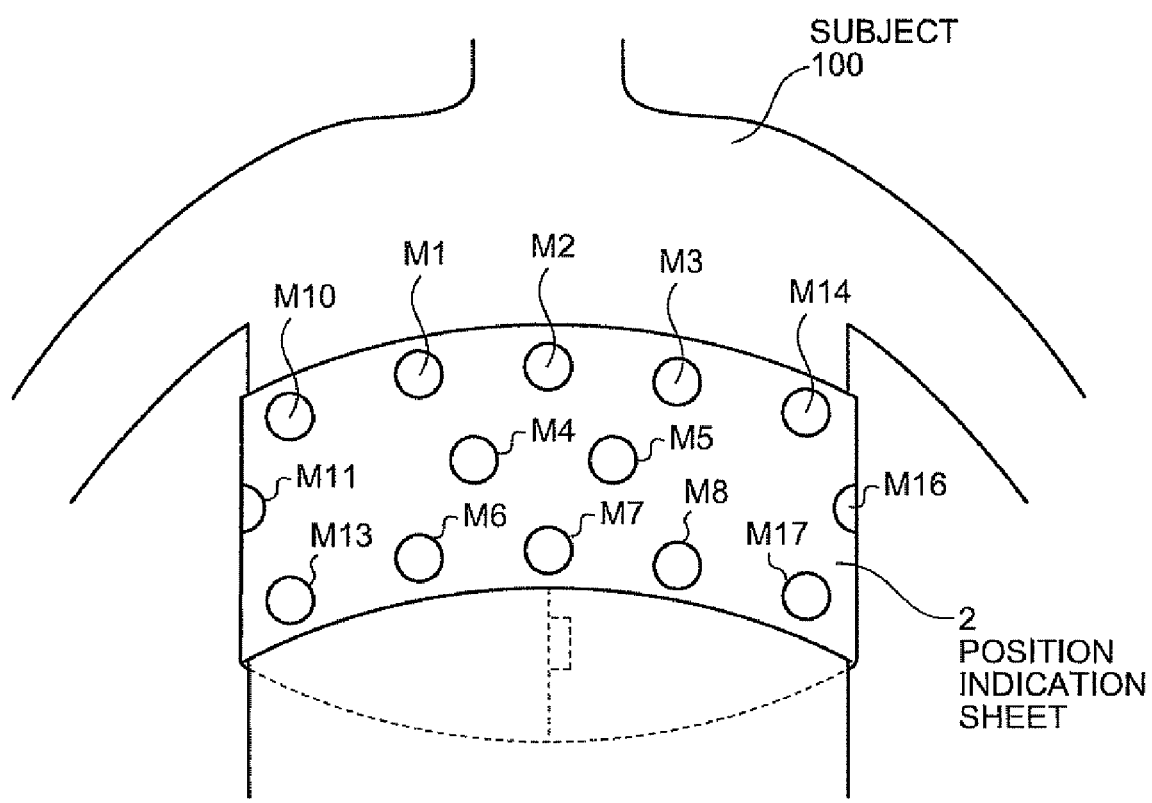
FIG. 4 is a schematic diagram illustrating a state in which a position indication sheet is attached to a subject.

On the other hand, on the position indication sheet 2, projecting portions 2a to 2c and fitting portions 2d to 2f are arranged near both opposing ends. The projecting portions 2a to 2c and the fitting portions 2d to 2f form one pair of connection portions for connecting both the ends of the position indication sheet 2. More specifically, the projecting portion 2a and the fitting portion 2d form one pair of connection portions, the projecting portion 2b and the fitting portion 2e form one pair of connection portions, and the projecting portion 2c and the fitting portion 2f form one pair of connection portions. In this case, the projecting portions 2a to 2c are fitted in the fitting portions 2d to 2f, respectively, so that the position indication sheet 2 connects both the opposing end portions and forms a cylindrical shape. the position indication sheet 2, for example, as shown in FIG. 4, is wound on the trunk of the subject 100, and the projecting portions 2a to 2c and the fitting portions 2d to 2f are connected, respectively to be attached to the subject 100. In this manner, the position indication sheet 2 attached to the subject 100 shows the examiner a proximity position of the permanent magnet 3 for the subject 100 to the examiner by causing, for example, the markers M1 to M18 to face outside.

Figure 5:
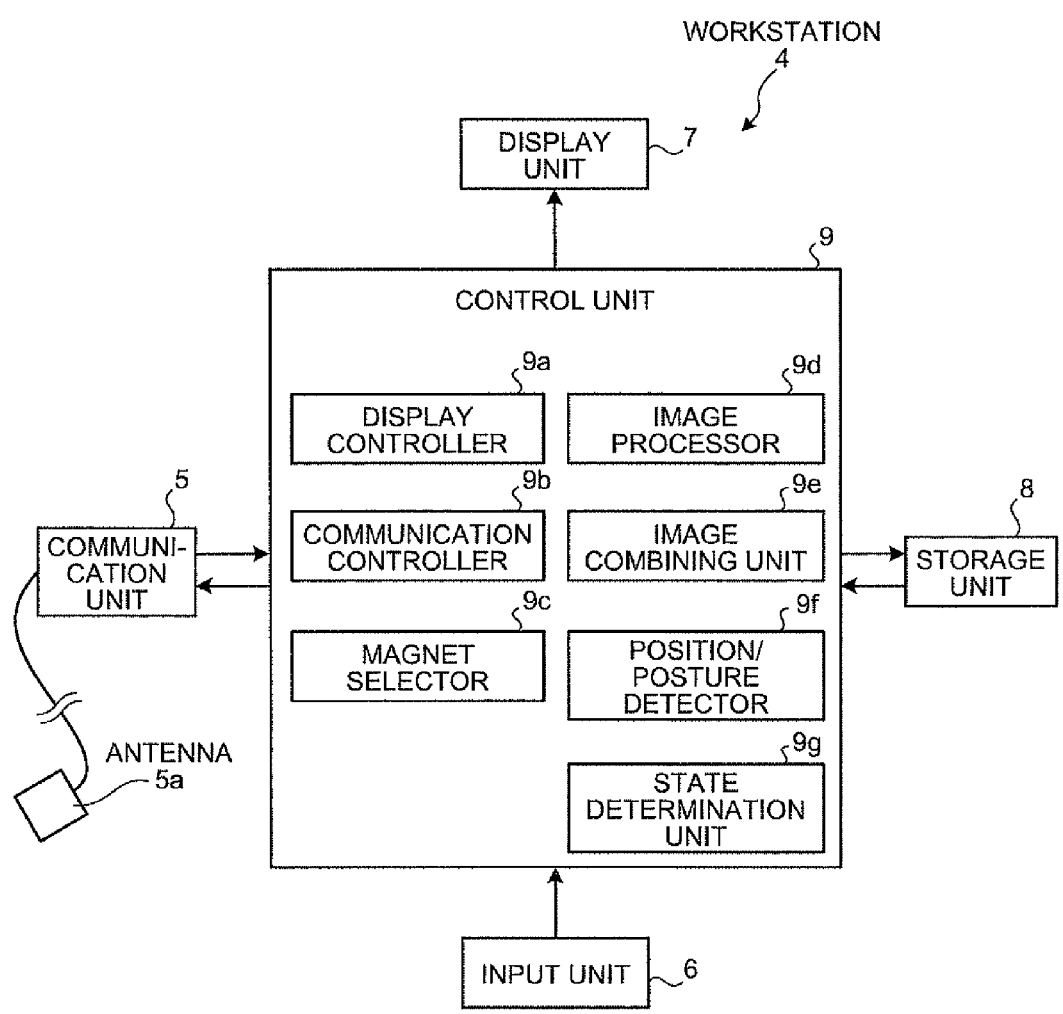
FIG. 5 is a block diagram typically showing one configuration of a workstation according to the first embodiment.

The workstation 4 of the body-insertable apparatus system according to the first embodiment of the present invention will be described below in detail. FIG. 5 is a block diagram typically showing one configuration of the workstation 4. As shown in FIG. 5, the workstation 4 has a communication unit 5 which performs radio communication to the capsule endoscope 1 by using the antenna 5a, an input unit 6 which inputs various pieces of designation information to the workstation 4, a display unit 7 which displays an image or the like picked by the capsule endoscope 1, a storage unit 8 which stores various pieces of information such as pieces of image information, and a control unit 9 which controls drives of components of the workstation 4.

In the communication unit 5, the antenna 5a is connected through a cable, a predetermined demodulating process is performed to a radio signal received through the antenna 5a, and various pieces of information transmitted from the capsule endoscope 1 are acquired. In this case, the communication unit 5 acquires image information obtained by the imaging unit 12 and motion information of the casing 10 and transmits the acquired image information and the acquired motion information to the control unit 9. The communication unit 5 acquires a magnetic field detection signal corresponding to a detection result of a magnetic field strength obtained by the magnetic sensor 15 and transmits the acquired magnetic field detection signal to the control unit 9. On the other hand, the communication unit 5 performs a predetermined modulating process or the like to the control signal to the capsule endoscope 1 received from the control unit 9 to modulate the control signal into a radio signal. In this case, the communication unit 5 transmits the generated radio signal to the antenna 5a, and the radio signal is transmitted to the capsule endoscope 1 through the antenna 5a. In this manner, the communication unit 5 can transmit a control signal which designates drive of, for example, the imaging unit 12 to be started to the capsule endoscope 1.

The input unit 6 is realized by using a keyboard or a mouse, and inputs various pieces of information to the control unit 9 by an input operation by the examiner. In this case, the input unit 6 inputs various pieces of designation information which designates, for example, the control unit 9 or patient information or the like related to the subject 100. As the designation information, for example, designation information for displaying an image acquired from the capsule endoscope 1 on the display unit 7, designation information for processing the image acquired from the capsule endoscope 1, and the like are used. As the patient information, for example, information such as the name (patient name), sex, birth date, patient ID, and the like of the subject 100 for specifying the subject 100 and the bodily information such as the height, weight, and waistline of the subject 100 are used.

The display unit 7 is realized by using a display such as a CRT display or a liquid crystal display and displays various pieces of information displayed and designated by the control unit 9. In this case, the display unit 7 displays various pieces of information required to observe and diagnose the inside of the subject 100 such as images picked by, for example, the capsule endoscope 1 and patient information or the like of the subject 100. The display unit 7 displays the images subjected to predetermined processing by the control unit 9.

The storage unit 8 stores various pieces of information written and designated by the control unit 9. More specifically, the storage unit 8 stores various pieces of information received from, for example, the capsule endoscope 1, various pieces of information input by the input unit 6, image information subjected to the predetermined processing by the control unit 9, and the like. In this case, the storage unit 8 stores the image information and the motion information in association with each other. The storage unit 8 transmits information designated by the control unit 9 to the control unit 9.

The control unit 9 performs drive control of the components of the workstation 4 such as the communication unit 5, the input unit 6, the display unit 7, and the storage unit 8 to perform input/output control of information to the components and an information process to input/output various pieces of information between the components. The control unit 9 outputs various control signals to the capsule endoscope 1 to the communication unit 5 on the basis of the designation information input from the input unit 6. In this case, the control signal to the capsule endoscope 1 is transmitted to the capsule endoscope 1 through the antenna 5a. More specifically, the workstation 4 functions as a control means which controls drive of the capsule endoscope 1.

The control unit 9 has a display controller 9a which controls a display operation of various pieces of information by the display unit 7 and a communication controller 9b which controls drive of the communication unit 5 described above. The control unit 9 has a magnet selector 9c which selects a permanent magnet which generates a sufficient magnetic field to move the capsule endoscope 1 in the liquid Lq1 and an image processor 9d which generates an image of the inside of, for example, the subject 100 on the basis of an image signal received from the capsule endoscope 1. Furthermore, the control unit 9 has an image combining unit 9e which synthesizes common parts of the plurality of images generated by the image processor 9d with each other to combine the plurality of images in, for example, the subject 100, a position/posture detector 9f which detects the position and the posture of the capsule endoscope 1, and a state determination unit 9g which determines whether motion of the capsule endoscope 1 can be controlled by a magnetic field of the permanent magnet 3.

The magnet selector 9c selects a permanent magnet which generates a magnetic field sufficient to move the capsule endoscope 1 in the liquid Lq1 on the basis of a determination result of the state determination unit 9g. In this case, the state determination unit 9g detects a magnetic field strength of the permanent magnet 3 to the capsule endoscope 1 on the basis of the magnetic field detection signal received from the capsule endoscope 1 and performs a comparing process for comparing the detected magnetic field strength with a predetermined magnetic field strength range. The state determination unit 9g determines, on the basis of a result of the comparing process, whether the motion of the capsule endoscope 1 can be controlled by the magnetic field of the permanent magnet 3. More specifically, when the detected magnetic field strength falls within the predetermined magnetic field strength range, the state determination unit 9g determines whether the magnetic field strength of the permanent magnet 3 is sufficient to control the motion of the capsule endoscope 1. When the detected magnetic field strength is lower than the predetermined magnetic field strength range, the state determination unit 9g determines that the magnetic field strength of the permanent magnet 3 is insufficient. When the magnetic field strength is higher than the predetermined magnetic field strength range, the state determination unit 9g determines that the magnetic field strength of the permanent magnet 3 is excessive. The magnet selector 9c selects the permanent magnet the magnetic field strength of which is determined to be sufficient. When the state determination unit 9g determines that the magnetic field strength is insufficient, the magnet selector 9c selects the permanent magnet which generates a magnetic field stronger than that of a present permanent magnet. When the state determination unit 9g determines that the magnetic field strength is excessive, the magnet selector 9c selects a permanent magnet which generates a magnetic field weaker than that of the present permanent magnet. The display controller 9a displays the selection result of the permanent magnet obtained by the magnet selector 9c on the display unit 7. In this case, the examiner visually checks the selection result of the permanent magnet displayed on the display unit 7 to make it possible to easily select a preferable permanent magnet for controlling the motion of the capsule endoscope 1 from the plurality of permanent magnets.

The image processor 9d generates an image picked by the capsule endoscope 1 on the basis of an image signal from the capsule endoscope 1. In this case, the display controller 9a sequentially displays images generated by the image processor 9d on the display unit 7 in chronological order. The image combining unit 9e performs an image combining process of combining a plurality of images generated by the image processor 9d into one image. The display controller 9a displays a processed image (for example, a panoramic image showing the inside of a gastrointestinal tract of the subject 100) combined by the image combining unit 9e on the display unit 7. The image combining process of the image combining unit 9e will be described later.

The position/posture detector 9f detects the position and the posture of the capsule endoscope 1 in the spatial coordinate system xyz on the basis of the motion information received from the capsule endoscope 1. More specifically, the position/posture detector 9f sets the spatial coordinate system xyz for determining the position and the posture of the capsule endoscope 1. In this case, the capsule endoscope 1 is arranged at an original point O of the spatial coordinate system xyz in a mode in which the radial axis C2b, the major axis C1, and the radial axis C2a are matched to the x axis, the y axis, and the z axis of the spatial coordinate system xyz, respectively. The position/posture detector 9f recognizes the position and the posture of the capsule endoscope 1 arranged in the spatial coordinate system xyz as an initial state. The position/posture detector 9f sequentially detects position coordinates (x, y, z) of the capsule endoscope 1 moving or oscillating by using an original point O as an origin and a direction of the major axis C1 (i.e. r sequentially changed from the initial state). In this case, the position/posture detector 9f sequentially acquires a moving distance (vector quantity) of the casing 10, the rotating angle of the major axis C1, and the rotating angle of the radial axis C2a when the capsule endoscope 1 moves or oscillates in the spatial coordinate system xyz on the basis of pieces of motion information sequentially received from the capsule endoscope 1.

On the basis of the moving distances of the casing 10, the rotating angles of the major axis C1, and the rotating angles of the radial axis C2a which are sequentially acquired as described above, the position/posture detector 9f detects a relative position of the casing 10 to the original point O, i.e., the position coordinates (x, y, z) of the casing 10 in the spatial coordinate system xyz and the vector direction of the major axis C1 in the spatial coordinate system xyz. The position coordinates (x, y, z) of the casing 10 and the vector direction of the major axis C1 detected by the position/posture detector 9f correspond to the position and the posture of the capsule endoscope 1 in the spatial coordinate system xyz, respectively.

The position/posture detector 9f detects an inclination of the radial axis C2a with respect to the z axis of the spatial coordinate system xyz on the basis of the rotating angle of the radial axis C2a. In this case, the radial axis C2a is an axial vector which determines an upper direction of a light-receiving surface of the imaging unit 12 and an axial vector which determines an upper direction of the image picked by the imaging unit 12. Therefore, the position/posture detector 9f detects an inclination of the radial axis C2a with respect to the z axis to make it possible to detect an inclination to the z axis of an image (i.e., an image picked by the imaging unit 12) including the major axis C1 as a normal vector.

The control unit 9 stores the position and the posture of the capsule endoscope 1 detected by the position/posture detector 9f and the inclination to the z axis of the image picked by the imaging unit 12 in the storage unit 8 as position/posture information. In this case, the control unit 9 acquires the position/posture information for each image information received by the capsule endoscope 1 and sequentially stores the image information and the position posture information in the storage unit 8 in association with each other.

Figure 6:
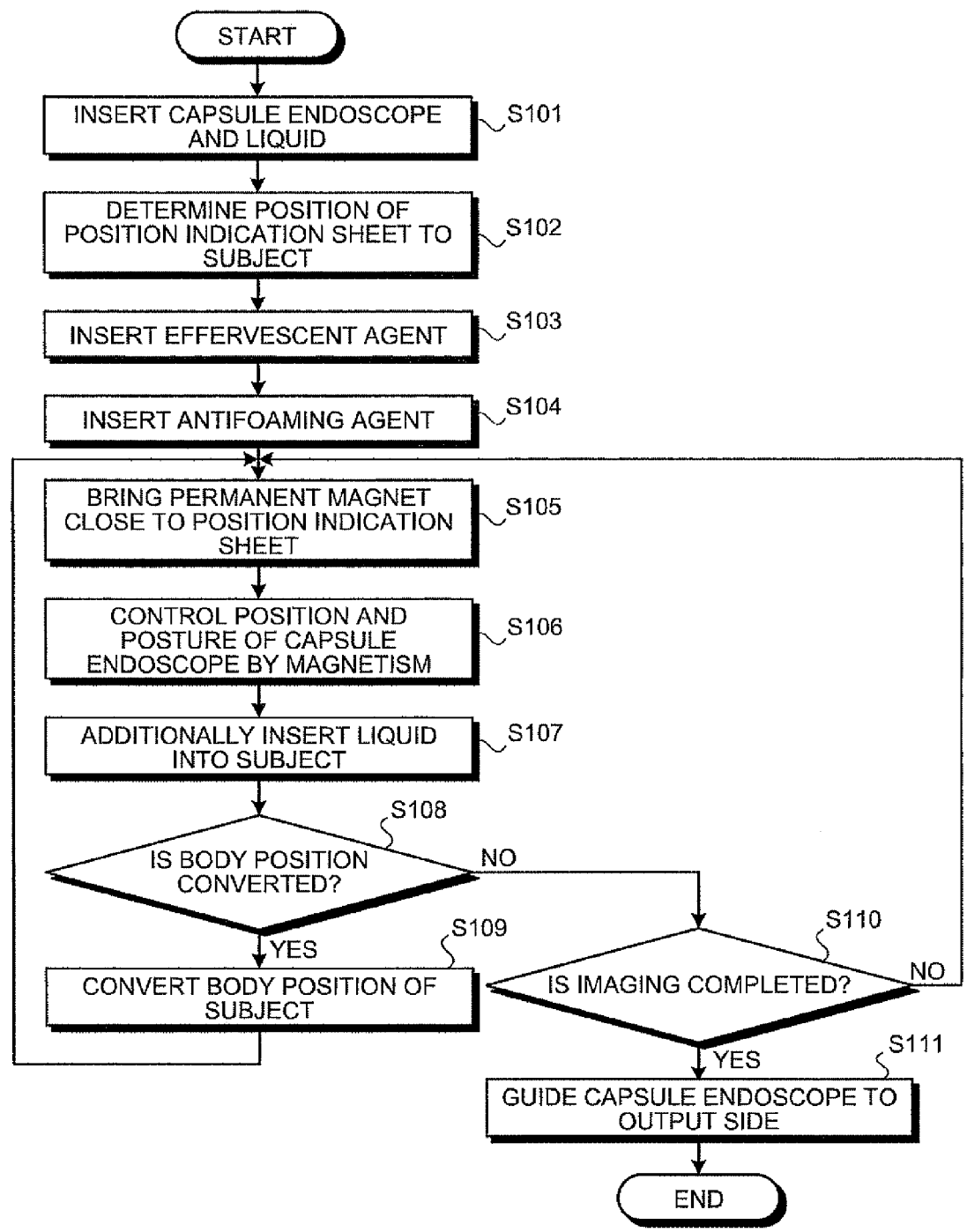
FIG. 6 is a flow chart for explaining a procedure of observing an inside of a gastrointestinal tract of a subject by the body-insertable apparatus system according to the first embodiment.

A procedure of observing an inside (for example, an inside of a stomach) of a gastrointestinal tract of the subject 100 on the basis of an image picked by the capsule endoscope 1 will be described below. FIG. 6 is a flow chart for explaining a procedure of observing an inside of a gastrointestinal tract of the subject 100 on the basis of the image of the inside of the gastrointestinal tract obtained by the capsule endoscope 1 inserted into the subject 100.

In FIG. 6, an examiner starts an imaging operation of the capsule endoscope 1 by using the workstation 4 or a predetermined starter, inserts the capsule endoscope 1 into the subject 100, and inserts the liquid Lq1 into the subject 100 by using the supplier Lp (step S101). The examiner attaches the position indication sheet 2 to the subject 100 to determine a position of the position indication sheet 2 on the subject 100 (step S102). More specifically, when the examiner will observe the inside of the stomach of, for example, the subject 100, as illustrated in FIG. 4, the examiner winds and attaches the position indication sheet 2 on the trunk of the subject 100 to cover the body surface near the stomach of the subject 100 and determines a positional relationship between the subject 100 and the position indication sheet 2. The capsule endoscope 1 and the liquid Lq1 may be inserted into the subject 100 on which the position indication sheet 2 is attached in advance.

The capsule endoscope 1 and the liquid Lq1 which are inserted into the subject 100 are swallowed from, for example, the mouth of the subject 100. Thereafter, the capsule endoscope 1 and the liquid Lq1 reaches a desired gastrointestinal tract to be observed. The examiner causes the workstation 4 to display an image picked by the capsule endoscope 1 and visually checks the image to recognize an arrival portion (for example, the stomach or the like) of the capsule endoscope 1 in the subject 100. After the examiner inserts the capsule endoscope 1 into the subject 100, the examiner may operate the workstation 4 to start an imaging operation of the capsule endoscope 1.

The examiner inserts an effervescent agent into the subject 100 together with an appropriate amount of water (step S103) to stretch a desired gastrointestinal tract into which the capsule endoscope 1 is inserted. In this manner, the capsule endoscope 1 can easily capture the inside of the gastrointestinal tract serving as a portion to be observed in an imaging field of view, and an image of the inside of the gastrointestinal tract can be easily picked. After the imaging field of view of the capsule endoscope 1 in the gastrointestinal tract is assured, the examiner inserts an antifoaming agent into the gastrointestinal tract in the subject 100 (step S104), and foams generated on the surface of the liquid Lq1 by the effervescent agent are eliminated. In this manner, an image of the inside of the gastrointestinal tract can be picked by the capsule endoscope 1 such that the imaging field of view is not blocked by the foams generated by the effervescent agent.

Thereafter, the examiner brings the permanent magnet 3 close to the position indication sheet 2 attached to the subject 100 into which the capsule endoscope 1 is inserted (step S105) to generate a magnetic field to the capsule endoscope 1 in the subject 100. Specifically, the examiner brings the permanent magnet 3 close to the proximity position represented by the marker of the position indication sheet 2. In this case, the permanent magnet 3 is brought close to the body surface of the subject 100 near the gastrointestinal tract into which the capsule endoscope 1 is inserted to make it possible to apply a magnetic field to the capsule endoscope 1 in the gastrointestinal tract.

The permanent magnet 3 which generates the magnetic field to the capsule endoscope 1 may be a single permanent magnet having a predetermined magnetism. However, the permanent magnet is desirably selected from the plurality of permanent magnets having different magnetisms. In this case, on the basis of selection information (for example, a magnet number) of the permanent magnet indicated by the position indication sheet 2 together with a proximity position, the examiner selects the permanent magnet 3 to be brought close to the proximity position. Thereafter, the examiner refers to a selection result of the permanent magnet displayed on the workstation 4 to re-select the permanent magnet 3 on the basis of the selection result, or adjusts a strength of the magnetic field applied to the capsule endoscope 1. In this manner, the examiner can select a permanent magnet which generates a magnetic field having an appropriate magnetic field strength to the capsule endoscope 1. When the strength of the magnetic field applied to the capsule endoscope 1 is adjusted, the examiner may perform a method of, for example, adjusting a distance between the permanent magnet 3 and the position indication sheet 2.

When the permanent magnet 3 is brought close to the proximity position indicated by the position indication sheet 2, the examiner adjusts the strength and the direction of the magnetic field to the capsule endoscope 1 by operating the permanent magnet 3 to control at least one of the position and the posture of the capsule endoscope 1 by the magnetism of the permanent magnet 3 (step S106). In this case, the examiner oscillates the permanent magnet 3 about a desired marker (i.e., a desired proximity position) of, for example, the position indication sheet 2 or brings the permanent magnet 3 close to all the plurality of markers of the position indication sheet 2 once. The permanent magnet 11 of the capsule endoscope 1 to which the magnetic field of the permanent magnet 3 is applied moves the casing 10 in response to the magnetism of the permanent magnet 3. By the operation of the permanent magnet 11, the capsule endoscope 1 moves or oscillates in, for example, a horizontal direction in the liquid Lq1 and changes at least one of the position and the posture in the gastrointestinal tract serving as a portion to be observed. In this manner, the capsule endoscope 1 sequentially moves images of the inside of the gastrointestinal tract while changing the direction of an imaging field of view to the inside of the gastrointestinal tract in accordance with the motion of the casing 10.

Furthermore, the examiner additionally inserts the liquid Lq1 into the subject 100 (step S107) to increase an amount of the liquid Lq1 in the gastrointestinal tract serving as the portion to be observed. In this case, the capsule endoscope 1, as described above, has a specific gravity which is equal to or less than that of the liquid Lq1 and a center of gravity on the rear-end side of the casing 10. For this reason, the capsule endoscope 1 floats on the surface of the liquid Lq1 such that the imaging field of view is directed almost vertically upward. In accordance with the increase (i.e., an increase in water level) of the capsule endoscope 1 in the gastrointestinal tract, the capsule endoscope 1 moves vertically upward. In this case, the capsule endoscope 1 can pick an image in a state in which the capsule endoscope 1 is further brought close to the inside of the gastrointestinal tract serving as the portion to be observed.

Thereafter, when the examiner maintains a present body position without converting the body position of the subject 100 into another body position (step S108, No), and when imaging of the inside of the gastrointestinal tract serving as the portion to be observed is continued (step S110, No), the procedures subsequent to the step S105 are repeated. In this case, the examiner increases or decreases the amount of the liquid Lq1 in the gastrointestinal tract while referring to the image of the inside of the gastrointestinal tract displayed on the workstation 4, and a position along the vertical direction of the capsule endoscope 1 in the gastrointestinal tract is controlled to a desired position.

On the other hand, when the body position of the subject 100 is converted into another body position to continue imaging in the gastrointestinal tract (step S108, Yes), the present position (for example, a supine position) of the subject 100 is converted into a desired body position (for example, a right lateral decubitus position) (step S109). Thereafter, the examiner repeats the procedures subsequent to the step S105.

In this manner, the permanent magnet 3 is brought close to the proximity position indicated by the position indication sheet 2 to magnetically operate the motion of the capsule endoscope 1, so that at least one of the position and the posture of the capsule endoscope 1 in the gastrointestinal tract serving as a portion to be observed can be controlled. As a result, the capsule endoscope 1 can pick a series of images over the nearly entire area in the gastrointestinal tract. The examiner can cause the workstation 4 to display the series of images picked by the capsule endoscope 1, so that the inside of the gastrointestinal tract serving as the portion to be observed in the subject 100 can be entirely observed.

Thereafter, when the examiner completes the observation of the inside of the gastrointestinal tract serving as the portion to be observed to complete imaging in the gastrointestinal tract (step S110, Yes), the capsule endoscope 1 is guided to an outlet side of the gastrointestinal tract (step S111). In this case, the capsule endoscope 1 is guided to the outlet side by peristaltic motion of the gastrointestinal tract or the flow of the liquid Lq1 or guided to the outlet side of the gastrointestinal tract by the magnetism of the permanent magnet 3 brought close to the body surface of the subject 100, and moves into the next gastrointestinal tract. In this manner, the capsule endoscope 1 completes the imaging in the gastrointestinal tract serving as the portion to be observed. Thereafter, the capsule endoscope 1 picks images of the insides of the gastrointestinal tracts while moving in the subject 100 by peristaltic motions of the gastrointestinal tracts, the flow of the liquid Lq1, the magnetism of the permanent magnet 3, and the like, and the capsule endoscope 1 is discharged out of the subject 100.

The examiner causes the workstation 4 to display the images picked by the capsule endoscope 1, so that the insides of the gastrointestinal tracts of the subject 100 can be observed. On the other hand, the examiner operates the workstation 4 to transmit a control signal which stops the imaging operation, so that the imaging operation of the capsule endoscope 1 which has finished the imaging of the desired portion to be observed may be stopped.

The effervescent agent in step S103 and the antifoaming agent in step S104 may be inserted into the subject 100 as needed. More specifically, the examiner observes the images of the inside of the subject 100 displayed on the workstation 4. When it is determined that the inside of, for example, the gastrointestinal tract must be observed in more detail, the effervescent agent and the antifoaming agent may be sequentially inserted into the subject 100.

Figure 7:
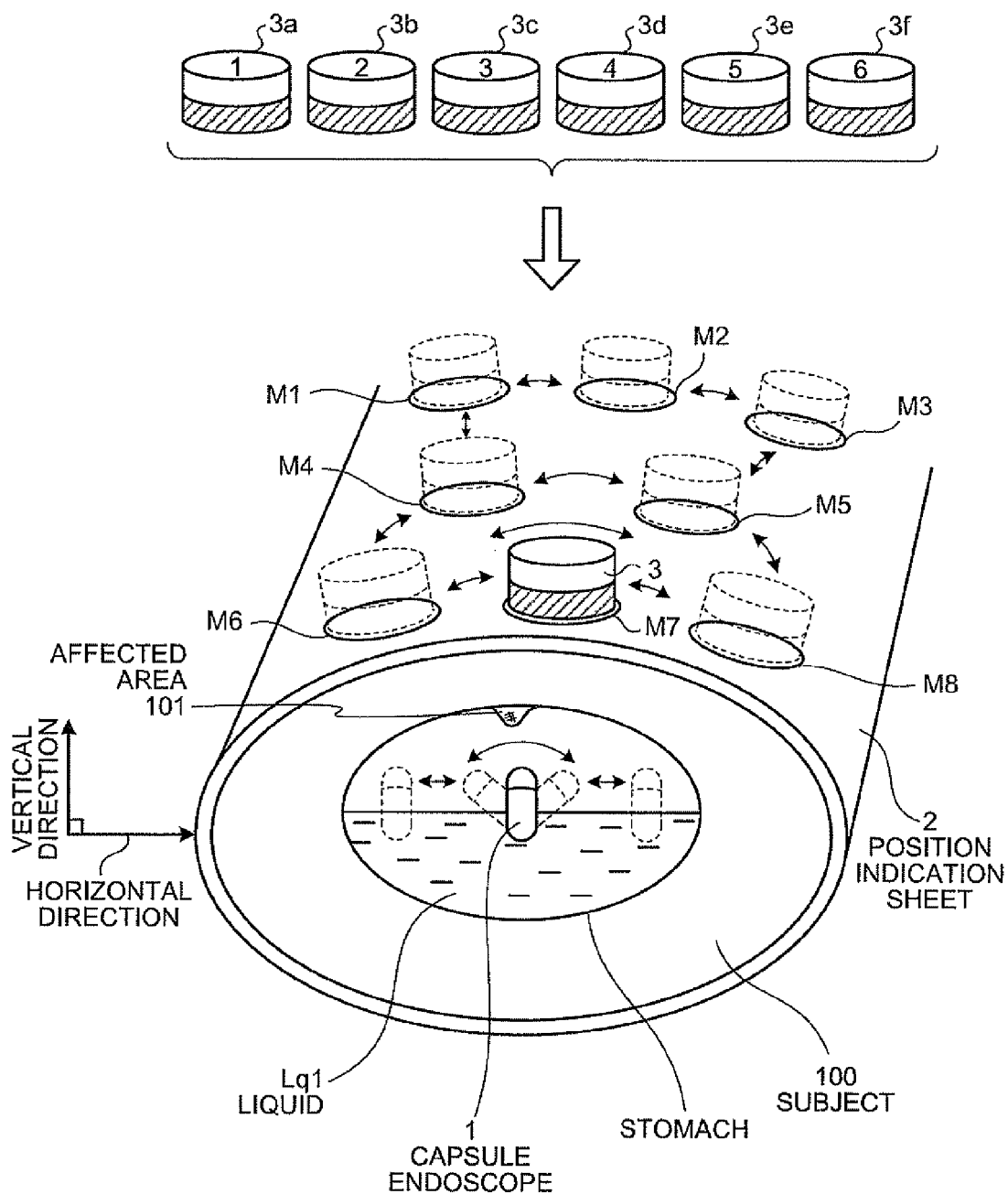
FIG. 7 is a schematic diagram for explaining an operation of a permanent magnet to control at least one of a position and an posture of a capsule endoscope inserted into a subject.

By illustrating a case in which the examiner observes the stomach of the subject 100, an operation of controlling at least one of the position and the posture of the capsule endoscope 1 inserted into the stomach serving as the portion to be observed will be concretely described below. FIG. 7 is a schematic diagram for explaining an operation of the permanent magnet 3 which controls at least one of the position and the posture of the capsule endoscope 1 inserted into the subject 100.

The capsule endoscope 1 and the liquid Lq1 swallowed from the mouth of the subject 100 passes through an esophagus and then, as illustrated in FIG. 7, reaches the stomach serving as the portion to be observed. In this case, the capsule endoscope 1, as described above, has a specific gravity which is equal to or less than that of the liquid Lq1 and a center of gravity on the rear-end side of the casing 10. For this reason, the capsule endoscope 1 in the liquid Lq1, as illustrate in FIG. 7, floats on the surface of the liquid Lq1 in such a state that an imaging field of view is directed almost vertically upward.

On the other hand, the examiner attaches the position indication sheet 2 to the subject 100 to locate the position indication sheet 2 near the stomach serving as the portion to be observed. In this case, the position indication sheet 2 shows a proximity position on the body surface of the subject 100 to the examiner by the plurality of markers. The examiner selects the permanent magnet 3 to be brought close to the proximity position of the subject 100 from six permanent magnets 3a to 3f having magnetisms different from each other on the basis of the selection information (for example, a magnet number) of the permanent magnet indicated by the position indication sheet 2 or the selection result of the permanent magnet displayed on the workstation 4. The examiner brings the selected permanent magnet 3 close to the plurality of markers of the position indication sheet 2 and operates the permanent magnet 3. More specifically, for example, when the body position of the subject 100 is a supine position, the examiner brings the permanent magnet 3 close to all the markers M1 to M8 of the supine position marker group MG1 of the position indication sheet 2 once. The examiner oscillates the permanent magnet 3 about the desired marker (for example, the marker M3). Thereafter, the examiner repeats the operation of the permanent magnet 3 as needed.

The permanent magnet 3 operated by the examiner as described above applies a magnetic field to the capsule endoscope 1 in the liquid Lq1 in the stomach to magnetically capture the capsule endoscope 1 and changes the position and the direction of the magnetic field to the capsule endoscope 1 to control the motion of the capsule endoscope 1. In this case, the capsule endoscope 1 moves or oscillates in the liquid Lq1 in accordance with the operation of the permanent magnet 3 to change at least one of the position and the posture in the stomach. As described above, the permanent magnet 3 changes at least one of the position and the posture of the capsule endoscope 1 in the liquid Lq1 by magnetism. The capsule endoscope 1 operated by the permanent magnet 3 sequentially picks images of the inside of the stomach while changing the position or the direction of an imaging field of view in the stomach.

Thereafter, the examiner increases or decreases the amount of the liquid Lq1 in the stomach as needed or converts the body position of the subject 100 into another body position, for example, the left lateral decubitus position or the right lateral decubitus position. The examiner brings the permanent magnet 3 close to the markers of the left lateral decubitus position marker group MG2 or the right lateral decubitus position marker group MG3 depending on the body position of the subject 100. In this case, the examiner operates the permanent magnet 3 as in the case of the supine position marker group MG1. The permanent magnet 3 operated as described above changes at least one of the position and the posture of the capsule endoscope 1 as in the case of the subject 100 in the supine position.

As described above, the permanent magnet 3 controls at least one of the position and the posture of the capsule endoscope 1 by magnetism, so that the capsule endoscope 1 can entirely image a stomach wall on a vertically upward side of the liquid Lq1, i.e., the stomach wall stretched by the effervescent agent. In this manner, the capsule endoscope 1 can pick a series of images over the nearly entire area of the stomach wall, and can reliably pick images of an affected area 101 of, for example, the stomach wall. This is true when the amount of the liquid Lq1 which floats the capsule endoscope 1 is increased or decreased. More specifically, the capsule endoscope 1 is displaced in the vertical direction in accordance with a change in level of the liquid Lq1. For example, the capsule endoscope 1 can be brought close to the stomach wall to make it possible to pick an enlarged image of the stomach wall. In this case, the capsule endoscope 1 can be brought close to the affected area 101 of the stomach wall, and can pick an enlarged image of the affected area 101.

The capsule endoscope 1 floating on the surface of the liquid Lq1 is designed to have a center of gravity near the center of the casing 10 or on the front-end side of the casing 10, and an imaging field of view may be directed from the liquid Lq1 to the vertically upward side by a magnetic field applied from the permanent magnet 3. However, as described above, the center of gravity is desirably arranged on the rear-end side of the casing 10. In this case, since the imaging field of view of the capsule endoscope 1 can be directed on the vertically upward side by the floatage of the liquid Lq1, the motion of the capsule endoscope 1 can be controlled by using a permanent magnet having a weaker magnetism, and the permanent magnet 3 which controls the motion of the capsule endoscope 1 can be miniaturized.

On the other hand, the capsule endoscope 1 having finished the imaging of the inside of the stomach serving as the desired portion to be observed moves to the next gastrointestinal tract (for example, a duodenum) by the procedure in step S111 described above. More specifically, the capsule endoscope 1 moves from the stomach to a pyloric part by a magnetism applied from the permanent magnet 3 brought close to the pyloric part of the subject 100. In this case, the examiner converts the body position of, for example, the subject 100 into the right lateral decubitus position. Thereafter, the permanent magnet 3 is moved toward the body surface of the subject 100 near the pyloric part, and the capsule endoscope 1 may be guided to the pyloric part by the magnetism applied from the permanent magnet 3. Alternatively, the capsule endoscope 1 may be guided to the pyloric part by the liquid Lq1 flowing from the stomach to the duodenum.

Figure 8:
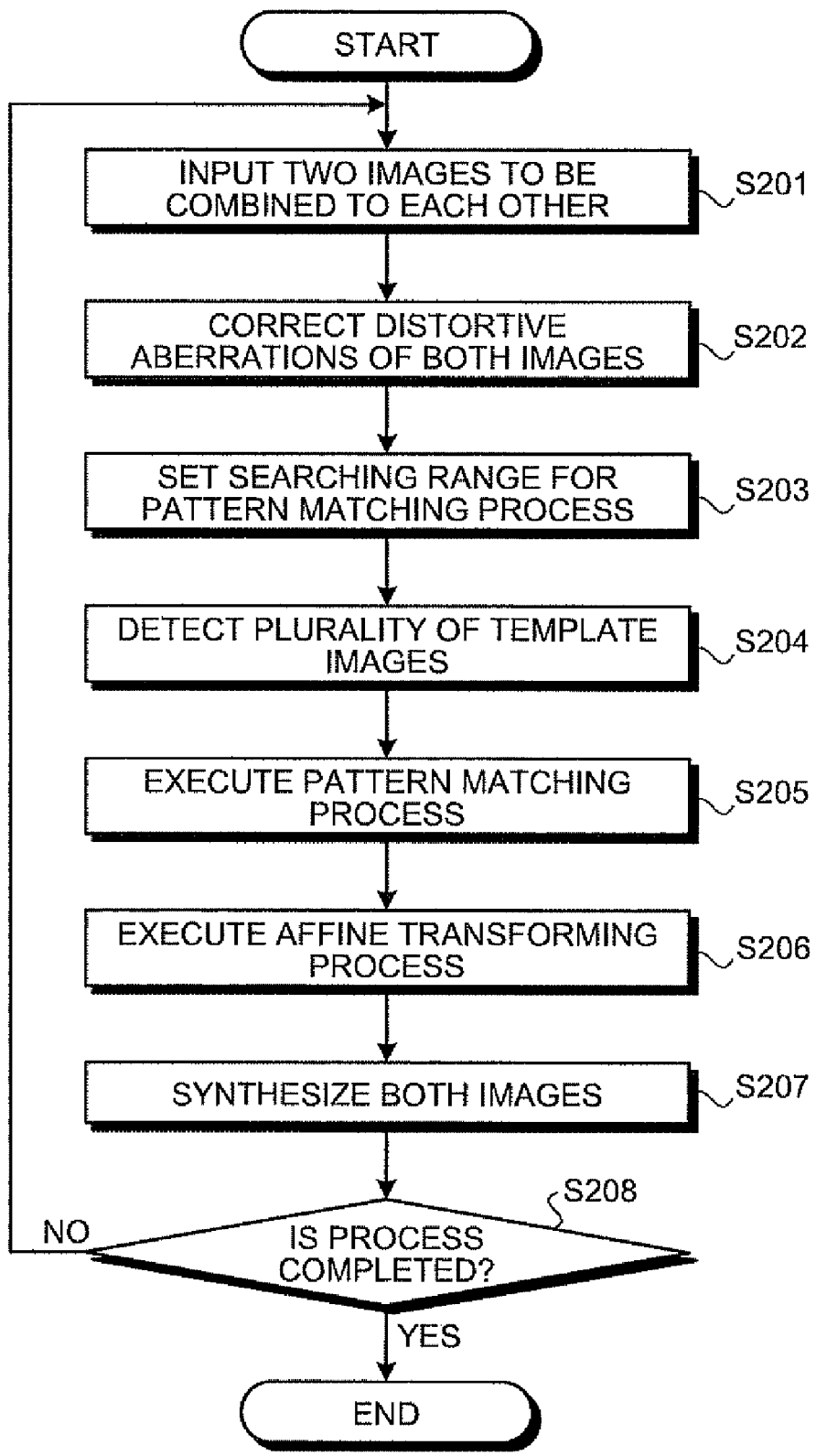
FIG. 8 is a flow chart illustrating a procedure of an image combining process performed by a control unit of a workstation.
Figure 9:
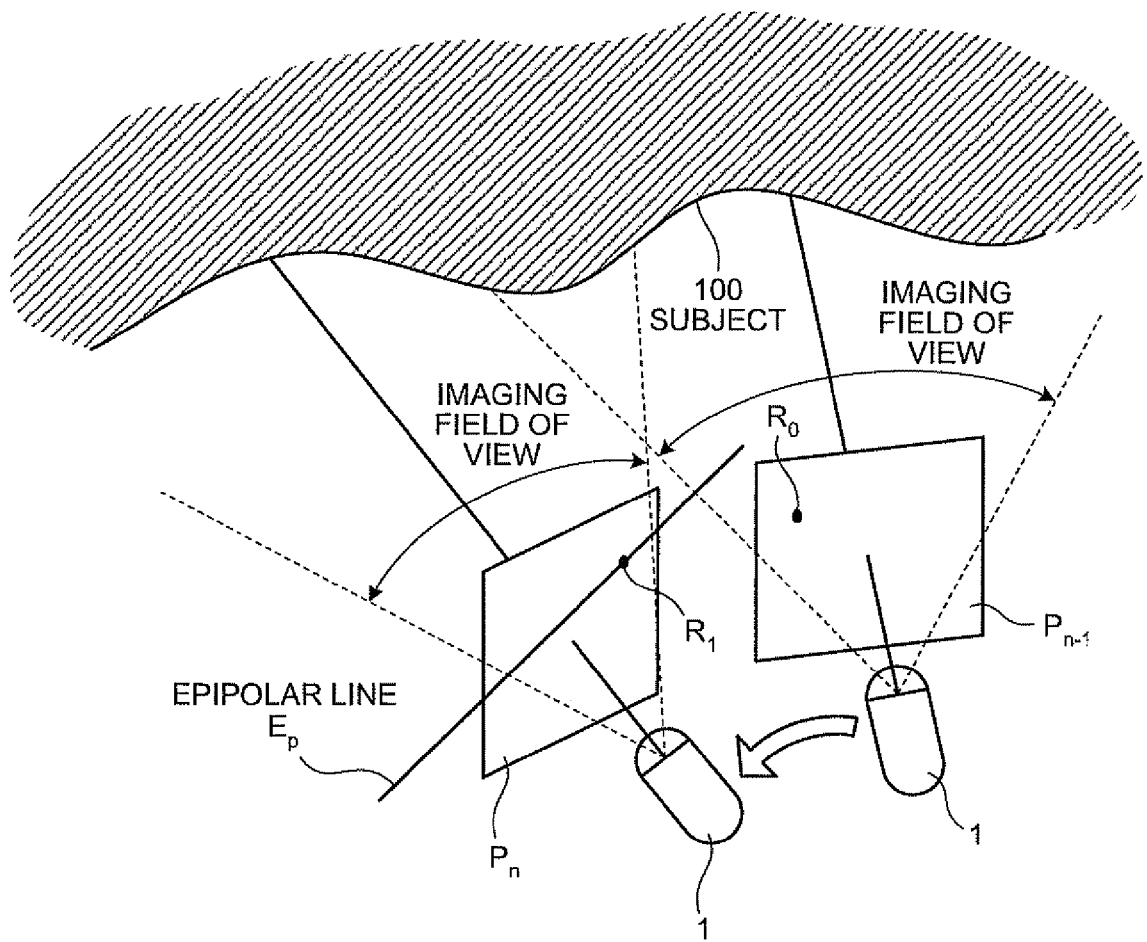
FIG. 9 is a schematic diagram for explaining an operation of a control unit which combines a plurality of images to each other.

An image combining process of combining a plurality of images in the subject 100 picked by the capsule endoscope 1 will be described below in detail. FIG. 8 is a flow chart illustrating a procedure of an image combining process performed by the control unit 9 of the workstation 4. FIG. 9 is a schematic diagram for explaining an operation of the control unit 9 which combines a plurality of images to each other.

The control unit 9 of the workstation 4 recognizes relative positions and relative directions of a plurality of images picked by the capsule endoscope 1 on the basis of a plurality of pieces of image information acquired from the capsule endoscope 1 and pieces of position/posture information associated with the plurality of pieces of image information, respectively, and combines the plurality of images on the basis of the Epipolar geometry. More specifically, in FIG. 8, the control unit 9 inputs two images to be combined (step S201). In this case, the input unit 6 inputs information for designating the two images to be combined to each other to the control unit 9 depending on an input operation of an examiner. The control unit 9 reads two images $P_n$ and $P_{n-1}$ to be combined from the storage unit 8 on the basis of the input information from the input unit 6. At the same time, the control unit 9 reads the pieces of position/posture information associated with the images $P_n$ and $P_{n-1}$ from the storage unit 8. The image combining unit 9e recognizes the position and the posture of the capsule endoscope 1 and an inclination of an image to the z axis obtained when the images $P_n$ and $P_{n-1}$ are picked on the basis of the pieces of position/posture information of the images $P_n$ and $P_{n-1}$.

The control unit 9 corrects distortive aberrations of the read two images $P_n$ and $P_{n-1}$ (step S202). In this case, the image combining unit 9e corrects the distortive aberrations of the images $P_n$ and $P_{n-1}$. In this manner, when a photographic subject common in both the images $P_n$ and $P_{n-1}$ is imaged, the image combining unit 9e synthesizes pixel regions (i.e., high degree of similarity) representing the common photographic subject to make it possible to combine the images $P_n$ and $P_{n-1}$ to each other.

Thereafter, the control unit 9 sets a searching range of a pattern matching process of searching for pixel regions having a high degree of similarity between the images $P_n$ and $P_{n-1}$ (step S203). In this case, the image combining unit 9e calculates, on the basis of the Epipolar geometry, a plurality of reference points on the image $P_{n-1}$ and calculates a plurality of Epipolar lines on the image $P_n$ corresponding to the plurality of reference points, respectively.

The images $P_n$ and $P_{n-1}$ are images picked before and after the capsule endoscope 1 changes at least one of the position and the posture. More specifically, the image $P_{n-1}$, for example, as shown in FIG. 9, is an image obtained by imaging the inside of the subject 100 by the capsule endoscope 1, and the image $P_n$ is an image obtained by imaging the inside of the subject 100 after the capsule endoscope 1 has changed its position and posture. The images $P_n$ and $P_{n-1}$ have pixel regions having a high degree of similarity when the images $P_n$ and $P_{n-1}$ include the same photographic subject. The image combining unit 9e sets a plurality of reference points (for example, six or more points) corresponding to the pixel regions having the high degree of similarity on the image $P_{n-1}$, and sets a plurality of Epipolar lines corresponding to the plurality of reference points on the image $P_n$.

For example, the image combining unit 9e, as shown in FIG. 9, sets a reference point $R_0$ on the image $P_{n-1}$ and sets an Epipolar line $E_p$ corresponding to the reference point $R_0$ on the image $P_n$. When the reference point $R_0$ represents position coordinates of the pixel regions having the high degree of similarity between the images $P_n$ and $P_{n-1}$ the image combining unit 9e can set the Epipolar line $E_p$ on the image $P_n$, for example, between two opposite apexes of the image $P_n$. The Epipolar line $E_p$ includes a corresponding point $R_1$ corresponding to the reference point $R_0$. The corresponding point $R_1$ represents position coordinates of the pixel regions, on the image $P_n$, having a degree of similarity higher than that of pixel regions on the image $P_{n-1}$ on which the position coordinates are set by the reference point $R_0$.

In this manner, the image combining unit 9e sets a plurality of reference points (for example, six or more points) on the image $P_{n-1}$ and sets a plurality of Epipolar lines corresponding to the plurality of reference points on the image $P_n$. In this case, the image combining unit 9e sets pixel regions near the plurality of Epipolar lines within a searching range for a pattern matching process.

The control unit 9 detects a plurality of pixel regions (template images) serving as references of the pattern matching process on the basis of the image $P_{n-1}$ (step S204). In this case, the image combining unit 9e detects a plurality of template images (for example, 6 or more images) corresponding to the plurality of reference points illustrated as the reference point $R_0$.

Thereafter, the control unit 9 executes a pattern matching process of detecting the plurality of pixel regions on the image $P_n$ having a degree of similarity higher than that of a plurality of detected template images (step S205). In this case, the image combining unit 9e uses the pixel region on the image $P_n$ near, for example, the Epipolar line $E_p$ as a searching range of the pattern matching process to detect a pixel region on the image $P_n$ having a degree of similarity higher than that of the template image corresponding to the reference point $R_0$. The image combining unit 9e calculates the corresponding point $R_1$ for determining position coordinates on the image $P_n$ of the pixel region having the high degree of similarity. The image combining unit 9e repeats the pattern matching process to the plurality of template images and the plurality of Epipolar lines. For example, the image combining unit 9e detects six or more pixel regions on the image $P_n$ corresponding to six or more template images. The image combining unit 9e calculates six or more corresponding points on the image $P_n$ corresponding to the six or more coordinates which determine position coordinates of the six or more pixel regions, or the six or more reference points illustrated as the reference point $R_0$ described above.

When, for example, the six or more reference points and the six or more corresponding points on the images $P_n$ and $P_{n-1}$ are calculated, the control unit 9 executes an affine transforming process to both the images $P_n$ and $P_{n-1}$ (step S206). In this case, the image combining unit 9e uses the calculated six or more reference points and the calculated six or more corresponding points to calculate an affine parameter on the basis of the least-squares method. The image combining unit 9e transforms a coordinate system on, for example, the image $P_{n-1}$ into a coordinate system on the image $P_n$ to achieve the affine transforming process of both the images $P_n$ and $P_{n-1}$ based on the calculated affine parameters.

The control unit 9 synthesizes both the images $P_n$ and $P_{n-1}$ subjected to the affine transforming process (step S207) to combine both the images $P_n$ and $P_{n-1}$ into one processed image (for example, a panoramic image). In this case, the image combining unit 9e synthesizes pixel regions (i.e., pixel regions having a high degree of similarity) representing a photographic subject common in both the images $P_n$ and $P_{n-1}$ subjected to the affine transforming process to generate a processed image obtained by combining both the images $P_n$ and $P_{n-1}$.

Thereafter, when the control unit 9 continuously performs the image combining process (step S208, No), the procedure subsequent to step S201 described above is repeated. In this case, the image combining unit 9e can sequentially combine a plurality of images (for example, a series of images over the nearly entire area of the inside of a stomach) picked by the capsule endoscope 1, and can generate a panoramic image representing the entire image of an observed image in the subject 100, for example, a stomach wall. On the other hand, the control unit 9 completes an image combining process when information for designating completion of processing is input by the input unit 6 (step S208, Yes). In this case, the control unit 9 stores a processed image generated by the image combining process in the storage unit 8.

In this case, the control unit 9 can generate a columnar processing image almost three-dimensionally showing the inside of the gastrointestinal tract in the subject 100 on the basis of a processed image, for example, a band-shaped panoramic image generated by the image combining process. In this case, the image combining unit 9e transforms an orthogonal coordinate system of the band-shaped panoramic image into a columnar coordinate system and synthesizes both the ends of the band-shaped panoramic image in the longitudinal direction to generate a columnar processed image. The control unit 9 stores the columnar processed image in the storage unit 8.

Figure 10:
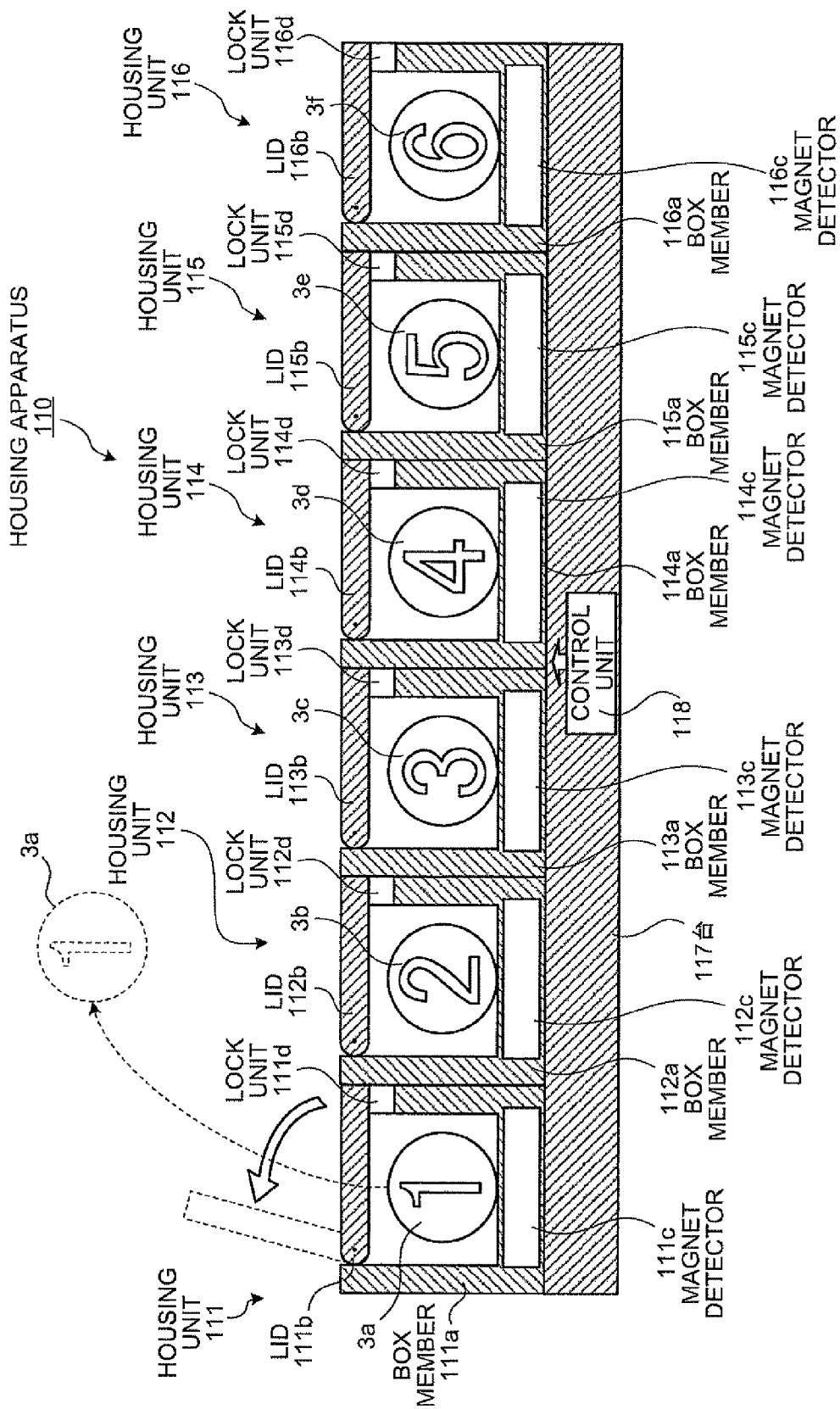
FIG. 10 is a schematic diagram typically showing one configuration of a housing apparatus in which a plurality of permanent magnets are housed.

A permanent magnet housing apparatus according to the present invention will be described below. The permanent magnet housing apparatus according to the first embodiment houses a plurality of permanent magnets which are prepared to select the permanent magnet 3 for controlling movement of the capsule endoscope 1. FIG. 10 is a schematic diagram typically showing one configuration of the housing apparatus in which a plurality of permanent magnets are housed. The housing apparatus in which six permanent magnets 3a to 3f prepared to select the permanent magnet 3 will be illustrated. The number of permanent magnets may be 2 or more. The number of permanent magnets does not limit the configuration of the housing apparatus.

As shown in FIG. 10, the housing apparatus 110 has six housing units 111 to 116 in which the permanent magnets 3a to 3f are housed, a table 117 which integrally connects the housing units 111 to 116 with each other, and a control unit 118 which controls opening/closing drives of the housing units 111 to 116. For example, magnet numbers 1 to 6 which specify permanent magnets 3a to 3f, respectively, are added to the permanent magnets 3a to 3f, respectively. In this case, a larger number given to any one of the permanent magnets 3a to 3f indicates that the permanent magnet has a stronger magnetism.

The housing unit 111 is for housing the permanent magnet 3a of magnet number 1. More specifically, the housing unit 111 has a box member 111a which houses the permanent magnet 3a, a lid 111b which opens or closes an opening end of the box member 111a, a magnet detector 111c which detects the permanent magnet 3a housed in the box member 111a, and a lock unit 111d which locks the lid 111b. The box member 111a is a member having, for example, a recessed side section, and the lid 111b is pivotally arranged near the opening end. Although not shown, an opening/closing state detector 111e which detects an opening or closing state of the lid 111b is arranged. The permanent magnet 3a housed in the box member 111a is inserted or pulled by opening or closing the lid 111b. When the permanent magnet 3a is housed in the box member 111a, the magnet detector 111c detects a magnetic field or a weight of the permanent magnet 3a, and, based on the detection result, the presence/absence of the permanent magnet 3a in the box member 111a is detected. The magnet detector 111c notifies the control unit 118 of the detection result of the permanent magnet 3a. The lock unit 111d locks the lid 111b or unlocks the lid 111b under the control of the control unit 118. Furthermore, the opening/closing state detector 111e detects whether the lid 111b is opened or closed, and notifies the detection result to the control unit 118.

The housing units 112 to 116 are for housing the permanent magnets 3b to 3f of magnet numbers 2 to 6 and have almost the same configuration and function as those of the housing unit 111 each. More specifically, the housing units 112 to 116 have box members 112a to 116a which individually house the permanent magnets 3b to 3f, respectively, lids 112b to 116b which open or close the opening ends of the box members 112a to 116a, magnetism detectors 112c to 116c which individually detect the permanent magnets 3b to 3f housed in the box members 112a to 116a, respectively, lock units 112d to 116d which lock the lids 112b to 116b, respectively, and opening/closing state detectors 111e to 116e (not shown) which detect the opening/closing states of the lids 112b to 116b, respectively. In this case, the box members 112a to 116a have almost the same function as that of the box member 111a of the housing unit 111, and the lids 112b to 116b have almost the same function as that of the lid 111b of the housing unit 111. The magnetism detectors 112c to 116c have almost the same function as that of the magnet detector 111c of the housing unit 111, the lock units 112d to 116d have almost the same function as that of the lock unit 111d of the housing unit 111, and the opening/closing state detectors 112e to 116e have almost the same function as that of the opening/closing state detector 111e of the housing unit 111. Furthermore, although not shown, depending on selection information (for example, magnet number or strength of a magnetic field to be generated) of the permanent magnet represented together with a proximity position by the position indication sheet 2, a permanent magnet selector which selects a lid to be opened or closed (permanent magnet to be extracted) is arranged.

The control unit 118 is provided for example on the table 117 and controls the drives of the magnetism detectors 111c to 116c and the lock units 111d to 116d. More specifically, the control unit 118 acquires detection results of the permanent magnets 3a to 3f from the magnetism detectors 111c to 116c, acquires opening/closing state detection results of the lids 111b to 116b from the opening/closing state detectors 111e to 116e, acquires input information to the permanent magnet selector, and controls drives of the lock units 111d to 116d on the basis of the acquired input information and the detection results. In this case, when the control unit 118 acquires the detection results representing the presence of a permanent magnet from all the magnetism detectors 111c to 116c, and drive control for locking is performed to the lock units 111d to 116d. Furthermore, when a selection result selected by the permanent magnet selector is input, the control unit 118 performs drive control for unlocking a lid (any one of the lids 111b to 116b) of the selected permanent magnet to a lock unit (any one of the lock units 111d to 116d corresponding to a lid to be unlocked). At this time, the other lock units (lock units corresponding to lids except for lids to be unlocked) are kept locked.

The selected permanent magnet is taken out, and the capsule endoscope 1 in the subject 100 is guided by using the permanent magnet. At this time, when the control unit 118 acquires a detection result representing the absence of a permanent magnet from any one of the magnetism detectors 111c to 116c, the control unit 118 keeps the housing unit having a magnet detector which performs notification of the detection result representing the absence of the permanent magnet, i.e., a lock unit (any one of the lock units 111d to 116d) of the housing unit from which the permanent magnet is extracted in an unlocking state. At the same time, the control unit 118 keeps the housing units having remaining magnet detectors which perform notification of the detection result of the absence of permanent magnet, i.e., a lock unit (any one of the lock units 111d to 116d) of each of the housing unit which houses the permanent magnet in a state in which the lid is locked. Guidance of the capsule endoscope 1 is completed, the permanent magnet is returned to the housing unit (any one of the housing units 111 to 116), and the magnet detector corresponding to the housing unit detects the presence of a permanent magnet. Furthermore, the lid of the housing unit is closed, and the opening/closing state detectors 111e to 116e detect that the lids 111b to 116b are closed. When the control unit 118 is notified of the detection results, the control unit 118 performs drive control for locking to the lock units 111d to 116d of all the lids 111b to 116b. At this time, the lid of the housing unit may be manually closed or may be automatically closed on the basis of a detection result of the magnetic detector. The control unit 118, the magnetism detectors 111c to 116c, the lock units 111d to 116d, and the opening/closing state detectors 111e to 116e may perform electric detection or electric control, or may perform detection or control by a mechanical mechanism. When the electric detection is performed, the weight of the permanent magnet may be detected, a magnetic field of the permanent magnet may be detected, or RFID tags are added to the permanent magnets and read units which read information of the RFID tags may be arranged on the magnetism detectors 111c to 116c. A shield to decrease a magnetic field leaking to the outside may be arranged on the housing apparatus 110. The shield consists of a ferromagnetic body. Furthermore, a unit which prevents the permanent magnet from being taken out is not limited to a combination of the lid and the lock unit. For example, the unit may be a unit (binding unit) which binds the permanent magnet in the housing unit. A ferromagnetic body is arranged in the housing unit, and the permanent magnet is bound by an adsorptive power between the ferromagnetic body and the permanent magnet, so that a binding state of the permanent magnet may be controlled by using a ferromagnetic body distance changing unit which changes a distance between the ferromagnetic body and the permanent magnet. The binding unit may be an electromagnet arranged in the housing unit, and a binding state of the permanent magnet may be controlled by a current flowing in the electromagnet. As the binding unit, a fixing unit which mechanically fixes the permanent magnet in the housing may be used.

The control unit 118 drives and controls any one of the permanent magnets 3a to 3f housed in the housing units 111 to 116 to make it possible to take out the permanent magnet, so that a plurality of permanent magnets are prevented from being extracted at once. For example, as shown in FIG. 10, when an examiner takes out the permanent magnet 3a from the permanent magnets 3a to 3f, the control unit 118 acquires a detection result representing the absence of a permanent magnet from the magnet detector 111c, and acquires a detection result representing the presence of a permanent magnet from the remaining magnetism detectors 112c to 116c. In this case, the control unit 118 performs drive control for unlocking the lid to the lock unit 111d, and performs drive control which locks the lid to the remaining lock units 112d to 116d.

In this manner, the examiner can easily manage the plurality of permanent magnets, and can take out only a necessary permanent magnet from the housing apparatus 110. As a result, an excessive number of permanent magnets can be prevented from being unintentionally brought close to the subject 100 into which the capsule endoscope 1 is inserted, and the inside of the subject 100 can be more safely observed without applying an excessive magnetic field to the subject.

Figure 11:
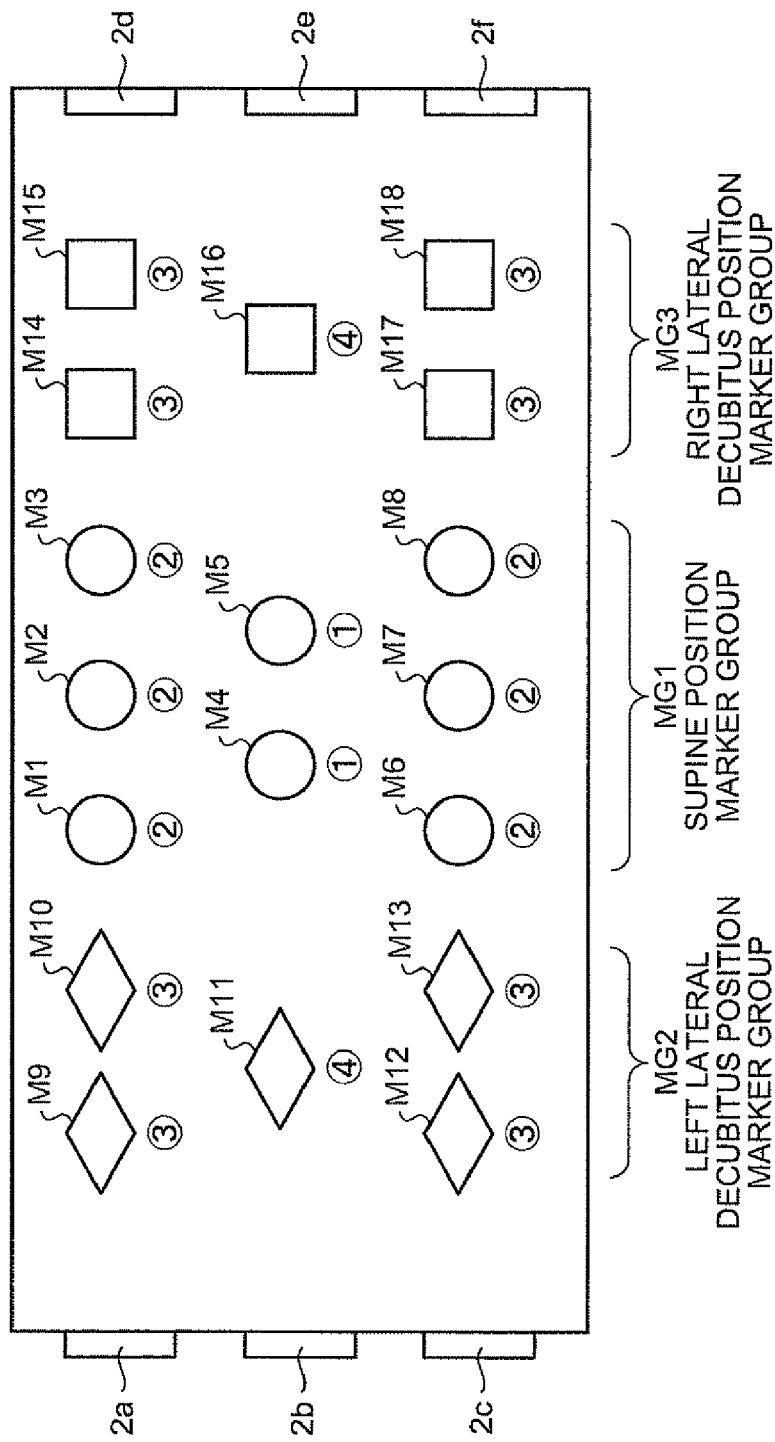
FIG. 11 is a schematic diagram showing one configuration of a position indication sheet on which a plurality of markers having different shapes for body positions of a subject are formed.

On the position indication sheet 2 according to the first embodiment of the present invention, as markers representing proximity positions on the body surface of the subject 100, for example, a plurality of markers each having a shape of one type such as a circular form are formed. However, the present invention is not limited to these markers. A plurality of markers to be formed on the position indication sheet 2 may be, for example, markers having shapes which change depending on body positions of the subject 100. In this case, on the position indication sheet 2, for example, as shown in FIG. 11, the plurality of markers M1 to M18 are formed such that the supine position marker group MG1, the left lateral decubitus position marker group MG2, and the right lateral decubitus position marker group MG3 have shapes different from each other.

Figure 12:
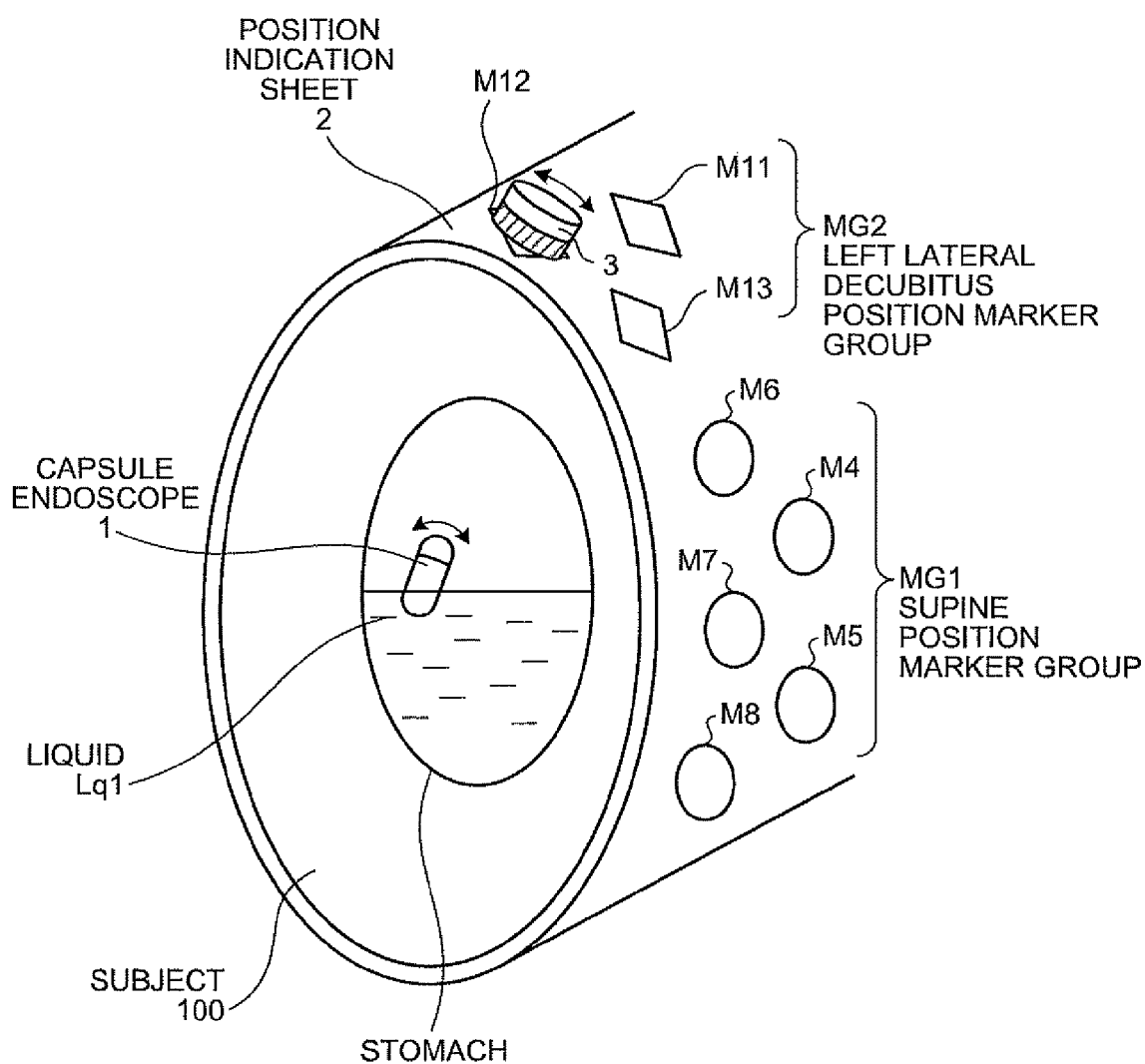
FIG. 12 is a schematic diagram illustrating a state in which proximity positions are indicated by the plurality of markers having different shapes for body positions on the position indication sheet.

The position indication sheet 2 on which the markers M1 to M18 having the shapes different depending on the body positions of the subject 100 can clearly show the proximity positions for body positions of the subject 100. For example, when a body position of the subject 100 is a left lateral decubitus position, the position indication sheet 2, as shown in FIG. 12, can clearly show proximity positions where the permanent magnets 3 are brought close to the subject 100 having the left lateral decubitus position by the left lateral decubitus position marker group MG2. As a result, the position indication sheet 2 can suppress an unnecessary operation of the examiner such as an operation of unnecessarily bringing the permanent magnet 3 close to a proximity position to be shown to the examiner when the subject 100 has another body position.

In the first embodiment of the present invention, the plurality of markers representing proximity positions are formed on the position indication sheet 2. However, the present invention is not limited to the markers. At least one marker representing a proximity position may be formed on the position indication sheet 2, and the number of markers is not limited to 18. More specifically, when an optical system configuring the imaging unit of the capsule endoscope is made wider, the field angle is set to about 100 to 140 degrees, and an imaging field of view of the capsule endoscope is made wider, the number of the markers forming the position indication sheet 2 can be decreased. For example, when the position indication sheet 2 on which one marker is formed is used, an imaging field of view of the capsule endoscope inserted into a gastrointestinal tract is widened, and a permanent magnet or the like which is brought close to the marker on the position indication sheet 2 is oscillated near the marker, so that a series of images over a nearly entire area in the gastrointestinal tract can be picked by the capsule endoscope.

As described above, the permanent magnet housing apparatus according to the first embodiment has a configuration in which a plurality of permanent magnets used to guide the capsule endoscope are individually housed in a plurality of housing units, respectively, (one permanent magnet in each housing unit), and binding units which bind the plurality of permanent magnets in the plurality of housing units are arranged in the housing units, respectively, a permanent magnet detector detects whether the permanent magnets are housed in the plurality of housing units, and, on the basis of detection results of the permanent magnets, the permanent magnets in the plurality of housing units are selectively kept in a binding state or a nonbinding state. For this reason, the plurality of permanent magnets can be easily managed, and only a permanent magnet necessary to guide the capsule endoscope can be taken out from the plurality of permanent magnets housed in the plurality of housing units, respectively. As a result, for example, an excessive number of permanent magnets can be prevented from being unintentionally brought close to the subject into which the capsule endoscope is inserted, and the inside of the subject can be safely observed without applying an excessive magnetic field to the subject.

In the first embodiment of the present invention, a position indication sheet representing a position where a permanent magnet is brought close to a body surface of a subject, i.e., a proximity position is attached to the subject, a permanent magnet is brought close to the proximity position represented by the position indication sheet, and at least one of a position and an posture of the capsule endoscope in a liquid inserted into the gastrointestinal tract of the subject is changed by a magnetism of the permanent magnet. For this reason, images of the inside of the gastrointestinal tract picked by the capsule endoscope are visually checked on a display, and a series of images over a nearly entire area in the gastrointestinal tract can be picked by the capsule endoscope without sequentially recognizing imaging field of views of the capsule endoscope to the inside of the gastrointestinal tract. Therefore, a body-insertable apparatus system which can easily acquire images necessary to observe an inside of a desired gastrointestinal tract within a short period of time can be realized.

By using the body-insertable apparatus system, a doctor, as a matter of course, a healthcare worker such as a nurse other than a doctor can easily change at least one of the position and the posture of the capsule endoscope in a gastrointestinal tract serving as a portion to be observed, and a series of images over a nearly entire area in the gastrointestinal tract can be easily acquired in a workstation. At the same time, the doctor can be prevented from being tied down in an operation (i.e., a guide operation of the capsule endoscope) of a permanent magnet which magnetically guides the capsule endoscope in the gastrointestinal tract.

Furthermore, since at least one of the position and the posture of the capsule endoscope in the gastrointestinal tract can be actively changed by magnetism, an image of a desired position in the gastrointestinal tract can be easily picked by the capsule endoscope, and the inside of the gastrointestinal tract serving as a desired portion to be observed can be entirely observed within a short period of time. In particular, when a gastrointestinal tract such as a stomach having a relatively simple shape is observed, the functional effects are remarkable.

A second embodiment of the present invention will be described below. In the first embodiment described above, the permanent magnet 3 is brought close to a proximity position to change at least one of the position and the posture of the capsule endoscope 1 in the liquid Lq1. However, in the second embodiment, a drive electric power is controlled to bring an electromagnet whose magnetic field strength can be controlled close to a proximity position to change at least one of the position and the posture of the capsule endoscope 1 in the liquid Lq1.

Figure 13:
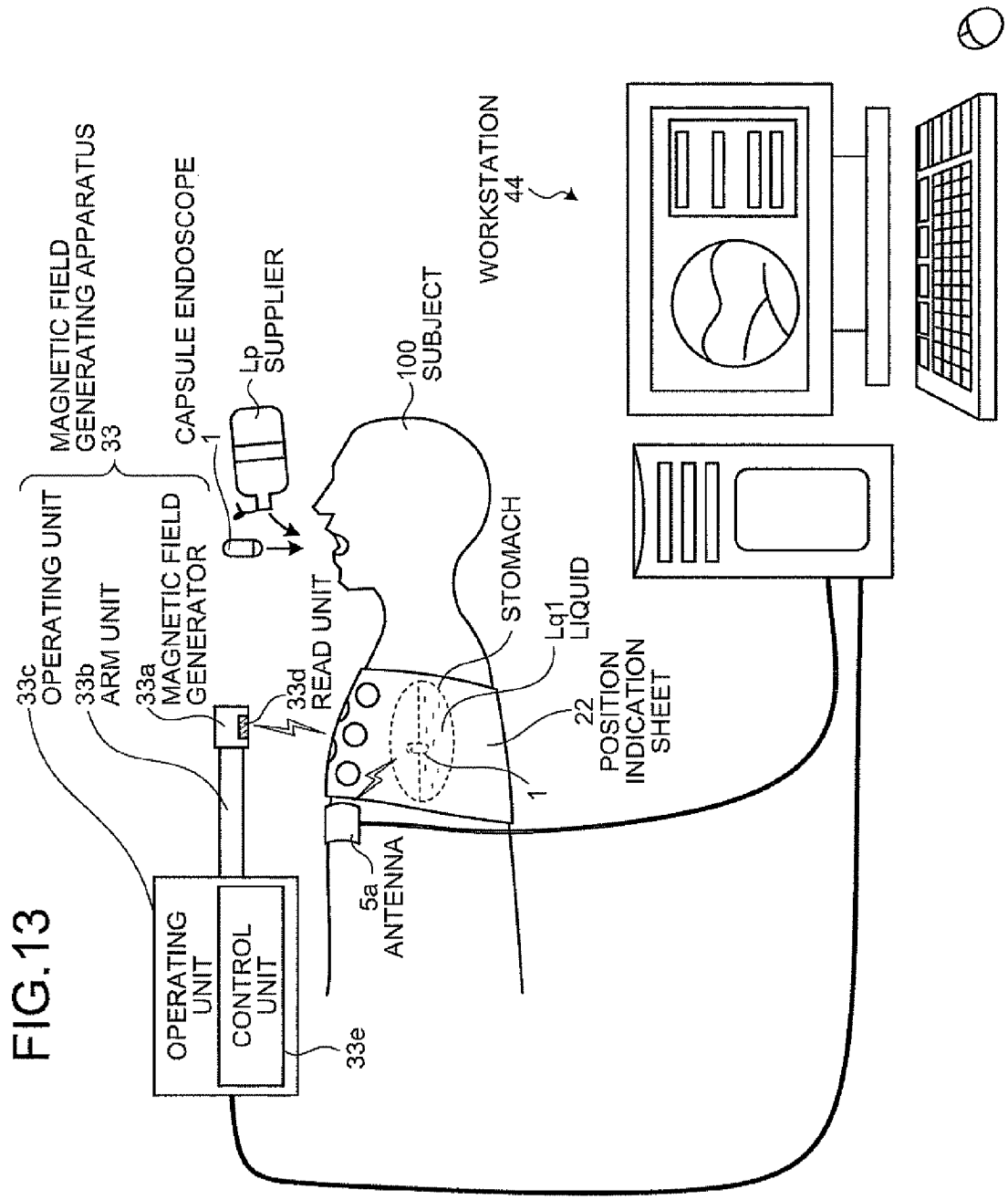
FIG. 13 is a schematic diagram showing one configuration of a body-insertable apparatus system according to a second embodiment of the present invention.

FIG. 13 is a schematic diagram showing one configuration of a body-insertable apparatus system according to the second embodiment of the present invention. As shown in FIG. 13, the body-insertable apparatus system according to the second embodiment has a position indication sheet 22 in place of the position indication sheet 2 of the body-insertable apparatus system according to the first embodiment, has a magnetic field generating apparatus 33 in place of the permanent magnet 3, and has a workstation 44 in place of the workstation 4. Other configurations are the same as those of the first embodiment, and the same reference numerals as in the first embodiment denote the same parts in the second embodiment.

The position indication sheet 22 has almost the same function as that of the position indication sheet 2 according to the first embodiment described above. In this case, the position indication sheet 22 shows a plurality of proximity positions of the magnetic field generating apparatus 33 to the body surface of the subject 100 to an examiner. The examiner, for example, brings the magnetic field generating apparatus 33 close to all the plurality of proximity positions once. The position indication sheet 22 has an information recording medium such as an RFID tag on which information for determining a magnetic field strength of the magnetic field generating apparatus 33 for each of the proximity positions. The information recording media are arranged at the proximity positions represented by the position indication sheet 22.

The magnetic field generating apparatus 33 generates a magnetic field to the capsule endoscope 1 inserted into the gastrointestinal tract of the subject 100, and functions as a magnetic field generator which changes at least one of the position and the posture of the capsule endoscope 1 by the magnetic field. More specifically, the magnetic field generating apparatus 33 has a magnetic field generator 33a which generates a magnetic field to the capsule endoscope 1 inserted into the gastrointestinal tract of the subject 100, an arm unit 33b having one end to which the magnetic field generator 33a is connected, and an operating unit 33c which operates the magnetic field generator 33a through the arm unit 33b. The magnetic field generator 33a has a read unit 33d which reads information from the information recording media arranged on the position indication sheet 22 through a predetermined radio wave. The operating unit 33c has a control unit 33e which controls drives of the magnetic field generator 33a and the read unit 33d. The magnetic field generating apparatus 33 is electrically connected to the workstation 44 through a cable or the like and controlled by the workstation 44.

Figure 14:
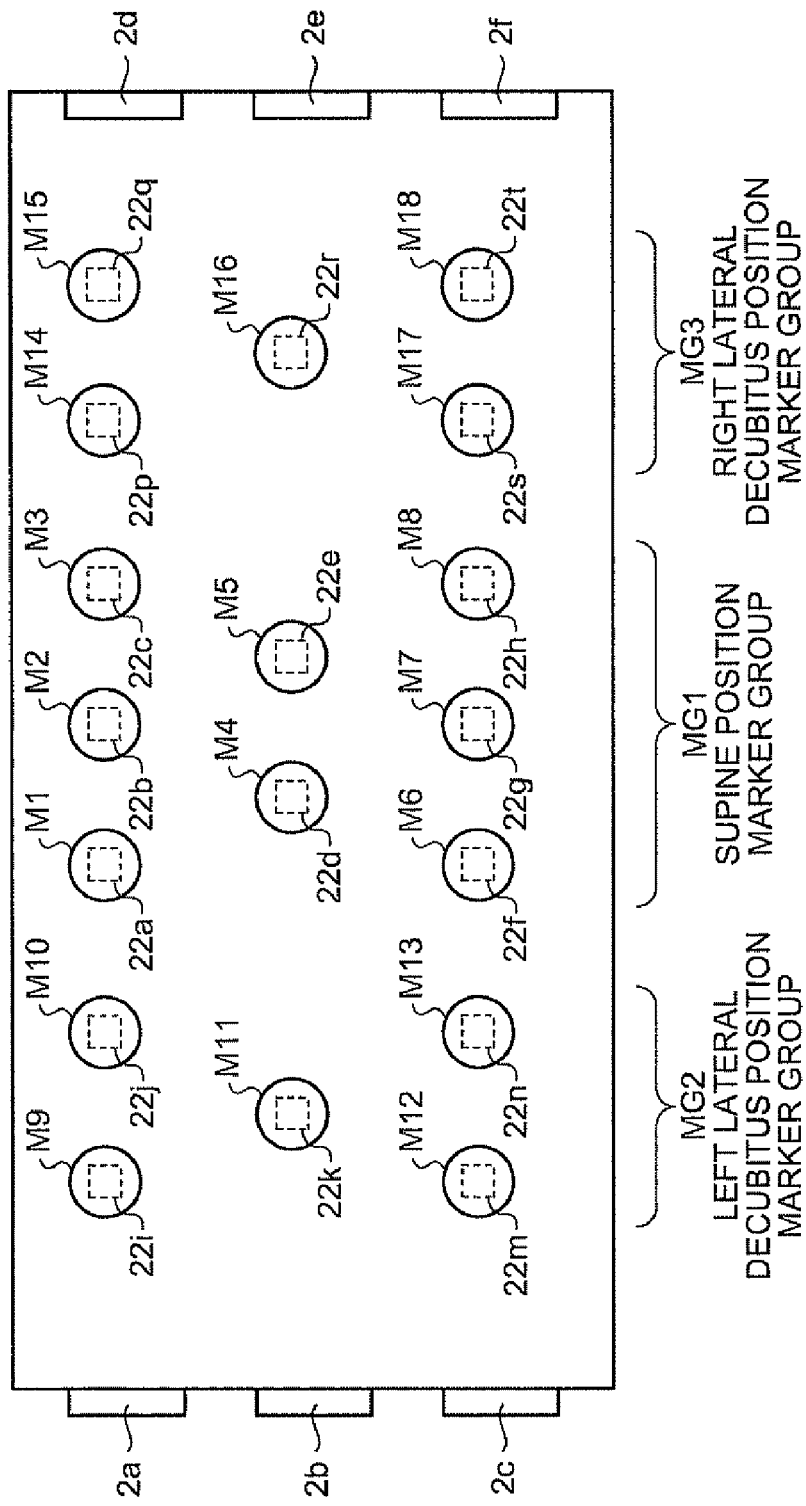
FIG. 14 is a schematic diagram showing one configuration of a position indication sheet according to the second embodiment of the invention.

A configuration of the position indication sheet 22 according to the second embodiment of the present invention will be described below in detail. FIG. 14 is a schematic diagram showing one configuration of the position indication sheet 22 according to the second embodiment of the invention. As shown in FIG. 14, the position indication sheet 22 has REID tags 22a to 22t at proximity positions in place of magnet numbers serving as an example of selection information of the permanent magnet 3. Other configurations are the same as those in the first embodiment, and the same reference numerals as in the first embodiment denote the same parts in the second embodiment.

The RFID tags 22a to 22t are an example of information recording media on which information (to be referred to as magnetic field determination information) for determining a magnetic field strength of the magnetic field generating apparatus 33 brought close to a proximity position represented by the position indication sheet 22 is recorded. More specifically, the RFID tags 22a to 22t, for example, are arranged near the markers M1 to M18, respectively, and store pieces of magnetic field determination information for determining magnetic field strengths of proximity positions of the magnetic field generator 33a brought close to the markers M1 to M18, respectively. The pieces of magnetic field determination information of the RFID tags 22a to 22t are read by the read unit 33d of the magnetic field generator 33a.

The RFID tags 22a to 22t are arranged for proximity positions even when the supine position marker group MG1, the left lateral decubitus position marker group MG2, and the right lateral decubitus position marker group MG3 have markers different from each other. As the pieces of magnetic field determination information recorded on the RFID tags 22a to 22t, information representing a value of a drive current to be supplied to the magnetic field generator 33a, patient information of the subject 100, and information representing a body position, for determining a drive electric power to be supplied to the magnetic field generator 33a are illustrated.

Figure 15:
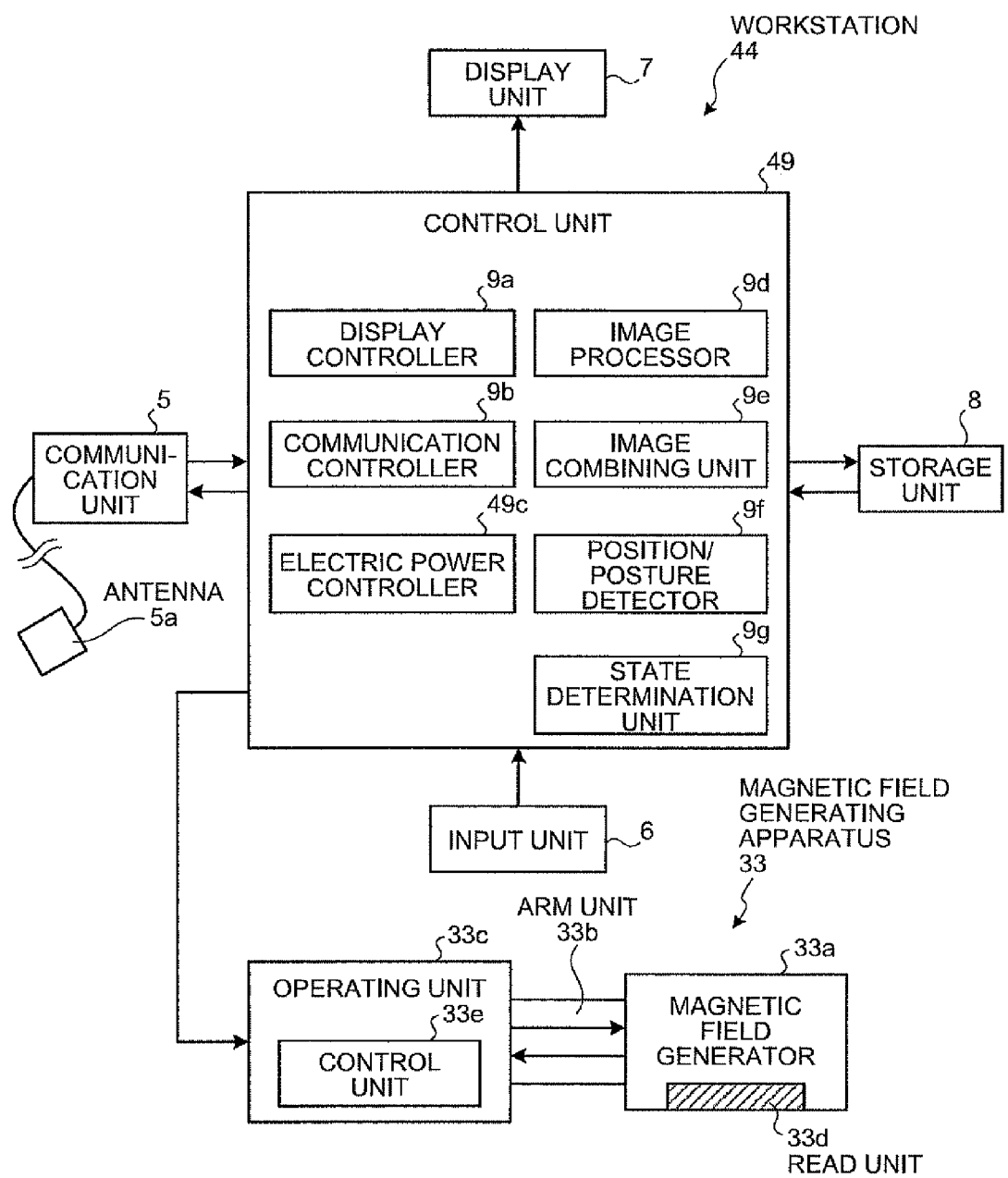
FIG. 15 is a block diagram typically showing one configuration of a magnetic field generating apparatus and a workstation according to the second embodiment.

Configurations of the magnetic field generating apparatus 33 and the workstation 44 will be described below in detail. FIG. 15 is a block diagram typically showing one configuration of the magnetic field generating apparatus 33 and the workstation 44. As shown in FIG. 15, the magnetic field generating apparatus 33, as described above, has the magnetic field generator 33a, the arm unit 33b, the operating unit 33c, the read unit 33d, and the control unit 33e. On the other hand, the workstation 44 has a control unit 49 in place of the control unit 9 of the workstation 4 of the body-insertable apparatus system according to the first embodiment. The control unit 49 has a power controller 49c in place of the magnet selector 9c of the control unit 9 of the workstation 4. Other configurations are the same as those in the first embodiment, and the same reference numerals as in the first embodiment denote the same parts in the second embodiment.

The magnetic field generator 33a is for generating a magnetic field for controlling motion of the capsule endoscope 1 in the liquid Lq1 inserted into the gastrointestinal tract of the subject 100. More specifically, the magnetic field generator 33a is realized by using an electromagnet, and the magnetic field generator 33a generates a magnetic field on the basis of a drive electric power supplied from the operating unit 33c through the arm unit 33b. In this case, the magnetic field generator 33a is brought close to a proximity position represented by the position indication sheet 22, and the magnetic field generator 33a controls at least one of the position and the posture of the capsule endoscope 1 floated on the surface of, for example, the liquid Lq1 by the magnetic field generated based on the drive electric power.

The magnetic field generator 33a has the read unit 33d as described above. The read unit 33d is for reading the pieces of magnetic field determination information recorded on the RFID tags 22a to 22t arranged on the position indication sheet 22. More specifically, when the magnetic field generator 33a is brought close to any one of the markers M1 to M18 of the position indication sheet 22, the read unit 33d reads the magnetic field determination information, through a predetermined radio wave, from the RFID tag (i.e., any one of the RFID tags 22a to 22t) arranged near the marker to which the magnetic field generator 33a is brought close. The read unit 33d transmits the read magnetic field determination information to the control unit 33e of the operating unit 33c.

The arm unit 33b has one end to which the magnetic field generator 33a is connected and the other end to which the operating unit 33c is connected. The arm unit 33b electrically connects the magnetic field generator 33a and the operating unit 33c to each other. In this case, the arm unit 33b electrically connects the electromagnet of the magnetic field generator 33a and the control unit 33e to each other and electrically connects the read unit 33d and the control unit 33e to each other.

The operating unit 33c is for operating the magnetic field generator 33a and the read unit 33d arranged at an end of the arm unit 33b. More specifically, the operating unit 33c is gripped by an examiner to adjust the positions of the magnetic field generator 33a and the read unit 33d to the position indication sheet 22 by an operation of the examiner. The operating unit 33c is supplied with a drive electric power from the control unit 49 of the workstation 44, and the operating unit 33c adjusts and supplies the drive electric power to the magnetic field generator 33a or the read unit 33d. The operating unit 33c has various operation switches (not shown) which operates starts or stops of drives of the magnetic field generator 33a and the read unit 33d. The magnetic field generator 33a further has the control unit 33e which controls drives of the magnetic field generator 33a and the read unit 33d on the basis of input information from the operation switch.

The control unit 33e controls the drive of the read unit 33d on the basis of the input information from the operation switch of the operating unit 33c, causes the read unit 33d to read the magnetic field determination information recorded on the marker (any one of the markers M1 to M18) at the proximity position to which the magnetic field generator 33a is brought close, and acquires the magnetic field determination information read by the read unit 33d. The control unit 33e controls the drive of the magnetic field generator 33a on the basis of the magnetic field determination information acquired as described above. More specifically, the control unit 33e acquires a drive electric power from the control unit 49 of the workstation 44 and adjusts the drive electric power from the control unit 49 on the basis of the magnetic field determination information. The control unit 33e supplies the adjusted drive electric power to the magnetic field generator 33a and causes the magnetic field generator 33a to generate a magnetic field based on the adjusted drive electric power. More specifically, the control unit 33e adjusts the drive electric power to the magnetic field generator 33a on the basis of the magnetic field determination information acquired from the read unit 33d. The drive electric power is adjusted as described above to control the magnetic field strength of the magnetic field generator 33a.

On the other hand, the control unit 49 of the workstation 44 has almost the same function as that of the control unit 9 of the workstation 4 and controls of the drive of the magnetic field generating apparatus 33. The control unit 49 further has the power controller 49c which controls a drive electric power supplied to the magnetic field generating apparatus 33. The power controller 49c controls the drive electric power supplied to the magnetic field generating apparatus 33 on the basis of a determination result of the magnetic field strength obtained by the state determination unit 9g. The power controller 49c supplies the drive electric power controlled as described above to the magnetic field generating apparatus 33. The drive electric power controlled by the power controller 49c is supplied to the control unit 33e through a cable or the like. In this case, the state determination unit 9g determines a magnetic field strength of the magnetic field generator 33a to the capsule endoscope 1 on the basis of the magnetic field detection signal received from the capsule endoscope 1.

Figure 16:
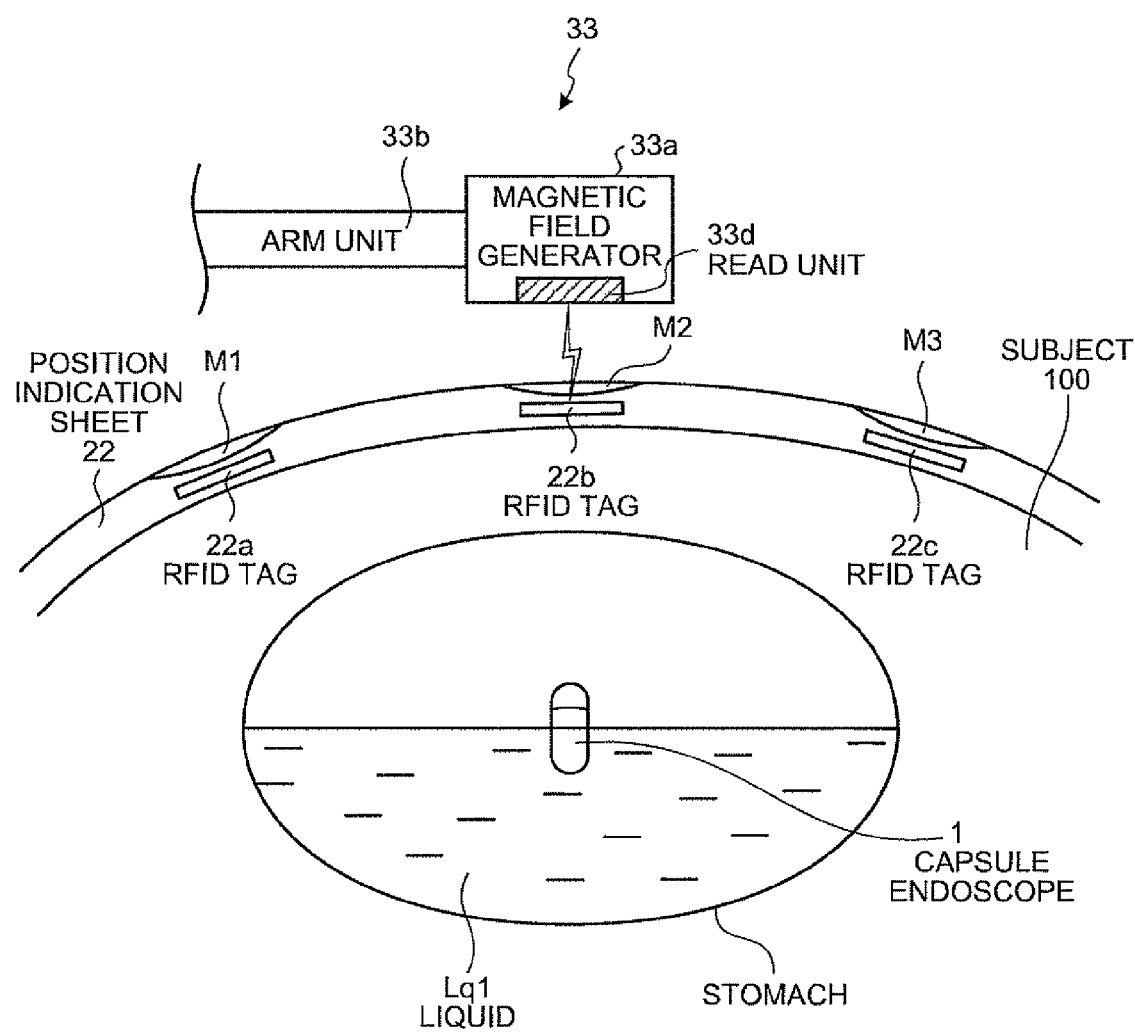
FIG. 16 is a block diagram for explaining an operation of the magnetic field generating apparatus which generates a magnetic field on the basis of magnetic field determination information read from an RFID tag at a proximity position.

The control unit 33e of the magnetic field generating apparatus 33 initially sets a drive electric power supplied to the magnetic field generator 33a on the basis of the magnetic field determination information. Thereafter, the drive electric power controlled by the power controller 49c is supplied to the magnetic field generator 33a and causes the magnetic field generator 33a to generate a magnetic field based on the drive electric power. FIG. 16 is a block diagram for explaining an operation of the magnetic field generating apparatus 33 which generates a magnetic field on the basis of magnetic field determination information read from an REID tag at a proximity position.

As shown in FIG. 16, when the magnetic field generator 33a is brought close to a proximity position represented by, for example, the marker M2, the control unit 33e of the magnetic field generating apparatus 33 controls the read unit 33d to read the magnetic field determination information from the RFID tag 22b arranged near the marker M2, and the control unit 33e acquires the magnetic field determination information read by the read unit 33d. In this case, the control unit 33e initially sets the drive electric power supplied to the magnetic field generator 33a brought close to the marker M2 on the basis of the acquired magnetic field determination information (for example, information representing a value of a drive electric current, patient information of the subject 100, or the like). The magnetic field generator 33a supplied with the initially set drive electric power applies a magnetic field of a magnetic field strength based on the initially set drive electric power to the capsule endoscope 1 in, for example, a stomach to control at least one of the position and the posture of the capsule endoscope 1 in the stomach.

Thereafter, when the control unit 33e is supplied with the drive electric power controlled by the power controller 49c from the control unit 49 of the workstation 44, the control unit 33e supplies the drive electric power controlled by the power controller 49c to the magnetic field generator 33a, and the control unit 33e causes the magnetic field generator 33a to generate a magnetic field of a magnetic field strength based on the drive electric power. In this case, the control unit 33e readjusts the initially set drive electric power on the basis of a designation of the power controller 49c. The control unit 33e controls the drive electric power with respect to all the proximity positions represented by the position indication sheet 22.

The magnetic field generator 33a supplied with the drive electric power can generate a magnetic field sufficient to move the capsule endoscope 1 inserted into the gastrointestinal tract of the subject 100 in the liquid Lq1. An examiner performs procedures subsequent to step S101 described above by using the magnetic field generating apparatus 33 to make it possible to enjoy the same functional effect as that of the first embodiment described above.

In the second embodiment of the invention, RFID tags on which pieces of magnetic field determination information are recorded are arranged near proximity positions of the position indication sheet 22, so that the read unit 33d of the magnetic field generating apparatus 33 reads the pieces of magnetic field determination information from the RFID tags at the proximity positions. However, the invention is not limited to the configuration. Optical information recording media on which the pieces of magnetic field strength information are recorded may be added to proximity positions on the position indication sheet 22, respectively, and the read unit 33d may emit a predetermined beam to the optical information recording media to optically read the optical information recording media. The shapes of markers on the position indication sheet 22 may be changed depending on magnetic field strengths, the shapes of the markers may be optically read by the read unit 33d, and the magnetic field strength of the magnetic field generator 33a may be determined on the basis of the read shapes of the markers.

In the second embodiment of the present invention, a magnetic field strength of the magnetic field generator 33a is initially determined on the basis of the magnetic field determination information read from the RFID tags arranged on the position indication sheet 22. However, the present invention is not limited to the configuration. Information such as a sign or a character representing a magnetic field strength or a current value may be added to each of the proximity positions of the position indication sheet 22, and the magnetic field strength of the magnetic field generator 33a may be manually operated by visually checking the information. In this case, in the operating unit 33c, an adjustment switch which adjusts a drive electric power supplied to the magnetic field generator 33a may be arranged.

The magnetic field strength of the magnetic field generator 33a may be controlled by the control unit 49 of the workstation 44. In this case, the power controller 49c may initially set the drive electric power supplied to the magnetic field generator 33a on the basis of the patient information or the like of the subject 100 input by, for example, the input unit 6, and the control unit 49 may supply the drive electric power initially set by the power controller 49c to the magnetic field generating apparatus 33.

As described above, in the second embodiment of the invention, an electromagnet is brought close to the position indication sheet in place of a permanent magnet, and at least one of the position and the posture of the capsule endoscope according to the first embodiment described above is controlled by a magnetic field of the electromagnet. For this reason, the functional effect of the first embodiment can be enjoyed, and the magnetic field of the electromagnet applied to the capsule endoscope in the gastrointestinal tract can be easily adjusted, and motion of the capsule endoscope in the gastrointestinal tract in the liquid can be more easily operated.

The position indication sheet has pieces of magnetic field determination information for proximity positions. Each time the electromagnet is brought close to the proximity position, the pieces of magnetic field determination information at the proximity positions are read, and the magnetic field strength of the electromagnet is controlled on the basis of the pieces of magnetic field determination information. For this reason, the magnetic field of the electromagnet can be reliably applied to the capsule endoscope in the stomach, and at least one of the position and the posture of the capsule endoscope can be reliably controlled by the magnetic field. In the second embodiment, a current flowing in the electromagnet is controlled to change the strength of a magnetic field to be generated. However, the invention is not limited to the configuration. The strength of a magnetic field (magnetic field of the permanent magnet generated to a subject) may be changed by changing a distance between the permanent magnet and the subject. Although not shown, a mechanism (distance changing unit) which changes a distance between the permanent magnet and the subject may be arranged.

A third embodiment of the present invention will be described below. In the first embodiment described above, one antenna 5a is connected to the workstation 4, and the capsule endoscope 1 and the workstation 4 transmit and receive a radio signal through the antenna 5a. However, in the third embodiment, a plurality of antennas are connected to a workstation, and the capsule endoscope 1 and the workstation transmit and receive a radio signal through any one of the plurality of antennas.

Figure 17:
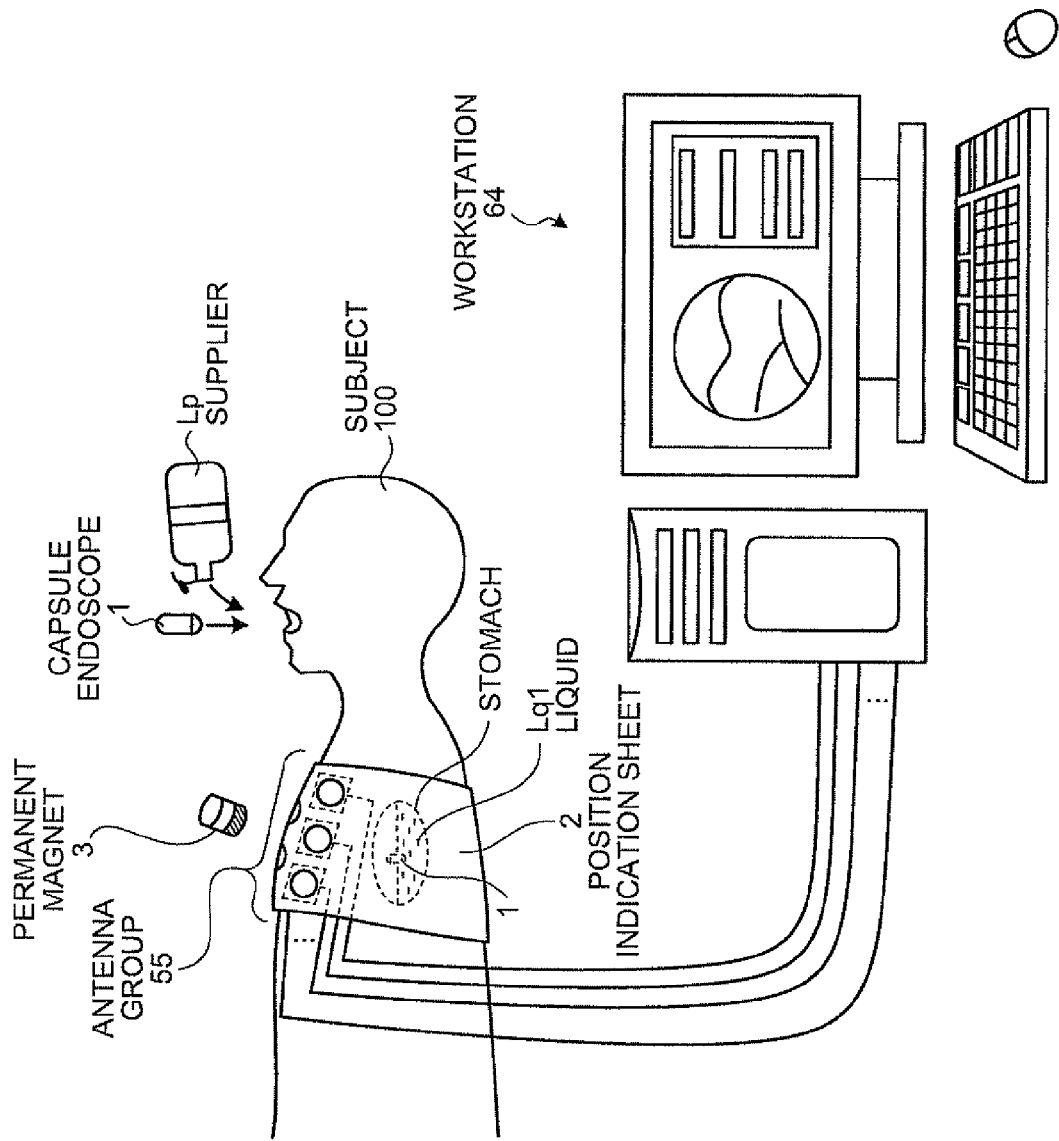
FIG. 17 is a schematic diagram showing one configuration of a body-insertable apparatus system according to the third embodiment of the invention.

FIG. 17 is a schematic diagram showing one configuration of a body-insertable apparatus system according to the third embodiment of the invention. As shown in FIG. 17, the body-insertable apparatus system according to the third embodiment has a workstation 64 in place of the workstation 4 of the body-insertable apparatus system according to the first embodiment. The workstation 64 has an antenna group 55 in place of one antenna 5a connected to the workstation 4 according to the first embodiment described above. Other configurations are the same as those in the first embodiment, and the same reference numerals as in the first embodiment denote the same parts in the third embodiment.

The antenna group 55 is for transmitting and receiving a radio signal between the capsule endoscope 1 inserted into a gastrointestinal tract of the subject 100 and the workstation 64. More specifically, antennas included in the antenna group 55 are arranged on the position indication sheet 2 in association with proximity positions represented by the position indication sheet 2, and the antennas are electrically connected to the workstation 64 through the cable or the like. At least one of the antennas included in the antenna group 55 supersensitively transmits and receives a radio signal to/from the capsule endoscope 1 inserted into the gastrointestinal tract of the subject 100 and the capsule endoscope 1, and the antenna can supersensitively receive an image signal or the like from the capsule endoscope 1.

Figure 18:
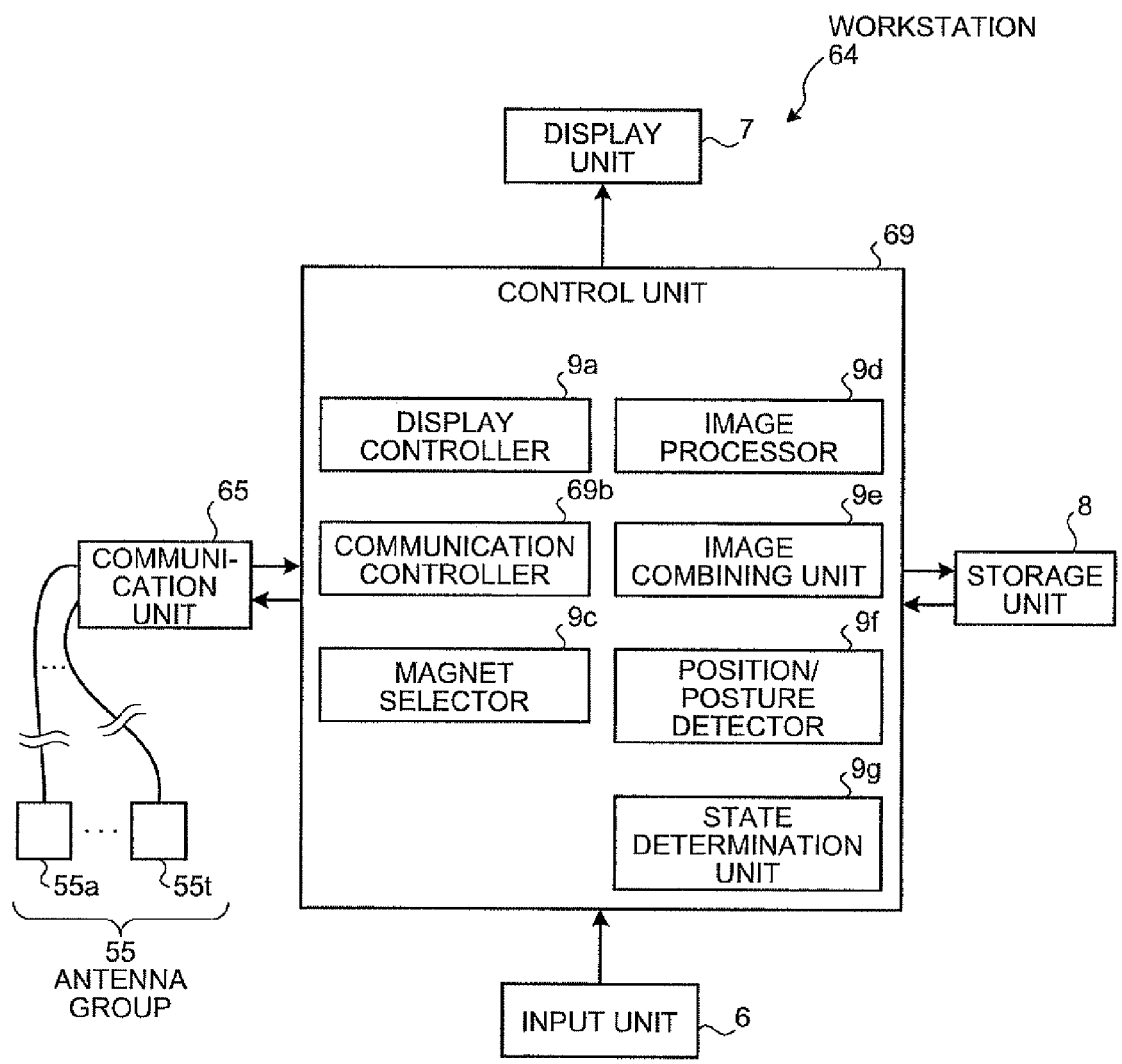
FIG. 18 is a block diagram typically showing one configuration of a workstation according to the third embodiment.

A configuration of the workstation 64 according to the third embodiment will be described below in detail. FIG. 18 is a block diagram typically showing one configuration of the workstation 64 according to the third embodiment. As shown in FIG. 18, the workstation 64 according to the third embodiment has a communication unit 65 in place of the communication unit 5 of the workstation 4 of the body-insertable apparatus system according to the first embodiment described above and has a control unit 69 in place of the control unit 9. The control unit 69 has a communication controller 69b in place of the communication controller 9b of the control unit 9 of the workstation 4. Other configurations are the same as those in the first embodiment, and the same reference numerals as in the first embodiment denote the same parts in the third embodiment.

The communication unit 65 is for performing radio communication with the capsule endoscope 1 and the workstation 64 by using the antenna group 55. More specifically, the antennas (for example, 18 antennas 55a to 55t corresponding to the markers M1 to M18 on the position indication sheet 2) of the antenna group 55 are connected to the communication unit 65 through a cable or the like. The communication unit 65 performs a predetermined demodulating process to a radio signal received through any one of the antennas included in the antenna group 55 to acquire various pieces of information transmitted from the capsule endoscope 1. In this case, the communication unit 65 compares received electric-field strengths of the antennas included in the antenna group 55 with each other, and the communication unit 65 receives a radio signal through an antenna having the highest received electric-field strength and selected from the antenna group 55. The communication unit 65 can supersensitively receive the radio signal from the capsule endoscope 1 through the antenna having the highest received electric-field strength. Thereafter, the communication unit 65 acquires image information obtained by the imaging unit 12 and motion information of the casing 10 in a low-noise state on the basis of the radio signal received from the capsule endoscope 1 and transmits the acquired image information and the motion information in a low noise state to the control unit 69. The communication unit 65 acquires a magnetic field detection signal corresponding to a detection result of the magnetic field strength obtained by the magnetic sensor 15 in a low-noise state and transmits the acquired magnetic field detection signal in the low-noise state to the control unit 69.

The communication unit 65 performs a predetermined modulating process or the like to a control signal to the capsule endoscope 1 received from the control unit 69 and modulates the control signal into a radio signal. In this case, the communication unit 65 transmits predetermined test signals from all the antennas of, for example, the antenna group 55 and transmits an ACK signal corresponding to the test signal to the capsule endoscope 1. The communication unit 65 compares received electric-field strengths of the antennas when an ACK signal is received from the capsule endoscope 1 and transmits a radio signal to an antenna having the highest received electric-field strength and selected from the antenna group 55. In this manner, the communication unit 65 transmits a radio signal to the capsule endoscope 1 through the antenna having the highest electric-field strength selected from the antenna group 55. As described above, the communication unit 65 can reliably transmits a control signal which designates the start of drive of the imaging unit 12 to the capsule endoscope 1.

The control unit 69 has almost the same function as that of the control unit 9 of the workstation 4 and control the drive of the communication unit 65 to which the communication unit 5 is connected. The control unit 69 further has a communication controller 69b which controls the drive of the communication unit 65 in place of the communication unit 5 which performs radio communication by using one antenna 5a described above. The communication controller 69b, as described above, controls the drive of the communication unit 65 to receive a radio signal from the capsule endoscope 1 through the antenna having the highest received electric-field strength, and the communication controller 69b acquires the image information or the motion information from the communication unit 65 in a low-noise state. In addition, the communication controller 69b acquires a magnetic field detection signal in a low-noise state from the communication unit 65. The communication controller 69b transmits the control signal to the capsule endoscope 1 to the communication unit 65 to cause the communication unit 65 to generate a radio signal including the control signal. As described above, the drive of the communication unit 65 is controlled to transmit the radio signal through the antenna having the highest received electric-field strength.

Figure 19:
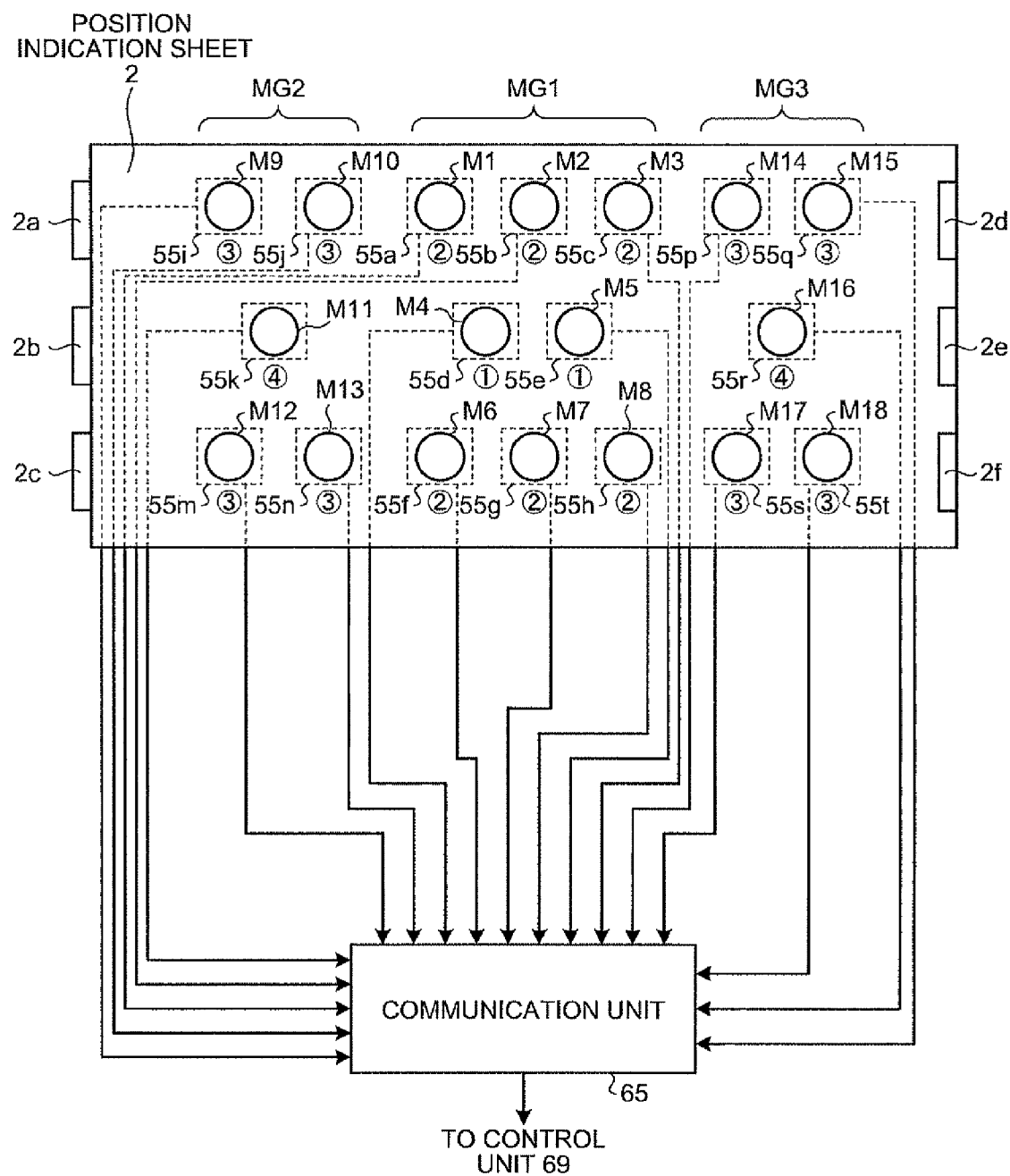
FIG. 19 is a schematic diagram illustrating an arrangement state of an antenna group arranged on the position indication sheet in association with a plurality of proximity positions.

An arrangement of the antennas of the antenna group 55 to the position indication sheet 2 will be described below. FIG. 19 is a schematic diagram illustrating an arrangement state of the antenna group 55 arranged on the position indication sheet 2 in association with a plurality of proximity positions. As shown in FIG. 19, the antennas of the antenna group 55 are arranged on the position indication sheet 2 in association with the plurality of proximity positions represented by the position indication sheet 2. More specifically, for example, 18 antennas 55a to 55t of the antenna group 55 are arranged on the position indication sheet 2 in association with 18 proximity positions represented by markers M1 to M18 formed on, for example, the position indication sheet 2. In this case, the antennas 55a to 55t are arranged near, for example, the markers M1 to M18, respectively. The antennas 55a to 55t are connected to the communication unit 65 of the workstation 64 through a cable or the like. The communication unit 65 is, as described above, connected to the control unit 69 of the workstation 64.

In this case, the antennas 55a to 55t arranged on the position indication sheet 2 in association with the proximity positions transmit and receive radio signals to/from the capsule endoscope 1 inserted into the gastrointestinal tract of the subject 100. In this case, at least one of the antennas 55a to 55t supersensitively transmit and receive a radio signal to/from the capsule endoscope 1 captured by a magnetism of, for example, the permanent magnet 3 brought close to the proximity position represented by the position indication sheet 2. More specifically, when the antennas 55a to 55t are arranged on the position indication sheet 2 in association with the proximity positions, the antennas 55a to 55t are arranged at predetermined relative positions to capture positions of the capsule endoscope 1 captured by the magnetism of, for example, the permanent magnet 3 brought close to the proximity positions. Relative positional relationships between the antennas 55a to 55t and the capsule endoscope 1 at the capture positions are positional relationships in which at least one of the antennas 55a to 55t and the capsule endoscope 1 can supersensitively transmit and receive a radio signal from/to each other.

Figure 20:
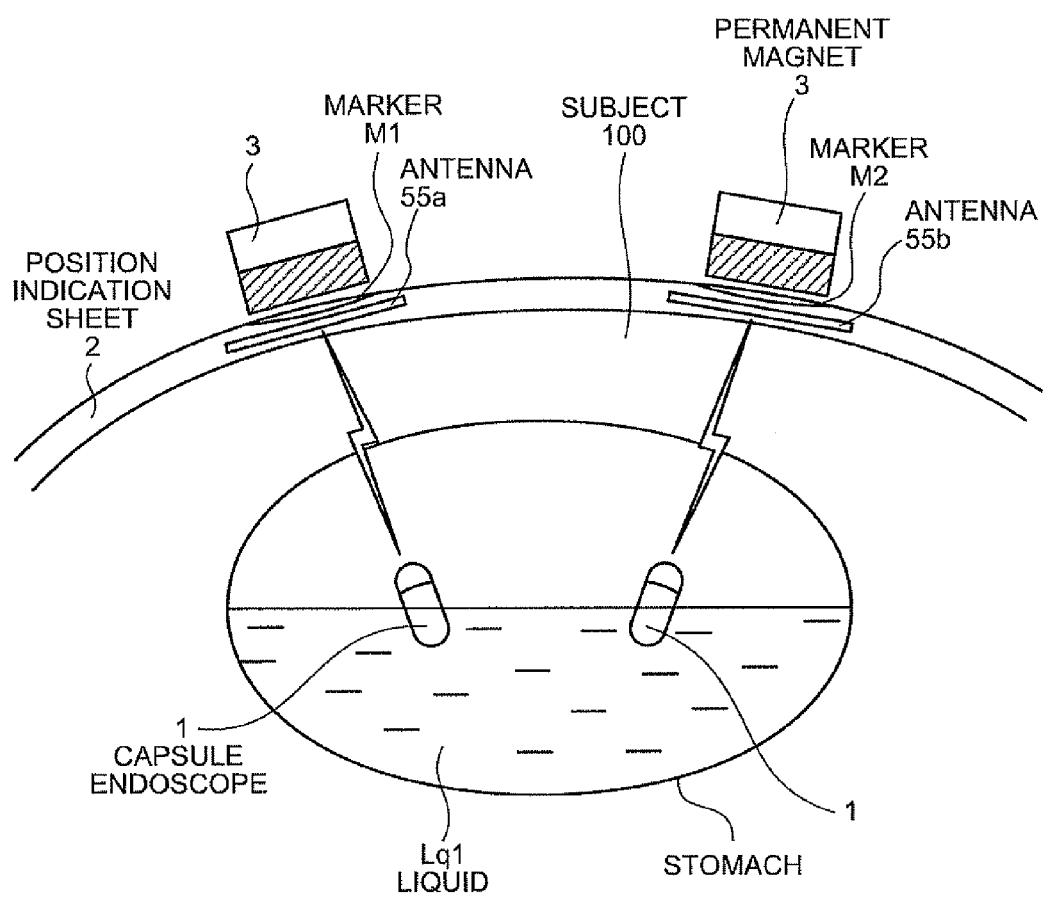
FIG. 20 is a schematic diagram illustrating a state in which the antennas arranged on the position indication sheet in accordance with the proximity positions and a capsule endoscope transmit and receive a radio signal.

More specifically, when the permanent magnet 3 is brought close to the proximity position represented by the marker M1, for example, as shown in FIG. 20, the capsule endoscope 1 in the stomach of the subject 100 is captured by the magnetism of the permanent magnet 3 brought close to the marker M1. In this case, the capsule endoscope 1 is captured at a predetermined relative position to the antenna 55a arranged in association with the proximity position. The capsule endoscope 1 captured at the relative position can supersensitively transmit and receive a radio signal to/from the antenna 55a. Similarly, when the permanent magnet 3 is brought close to the proximity position represented by the marker M2, the capsule endoscope 1 in the stomach is captured by the magnetism of the permanent magnet 3 brought close to the marker M2. In this case, the capsule endoscope 1 is captured at a predetermined relative position to the antenna 55b in association with the proximity position. The capsule endoscope 1 captured at the relative position can supersensitively transmit and receive a radio signal to/from the antenna 55b. As described above, with respect to all the antennas 55a to 55t arranged on the position indication sheet 2 in association with the proximity positions, the same functional effect can be enjoyed.

In the third embodiment of the present invention, the antennas of the antenna group 55 are arranged in such a mode the antennas are overlapped on the markers of the position indication sheet 2. However, the invention is not limited to the configuration. The antennas of the antenna group 55 may be arranged on the position indication sheet 2 in association with the proximity positions, respectively. More specifically, when the antennas are arranged at relative positions at which a radio signal can be supersensitively transmitted and received to/from the capsule endoscope captured by a magnetism, the antennas may be arranged at any region on the position indication sheet 2. In this case, the arrangement positions of the antennas of the antenna group 55 can be set on the basis of an experiment result or the like. The number of antennas included in the antenna group 55 only has to be equal to the number of proximity positions represented by the position indication sheet 2. The number of antennas are not limited to 18.

As described above, the third embodiment of the invention has almost the same configuration as that of the first embodiment, a plurality of antennas are arranged on a position indication sheet in association with a plurality of proximity positions. When the capsule endoscope inserted into the gastrointestinal tract of the subject is captured by a magnetism, any one of the plurality of antennas is located at a position where the radio signal can be supersensitively transmitted and received between the antenna and the captured capsule endoscope. For this reason, the radio signal can be supersensitively received from the capsule endoscope through any one of the plurality of antennas, the functional effect of the first embodiment described above can be enjoyed, and an image of the inside of the gastrointestinal tract imaged by the capsule endoscope can be always acquired at a low-nose state.

By using the body-insertable apparatus system according to the third embodiment, an examiner can always display an image of the inside of the gastrointestinal tract on a display in a low-noise state, and the inside of the subject can be more easily observed by using the low-noise image.

A fourth embodiment of the present invention will be described below. In the first embodiment described above, at least one of the position and the posture of the capsule endoscope 1 inserted into a gastrointestinal tract is controlled by a magnetism. However, in the fourth embodiment, furthermore, the capsule endoscope 1 is brought close to a desired designated position such as an affected area or the like in the gastrointestinal tract to pick an enlarged image of the designated position.

Figure 21:
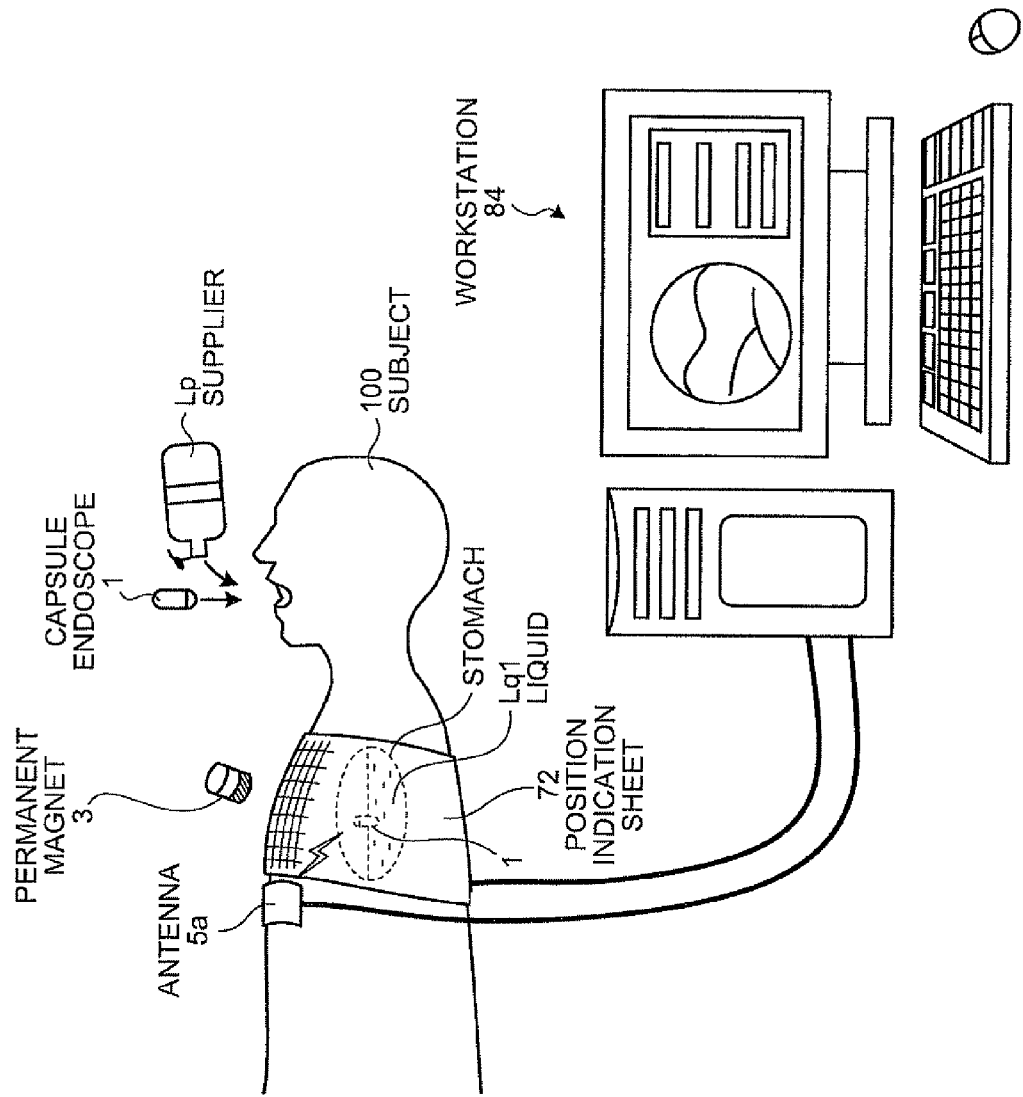
FIG. 21 is a schematic diagram showing one configuration of a body-insertable apparatus system according to a fourth embodiment of the present invention.

FIG. 21 is a schematic diagram showing one configuration of the body-insertable apparatus system according to the fourth embodiment of the invention. As shown in FIG. 21, the body-insertable apparatus system according to the fourth embodiment has a position indication sheet 72 in place of the position indication sheet 2 of the body-insertable apparatus system according to the first embodiment described above and has a workstation 84 in place of the workstation 4. Other configurations are the same as those of the first embodiment, and the same reference numerals as in the first embodiment denote the same parts in the fourth embodiment.

Figure 22:
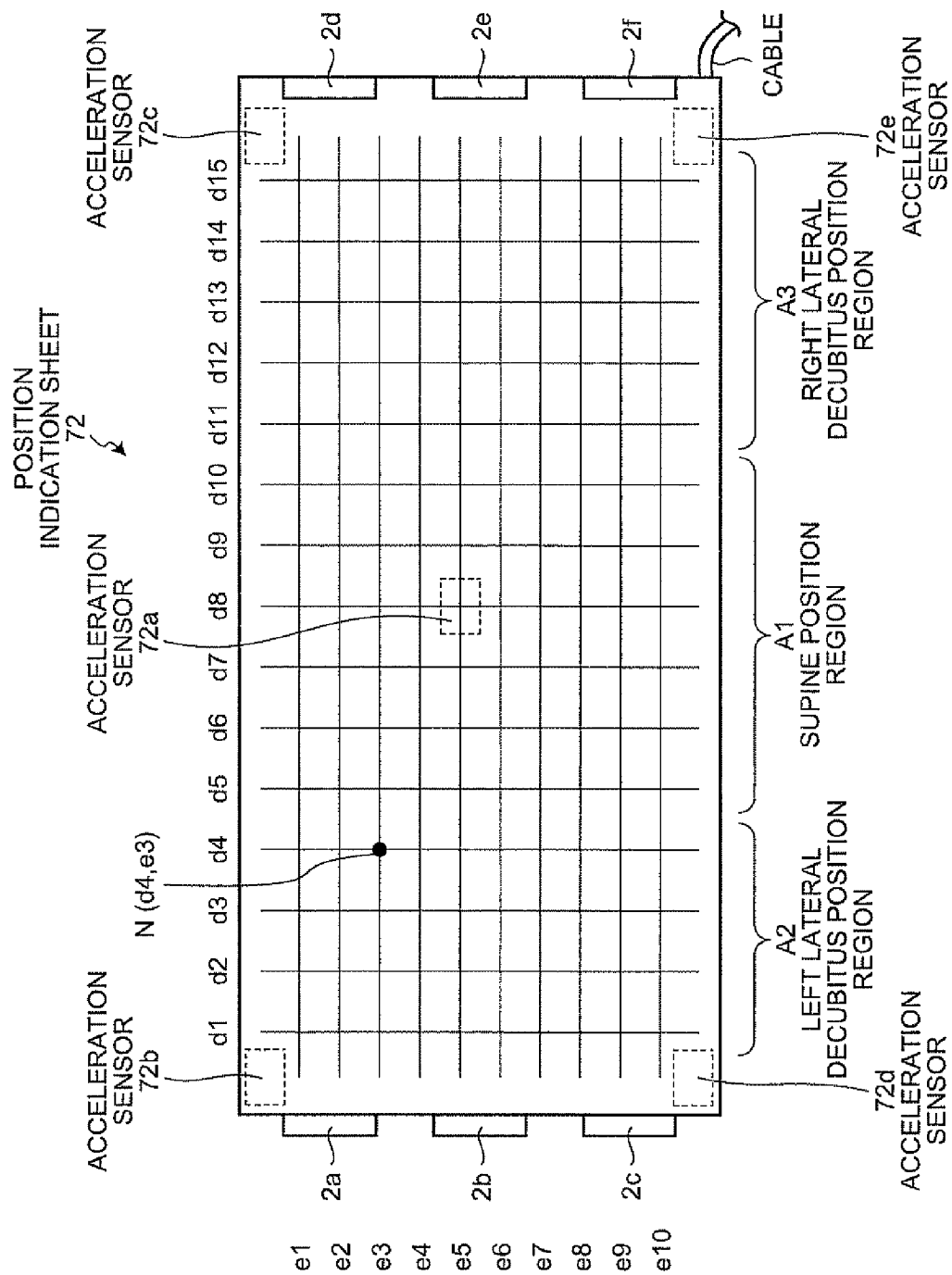
FIG. 22 is a schematic diagram showing one configuration of a position indication sheet according to the fourth embodiment.

A configuration of the position indication sheet 72 according to the fourth embodiment will be described below in detail. FIG. 22 is a schematic diagram showing one configuration of the position indication sheet 72 according to the fourth embodiment. As shown in FIG. 22, on the position indication sheet 72, a plurality of vertical lines d1 to d15 and a plurality of horizontal lines e1 to e10 are formed in place of the markers M1 to M18 on the position indication sheet 2 according to the first embodiment described above. The position indication sheet 72 further has a plurality of acceleration sensors 72a to 72e. Other configurations are the same as those of the first embodiment, and the same reference numerals as in the first embodiment denote the same parts in the first embodiment.

The vertical lines d1 to d15 and the horizontal lines e1 to e10 formed on the position indication sheet 72 are for showing the plurality of proximity positions to an examiner. More specifically, the vertical lines d1 to d15 and the horizontal lines e1 to e10 are formed in, for example, the form of a grid, and proximity positions are represented by intersection points, respectively. In this case, for example, a proximity position N shown in FIG. 22 is represented by an intersection point between the vertical line d4 and the horizontal line e3. The proximity position N is specified by coordinates (d4,e3) of a coordinate system formed by the vertical lines d1 to d15 and the horizontal lines e1 to e10. Each of the numbers of vertical lines and horizontal lines formed on the position indication sheet 72 may be one or more, and the numbers are not especially limited to 10 or 15.

The position indication sheet 72 is divided into, for example, an supine position region A1, a left lateral decubitus position region A2, and a right lateral decubitus position region A3 corresponding to the body position of the subject 100. In this case, the supine position region A1 is a region representing a proximity position in the subject 100 in a supine position. For example, the proximity positions are represented by the intersection points between the vertical lines d5 to d10 and the horizontal lines e1 to e10. The left lateral decubitus position region A2 is a region representing a proximity position in the subject 100 in the left lateral decubitus position. For example, proximity positions are represented by the intersection points between the vertical lines d1 to d4 and the horizontal lines e1 to e10. The right lateral decubitus position region A3 is a region representing a proximity position in the subject 100 in the right lateral decubitus position. For example, the proximity positions are represented by the intersection points between the vertical lines d11 to d15 and the horizontal lines e1 to e10. When the body position of the subject 100 to which the position indication sheet 72 is attached is a supine position, an examiner brings the permanent magnet 3 close to the proximity positions represented by the intersection points in the supine position region A1. When the body position of the subject 100 is a left lateral decubitus position, the examiner brings the permanent magnet 3 close to the proximity positions represented by the intersection points in the left lateral decubitus position region A2. When the body position of the subject 100 is a right lateral decubitus position, the examiner brings the permanent magnet 3 close to the proximity positions represented by the intersection points in the right lateral decubitus position region A3. The permanent magnet 3 brought close to the proximity positions as described above controls, as in the case in the first embodiment described above, at least one of the position and the posture of the capsule endoscope 1 inserted into the gastrointestinal tract of the subject 100.

Furthermore, the position indication sheet 72, as described above, has the plurality of acceleration sensors 72*a* to 72*e*. More specifically, the acceleration sensor 72*a* is fixedly arranged near the center of the position indication sheet 72, for example, a proximity position specified by coordinates (d8,e5). Furthermore, the acceleration sensors 72*b* to 72*e* are fixedly arranged at the four corners of the position indication sheet 72, respectively. The acceleration sensors 72*a* to 72*e* are electrically connected to the workstation 84 through a cable or the like. The acceleration sensors 72*b* to 72*e* detect accelerations when the position indication sheet 72 is displaced in the spatial coordinate system xyz and transmit detection results of the accelerations to the workstation 84. More specifically, the acceleration sensor 72*a* detects an acceleration when a center portion of the position indication sheet 72 is displaced in the spatial coordinate system xyz, and the acceleration sensor 72*a* transmits a acceleration detection result of the center portion of the position indication sheet 2 to the workstation 84. The acceleration sensors 72*b* to 72*e* detect accelerations when the corners of the position indication sheet 72 are displaced in the spatial coordinate system xyz, and the acceleration sensors 72*b* to 72*e* transmit acceleration detection results of the corners of the position indication sheet 72 to the workstation 84. The plurality of acceleration sensors fixedly arranged on the position indication sheet 72 only has to be fixedly arranged at the four corners of the position indication sheet 72 and near the center portion of the position indication sheet 72. The number of positions is not limited to five.

Figure 23:
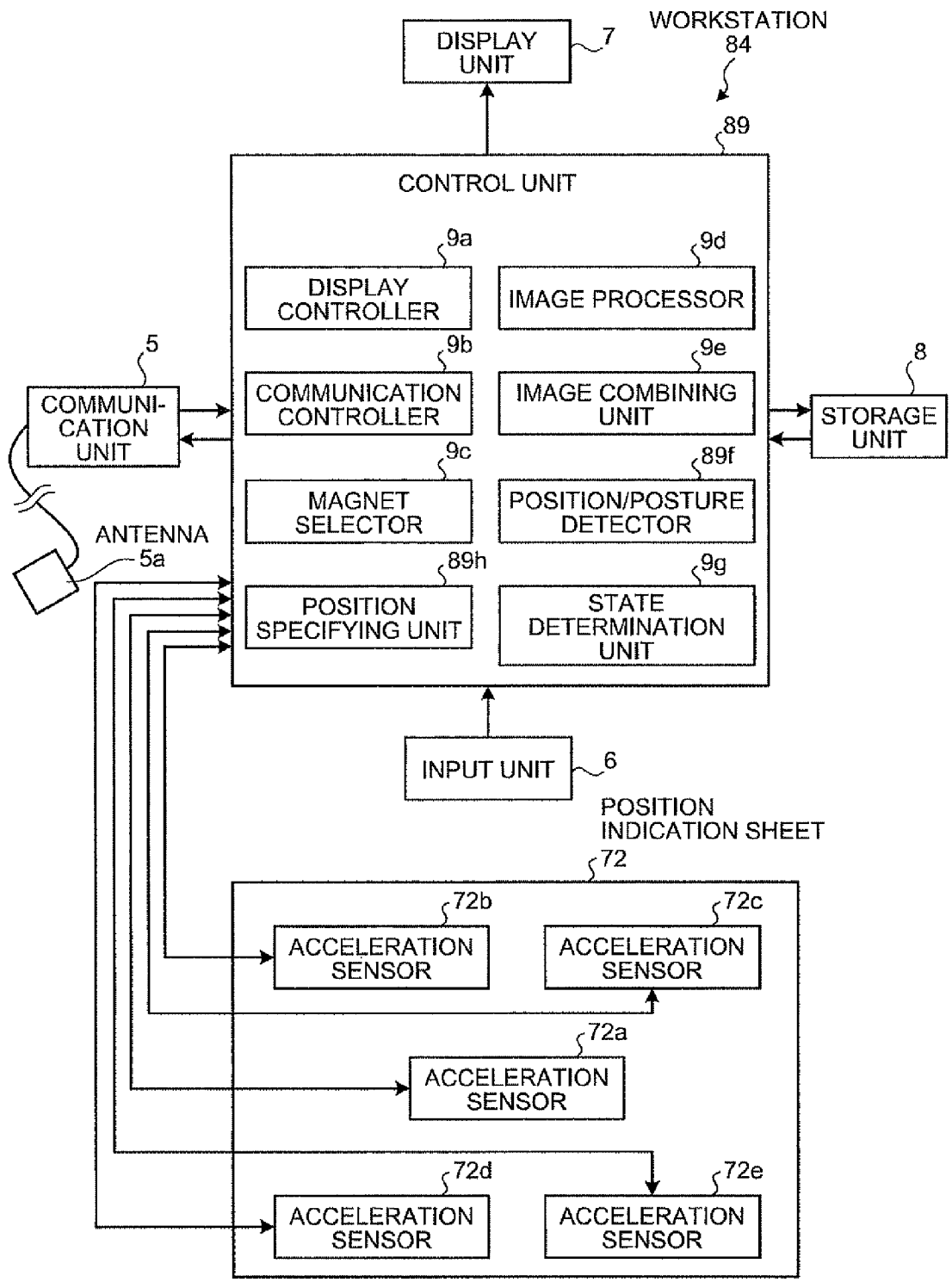
FIG. 23 is a block diagram typically showing one configuration of a workstation according to the fourth embodiment.

A configuration of the workstation 84 according to the fourth embodiment will be described below in detail. FIG. 23 is a block diagram typically showing one configuration of the workstation 84 according to the fourth embodiment of the invention. As shown in FIG. 23, the workstation 84 has a control unit 89 in place of the control unit 9 of the workstation 4 according to the first embodiment described above. The control unit 89 has a position/posture detector 89*f* in place of the position/posture detector 9*f* of the control unit 9 of the workstation 4, and the control unit 89 further has a position specifying unit 89*h*. The control unit 89 is electrically connected to the acceleration sensors 72*a* to 72*e* of the position indication sheet 72. Other configurations are the same as those in the first embodiment, and the same reference numerals as in the first embodiment denote the same parts in the fourth embodiment.

The control unit 89 has the same function as that of the control unit 9 of the workstation 4. The control unit 89 controls drives of the acceleration sensors 72*a* to 72*e* fixedly arranged on the position indication sheet 72. The control unit 89 further has a function of detecting a surface position of the position indication sheet 72 in the spatial coordinate system xyz, a function of specifying a proximity position corresponding to a desired designated position designated from an image of the inside of a gastrointestinal tract, and a function of showing the specific proximity position to an examiner. The control unit 89, as described above, has the position/posture detector 89*f* and the position specifying unit 89*h*.

The position/posture detector 89*f*, like the position/posture detector 9*f* of the workstation 4, detects a position and an posture of the capsule endoscope 1 in the spatial coordinate system xyz. Furthermore, the position/posture detector 89*f* detects a positional relationship between the capsule endoscope 1 and the position indication sheet 72 in the spatial coordinate system xyz. In this case, the position/posture detector 89*f* detects the surface position of the position indication sheet 72 in the spatial coordinate system xyz on the basis of acceleration detection results acquired from the acceleration sensors 72*a* to 72*e* described above.

More specifically, the position/posture detector 89*f* sets the spatial coordinate system xyz. In this case, the position indication sheet 72 is flatly arranged on the x-y plane of the spatial coordinate system xyz in a mode in which, for example, an original point O of the spatial coordinate system xyz is matched with the position of the acceleration sensor 72*a*. The capsule endoscope 1, as described above, is arranged at the original point O of the spatial coordinate system xyz in a mode in which, for example, a radial axis C2*b*, a major axis C1, and a radial axis C2*a* are matched with the x axis, the Y axis, and the z axis in the spatial coordinate system xyz, respectively. The position/posture detector 89*f* recognizes the petition and the posture of the capsule endoscope 1 arranged in the spatial coordinate system xyz and the surface position of the position indication sheet 72 as initial states, respectively. The position/posture detector 89*f* sequentially detects the positions and the postures of the capsule endoscope 1 which sequentially changes from the initial states and the surface position of the position indication sheet 72. In this case, the position/posture detector 89*f* sequentially detect the position and the posture of the capsule endoscope 1 at the present in the spatial coordinate system xyz on the basis of motion information of the capsule endoscope 1. The position/posture detector 89*f* sequentially calculates moving distances (vector quantities) of the center portion and the four corners of the position indication sheet 72 on the basis of the acceleration detection results acquired from the acceleration sensors 72*a* to 72*e*. The position/posture detector 89*f* sequentially detects surface positions of the position indication sheet 72 at the present in the spatial coordinate system xyz on the basis of the calculated moving distances. In this case, the position/posture detector 89*f* sequentially detects the surface positions of the position indication sheet 72 which repeats a change such as displacement or curvature from the initial states in the spatial coordinate system xyz.

The position/posture detector 89*f* sequentially detects present positional relationships between the capsule endoscope 1 and the position indication sheet 72 in the spatial coordinate system xyz on the basis of the position and the posture of the capsule endoscope 1 and the surface position of the position indication sheet 72 which are sequentially detected. Thereafter, the control unit 89 stores, as in the case of the first embodiment, the position/posture information of the capsule endoscope 1 in the storage unit 8, and the surface position of the position indication sheet 72 detected by the position/posture detector 89f is stored in the storage unit 8 in association with the position/posture information. The positional relationship between the capsule endoscope 1 and the position indication sheet 72 includes a relative position between the capsule endoscope 1 and the position indication sheet 72 in the spatial coordinate system xyz and the posture of the capsule endoscope 1 to a surface formed by the position indication sheet 72.

The position specifying unit 89h functions as a specifying unit which specifies a proximity position corresponding to a desired designated position designated in an image of the inside of the gastrointestinal tract imaged by the capsule endoscope 1. More specifically, the position specifying unit 89h acquires designated position information for designating a designated position in the image of the gastrointestinal tract from the input unit 6, and the position specifying unit 89h specifies a proximity position corresponding to the designated position from the plurality of proximity positions in the position indication sheet 72 on the basis of the positional relationship between the capsule endoscope 1 and the position indication sheet 72 and the designated position information. In this case, the input unit 6 functions as an input unit which inputs the designated position information of the desired position designated by an operation of an examiner in the image of the gastrointestinal tract displayed by the display unit 7 to the control unit 89.

Information representing the proximity position specified by the position specifying unit 89h is displayed on the display unit 7. In this case, when the position specifying unit 89h specifies a proximity position corresponding to the designated position, the display controller 9a displays information representing a specific proximity position in the position indication sheet 72 on the display unit 7. An examiner can easily find out the proximity position corresponding to the designated position in the plurality of proximity positions in the position indication sheet 72 on the basis of the information displayed on the display unit 7. In this case, the display unit 7 functions as a specific position display unit which represents the proximity position specified by the position specifying unit 89h.

Figure 24:
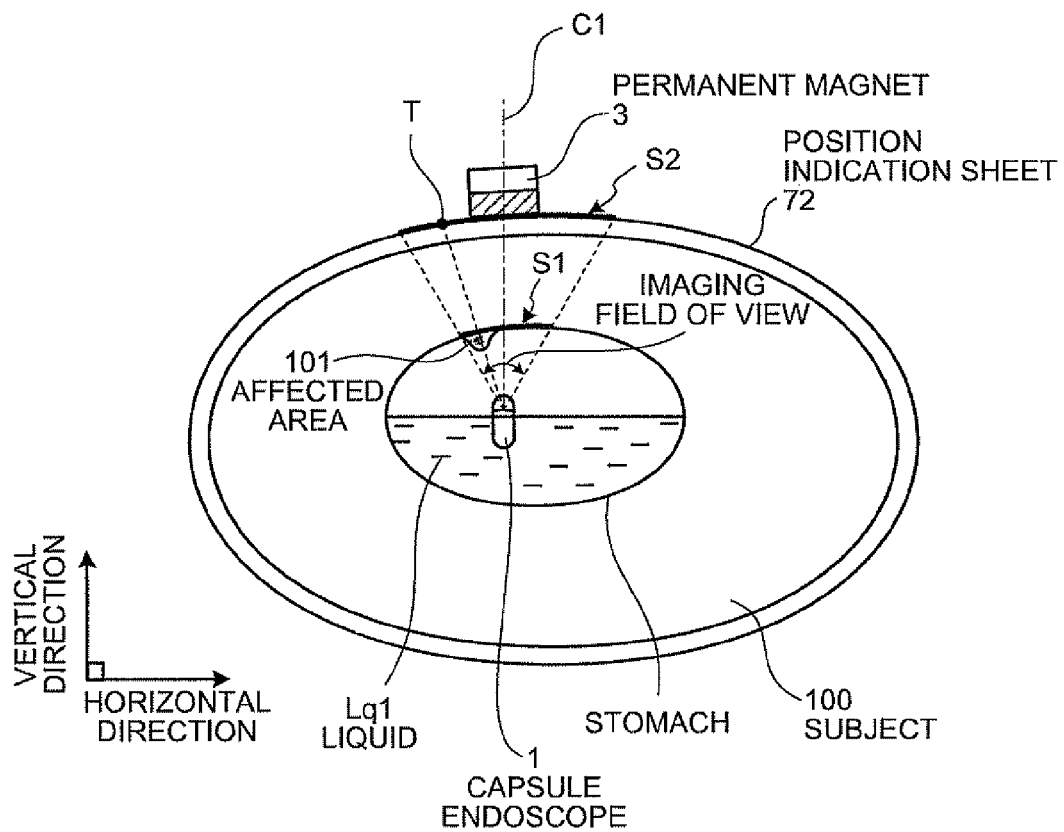
FIG. 24 is a schematic diagram illustrating a state in which a capsule endoscope in a stomach is captured by a magnetism of a permanent magnet brought close to a proximity position displayed on the position indication sheet.
Figure 25:
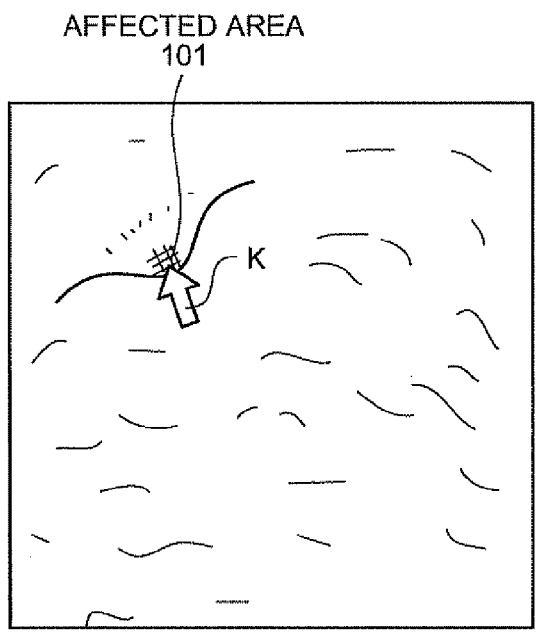
FIG. 25 is a schematic diagram illustrating an image of an inside of the stomach imaged by the capsule endoscope captured in the state shown in FIG. 24.
Figure 26:
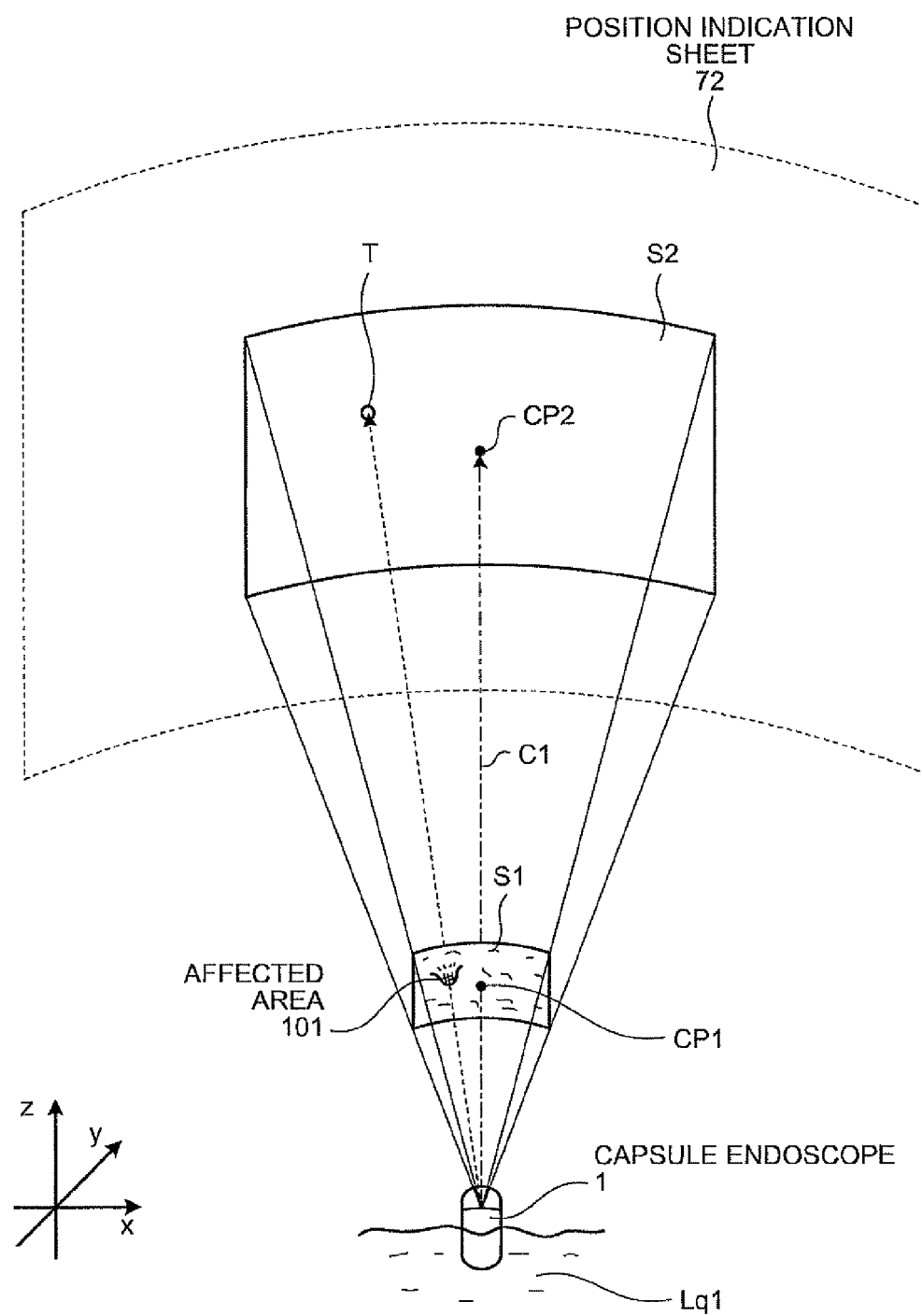
FIG. 26 is a schematic diagram for explaining an operation of a control unit which specifies a proximity position corresponding to a designated position from a plurality of proximity positions in the position indication sheet.

By illustrating a case in which the capsule endoscope 1 is inserted into the stomach of the subject 100, an operation of the control unit 89 which specifies a proximity position corresponding to a designated position in the image of the inside of the stomach imaged by the capsule endoscope 1 will be described below. FIG. 24 is a schematic diagram illustrating a state in which the capsule endoscope 1 in the stomach is captured by a magnetism of the permanent magnet 3 brought close to the proximity position displayed on the position indication sheet 72. FIG. 25 is a schematic diagram illustrating an image of the inside of the stomach imaged by the capsule endoscope 1 captured in the state shown in FIG. 24. FIG. 26 is a schematic diagram for explaining an operation of the control unit 89 which specifies a proximity position corresponding to a designated position from a plurality of proximity positions in the position indication sheet 72.

The examiner sequentially performs procedures in steps S101 to S106 described above. In this case, the capsule endoscope 1, for example, as shown in FIG. 24, is floated on the liquid Lq1 inserted into the stomach of the subject 100 and captured by a magnetism of the permanent magnet 3 brought close to the desired proximity position represented by the position indication sheet 72. The capsule endoscope 1 captured as described above sequentially picks images of the inside of the stomach while changing at least one of the position and the posture by the magnetism of the permanent magnet 3. In this case, the capsule endoscope 1 picks an image of, for example, the imaging region S1. This imaging region S1 is a partial region of a stomach wall falling within the imaging field of view of the capsule endoscope 1 and includes, for example, the affected area 101. In this manner, the capsule endoscope 1 picks the image of the inside of the stomach obtained by imaging the affected area 101 in the stomach. The image of the inside of the stomach, for example, as shown in FIG. 25, is displayed on the display unit 7 of the workstation 84.

The examiner, by using the input unit 6, performs an input operation for moving a cursor K to a desired position in the image of the inside of the stomach displayed on the display unit 7, for example, the position of the affected area 101 to designate a position of the affected area 101. In this case, the input unit 6 inputs designated position information for specifying a designated position of the affected area 101 to the control unit 89. When the control unit 89 receives the designated position information from the input unit 6, the control unit 89 specifies a proximity position corresponding to the position of the affected area 101 on the basis of the positional relationship between the capsule endoscope 1 and the position indication sheet 72 and the designated position information.

More specifically, the position/posture detector 89f detects a positional relationship between the capsule endoscope 1 which picks an image of the inside of the stomach and the position indication sheet 72 attached to the subject 100. In this case, the position specifying unit 89h detects a partial region S2 of the position indication sheet 72 illustrated in FIG. 24 on the basis of the positional relationship between the capsule endoscope 1 and the position indication sheet 72 detected by the position/posture detector 89f. The partial region S2 is a partial region of the position indication sheet 72 the range of which is determined by a field angle of the capsule endoscope 1. The partial region S2 is a partial region formed by projecting the imaging region S1 from the capsule endoscope 1 shown in FIG. 24 to the position indication sheet 72. More specifically, the imaging region S1 and partial region S2 have almost a similarity relation.

In this case, the position specifying unit 89h detects the relative positional relationship between a center point of the image of the inside of the stomach and the designated position of the affected area 101 on the basis of the designated position information of the affected area 101 input by the input unit 6. The relative positional relationship between the center point of the image and the designated position of the affected area 101 is almost the same as the relative positional relationship between a center point CP1 of the imaging region S1 shown in FIG. 26 and the affected area 101. The position specifying unit 89h, as shown in FIG. 26, detects a center point CP2 of the partial region S2 serving as an intersection point between the partial region S2 and the major axis C1 based on the position relation between the capsule endoscope 1 and the position indication sheet 72. The major axis C1, as described above, corresponds to a central axis of the imaging field of view of the capsule endoscope 1. For this reason, the two center points CP1 and CP2 are located on the major axis C1.

The position specifying unit 89h can specify a proximity position T corresponding to a designated position of the affected area 101 from the plurality of proximity positions in the partial region S2 which correlates with the imaging region S1 together with the positional relationship between the capsule endoscope 1 and the position indication sheet 72 and the designated position information of the affected area 101. In this case, a relative positional relationship between the center point CP2 and the proximity position T in the partial region S2 is almost the same as a relative positional relationship between the center point CP1 and the affected area 101 in the imaging region S1. More specifically, when the capsule endoscope 1 matches the central axis of the imaging field of view with the affected area 10, the affected area 101 and the proximity position T are located on the major axis C1 of the capsule endoscope 1.

When the position specifying unit 89h specifies the proximity position T corresponding to the designated position, the control unit 89 displays information representing the proximity position T specified by the position specifying unit 89h on the display unit 7. In this case, the display controller 9a displays information representing that the specified proximity position T is any one of the proximity positions in the position indication sheet 72 on the display unit 7. The examiner can easily find out the proximity position T corresponding to the designated position of, for example, the affected area 101 from the plurality of proximity positions in the position indication sheet 72 based on the information displayed on the display unit 7.

Figure 27:
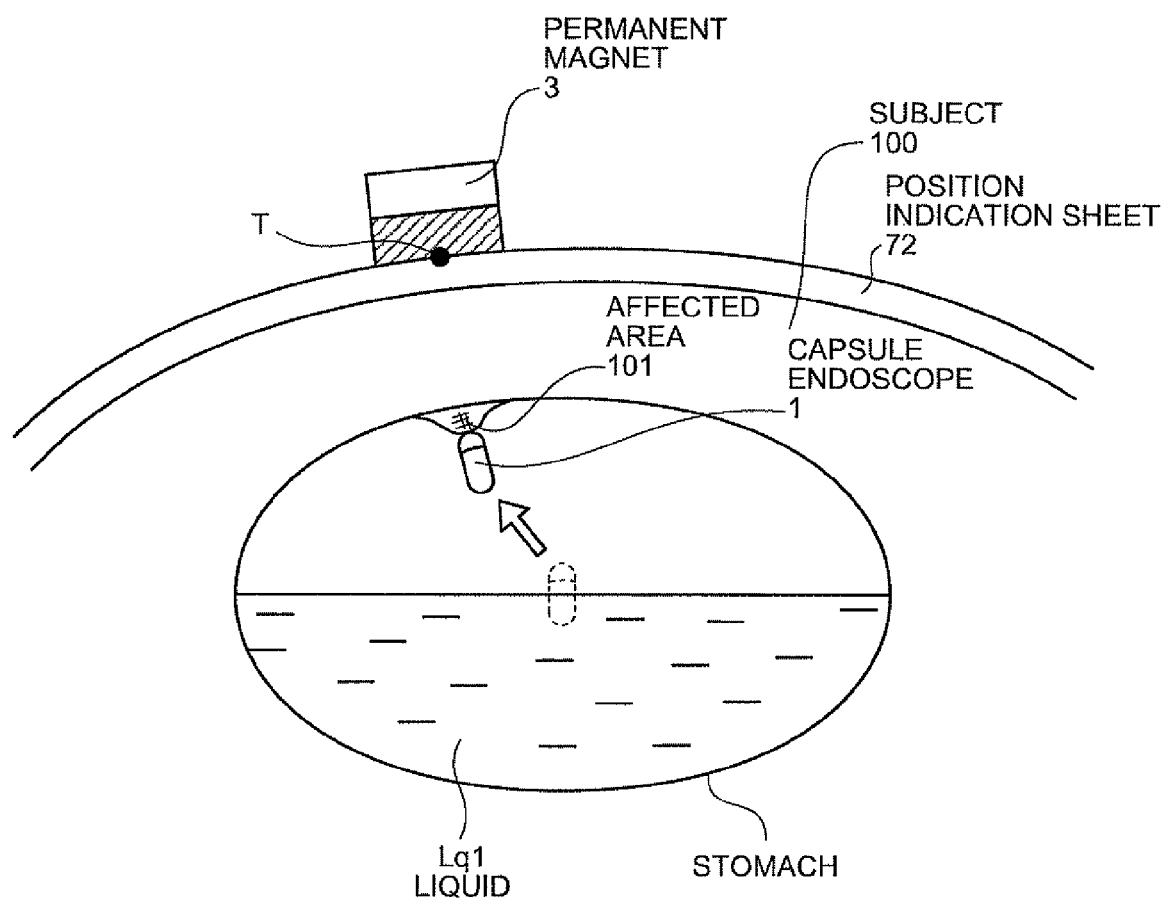
FIG. 27 is a schematic diagram illustrating a state in which the capsule endoscope is brought close to an affected area in the stomach.

Thereafter, the examiner brings the permanent magnet 3 close to the proximity position T displayed on the display unit 7 to make it possible to bring the capsule endoscope 1 in the stomach close to the affected area 101. FIG. 27 is a schematic diagram illustrating a state in which the capsule endoscope 1 is brought close to the affected area 101 in the stomach. As shown in FIG. 27, the permanent magnet 3 brought close to the proximity position T corresponding to the designated position of the affected area 101 generates a magnetic field to the capsule endoscope 1 in the stomach, and the capsule endoscope 1 is attracted to the affected area 101 by a magnetism of the magnetic field. The permanent magnet 3 is selected from, for example, a plurality of permanent magnets prepared in advance. In this manner, the permanent magnet 3 generates a sufficient magnetic field which attracts the capsule endoscope 1.

The capsule endoscope 1 applied with the magnetism of the permanent magnet 3 is brought close to the affected area 101 to be in contact with the affected area 101, and the capsule endoscope 1 picks an enlarged image of the affected area 101. The workstation 84 can display the enlarged image picked by the capsule endoscope 1 as described above on the display unit 7. The examiner visually checks the enlarged image displayed on the display unit 7 to make it possible to more exactly observe a desired position in the gastrointestinal tract such as the affected area 101.

The capsule endoscope 1 which can be in contact with the inner wall of the gastrointestinal tract further may include a special beam observing function which outputs a special beam, for example, an infrared ray to pick an image, and the enlarged image of the desired position such as the affected area 101 may be picked by the special beam. In this case, the capsule endoscope to which the special beam observing function is added switches the output beam into visible light obtained by an LED or the like or a special beam on the basis of a control signal from the workstation 84. The capsule endoscope 1 as described above may further include an extracting function which extracts a biological fluid, a biomedical tissue, or the like by using an extraction needle or the like which can be inserted into or pulled from the casing. In this case, the capsule endoscope 1 to which the extracting function is added extracts a biological fluid, a biomedical tissue, or the like in the gastrointestinal tract on the basis of the control signal from the workstation 84 when the capsule endoscope 1 is in contact with the inner wall of the gastrointestinal tract.

The capsule endoscope 1 as described above further includes a therapeutic function. As the therapeutic function, a function which cauterizes the biomedical tissue or the like by a heating probe which can be inserted into or pulled from, for example, the casing, a function which diffuses a medical agent or the like into the gastrointestinal tract, or a function which injects a medical agent into an affected area or the like by using an injection needle which can be inserted into or pulled from the casing may be used. In this case, the capsule endoscope 1 to which the therapeutic function is added starts a drive of the therapeutic function on the basis of a control signal from the workstation 84, for example, when the capsule endoscope 1 is in contact with the inner wall of the gastrointestinal tract.

Furthermore, the capsule endoscope 1 may additionally include a chemical or biochemical sensor for diagnosis. In this case, the capsule endoscope 1 brings the chemical or biochemical sensor for diagnosis into tight contact with a biomedical tissue in the gastrointestinal tract to make it possible to diagnose whether the biomedical tissue is a lesion. More specifically, the capsule endoscope 1 to which the chemical or biochemical sensor for diagnosis is added can detect a lesion from the biomedical tissue in the gastrointestinal tract.

In the fourth embodiment of the invention, information representing a proximity position specified in association with a desired designated position in an image is displayed on the display unit 7. However, the present invention is not limited to the configuration. Light-emitters such as LEDs or organic EL devices are arranged at a plurality of proximity positions represented by the position indication sheet 72, respectively. When the position specifying unit 89h specifies a proximity position corresponding to a designated position from the plurality of proximity positions, the control unit 89 may cause the light-emitter at the specified proximity position to emit light to show the proximity position to an examiner. In this case, the plurality of light-emitters arranged on the position indication sheet 72 are electrically connected to the control unit 89 through a cable or the like and driven and controlled by the control unit 89.

In the fourth embodiment of the present invention, a plurality of proximity positions are represented by the intersection points between the plurality of vertical lines and the plurality of horizontal lines formed on the position indication sheet 72. However, the present invention is not limited to this configuration. A plurality of proximity positions may be represented by a plurality of grids surrounded by the vertical lines and the horizontal lines, or, as in the case of the first embodiment, a plurality of markers may be formed on the position indication sheet 72 to show a plurality of proximity positions.

As described above, in the fourth embodiment of the invention, almost as in the first embodiment described above, a plurality of proximity positions are represented by a position indication sheet attached to a subject. Furthermore, when a desired designated position is designated in an image of the inside of the gastrointestinal tract imaged by the capsule endoscope inserted into the subject, a proximity position corresponding to the designated position is specified from the plurality of the proximity positions on the position indication sheet to represent the specified proximity position. For this reason, when, for example, a permanent magnet is brought close to the specified proximity position, the capsule endoscope 1 can be easily attracted to the designated position (for example, an affected area or the like) in a gastrointestinal tract by a magnetism of the permanent magnet, and further can be brought into contact with designated position in a gastrointestinal tract. As a result, an enlarged image of the designated position in the gastrointestinal tract, for example, an affected area can be picked by the capsule endoscope, the functional effect of the first embodiment described above can be enjoyed, and the enlarged image of the desired position in the gastrointestinal tract is visually checked to make it possible to more exactly observe the inside of the subject.

Figure 28:
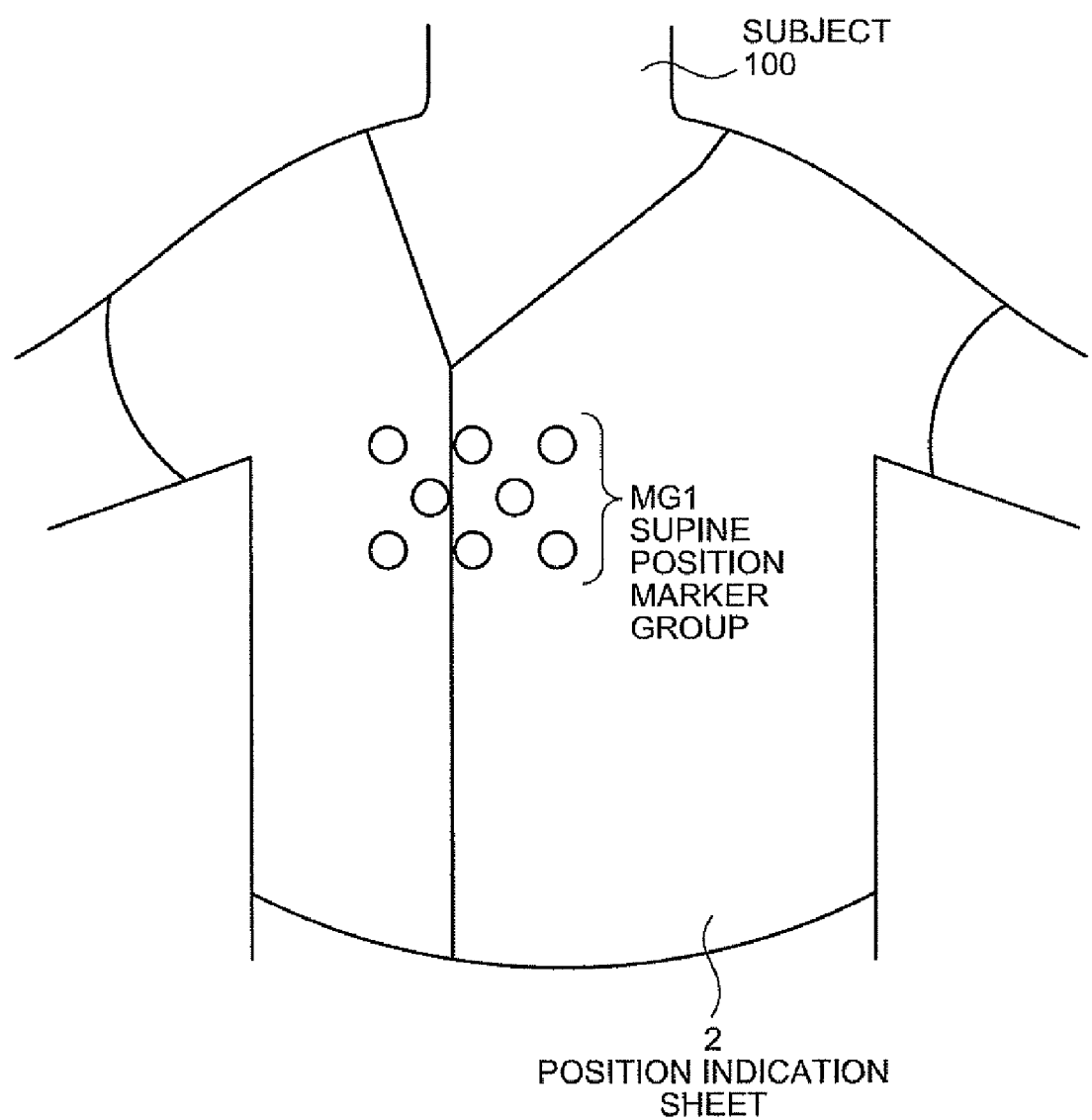
FIG. 28 is a schematic diagram illustrating a wearable position indication sheet.
Figure 29:
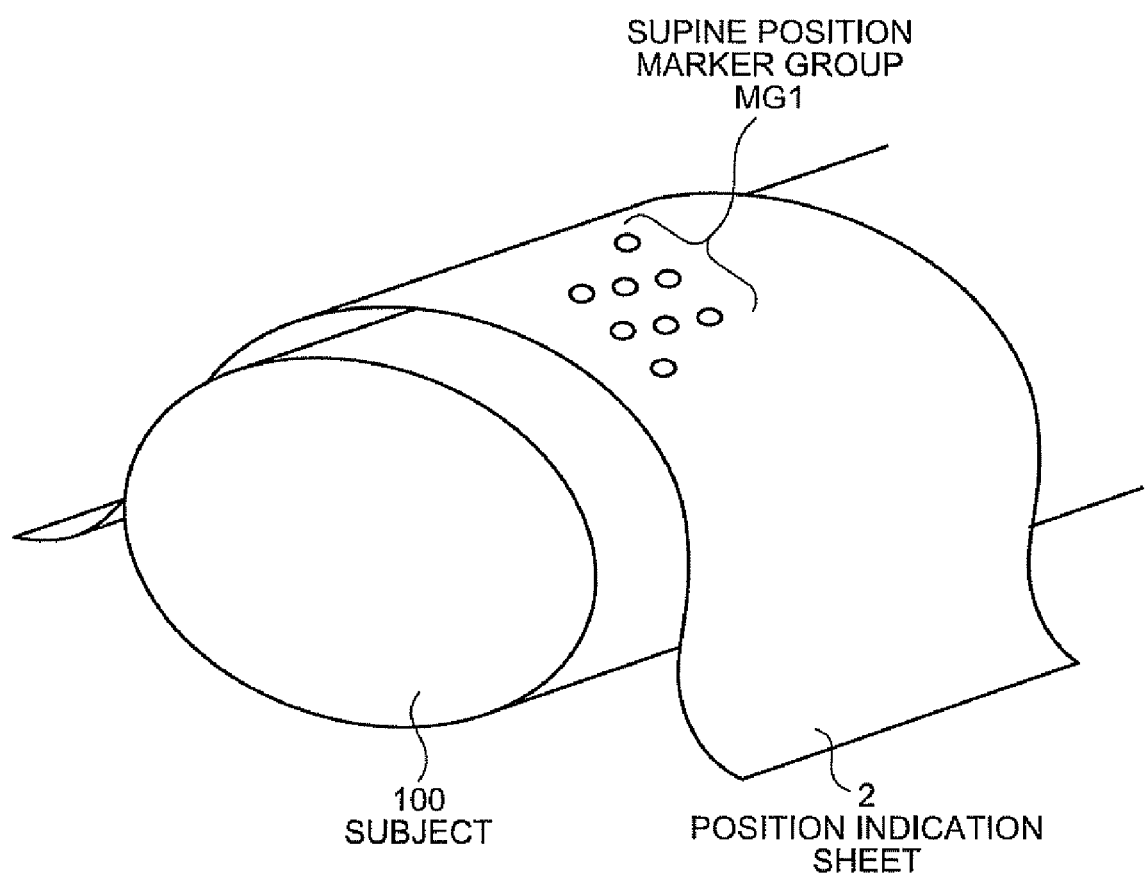
FIG. 29 is a schematic diagram illustrating a hanging type position indication sheet.

In the first to fourth embodiments of the invention, a wrap type position indication sheet which is attached to the trunk of the subject by being winded on the trunk is illustrated. However, the present invention is not limited to this position indication sheet, and position indication sheets of various types may be used. More specifically, a position indication sheet 2 representing the proximity positions may be a wearing position indication sheet which is formed like clothes as illustrated in FIG. 28 and worn by the subject 100. As illustrated in FIG. 29, the position indication sheet 2 may be a hanging type position indication sheet which is hanged on the trunk of the subject 100. The wearing or hanging type position indication sheet 2, like the wrap type position indication sheet, can represent proximity positions by the markers of the supine position marker group MG1.

Figure 30:
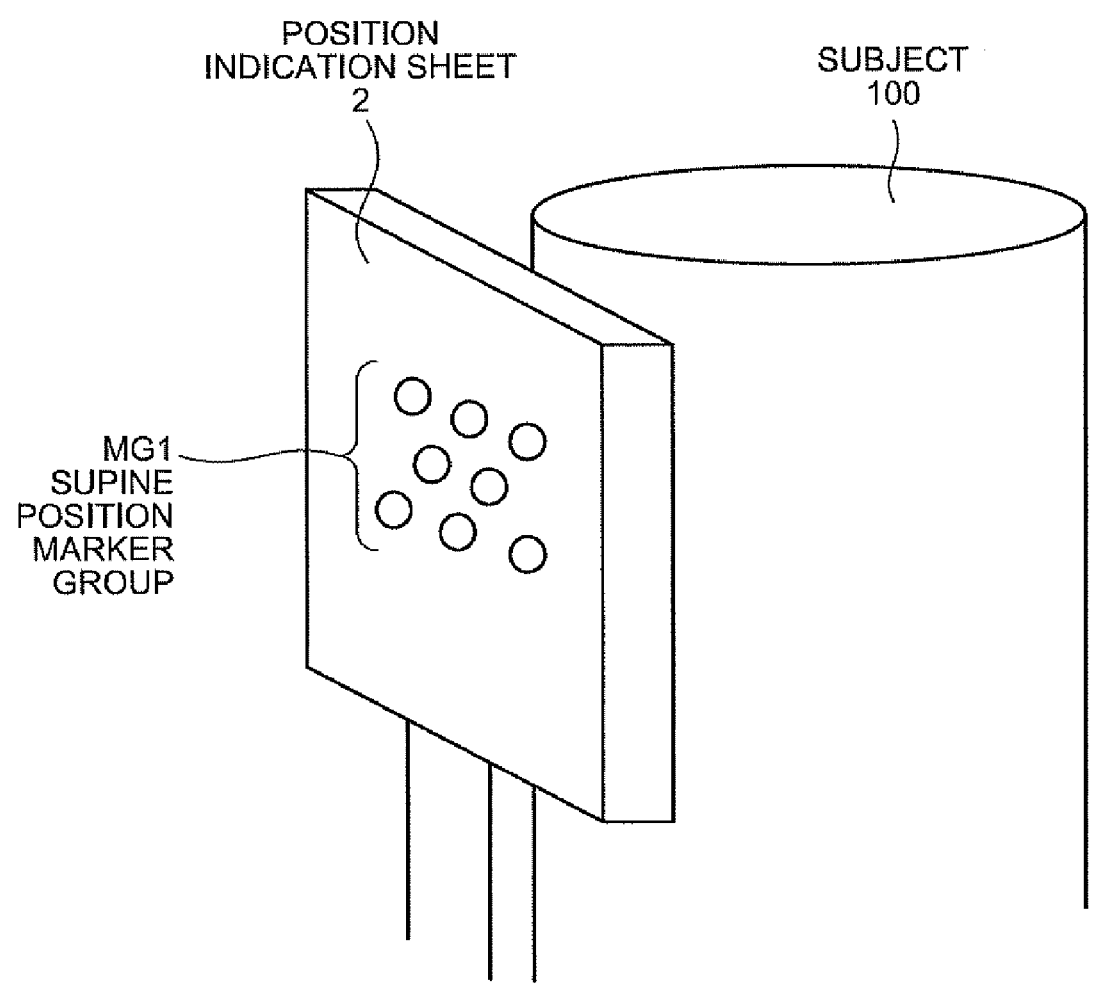
FIG. 30 is a schematic diagram illustrating a planer position indication sheet.
Figure 31:
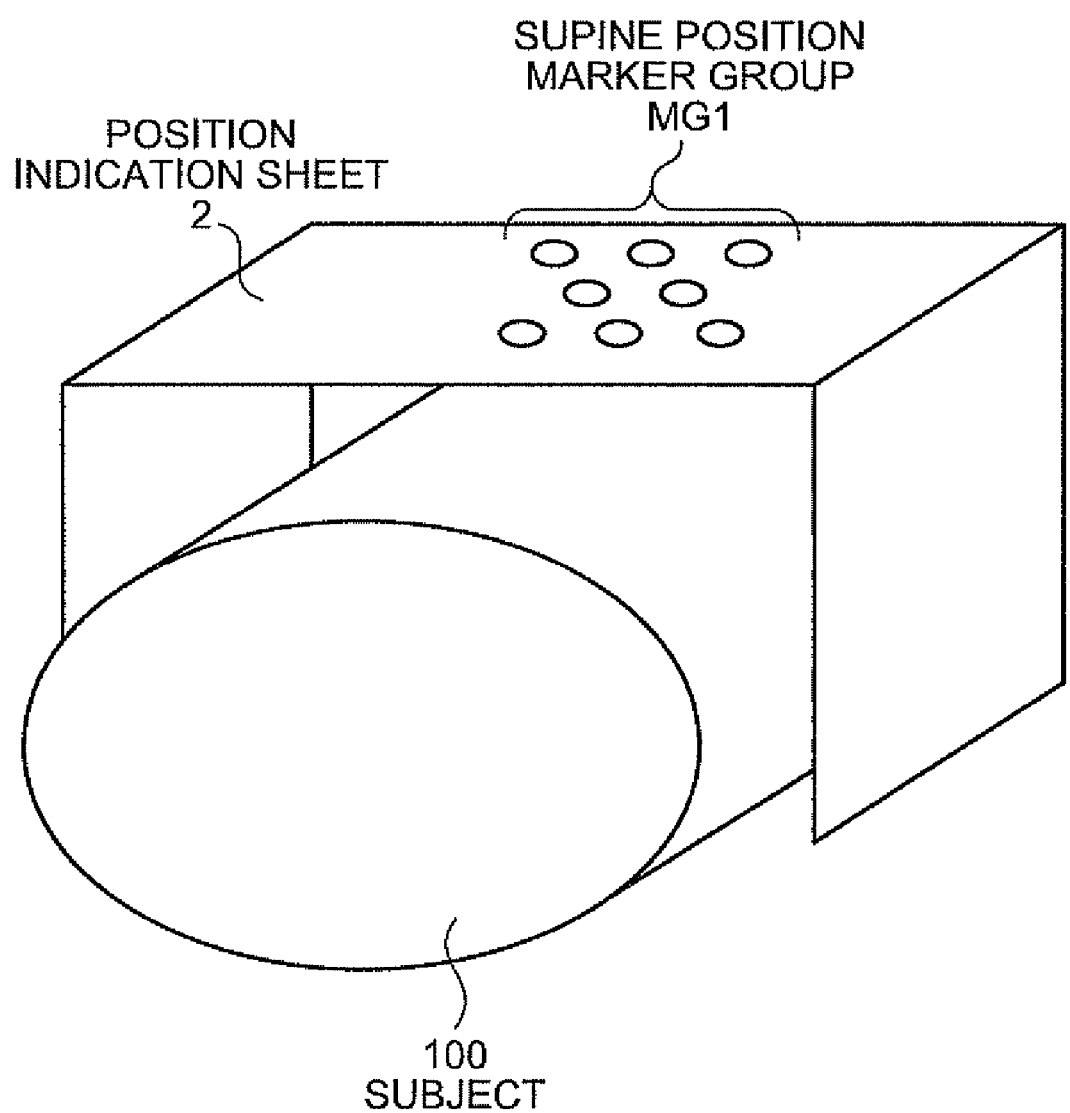
FIG. 31 is a schematic diagram illustrating a frame type position indication sheet.

The position indication sheet 2, as illustrated in FIG. 30, may be a planar position indication sheet obtained by forming, for example, the supine position marker group MG1 or the like on a highly transparent plain plate consisting of a nearly transparent glass or resin, or, as shown in FIG. 31, a frame type position indication sheet obtained by forming a highly transparent plate member consisting of a nearly transparent glass or resin in the form of a frame and forming, for example, the supine position marker group MG1 on a surface of the plate member. In this case, an examiner looks at the subject 100 through the planar or frame type position indication sheet 2, and a permanent magnet or the like may be brought close to a position (i.e., a proximity position) where markers formed on the planar or frame-like position indication sheet 2 are projected on the subject 100.

A plurality of position indication sheets of various types such as the wrap type, wearing type, hanging type, planar, and frame type position indication sheets are prepared for body types of subjects (patients), respectively. One of the position indication sheets is desirably selected depending on a body type of a patent to be examined. The position indication sheet can appropriately represent a proximity position on the body surface of the patient. As a result, the insides of patients having different body types can be efficiently observed (examined).

Figure 32:
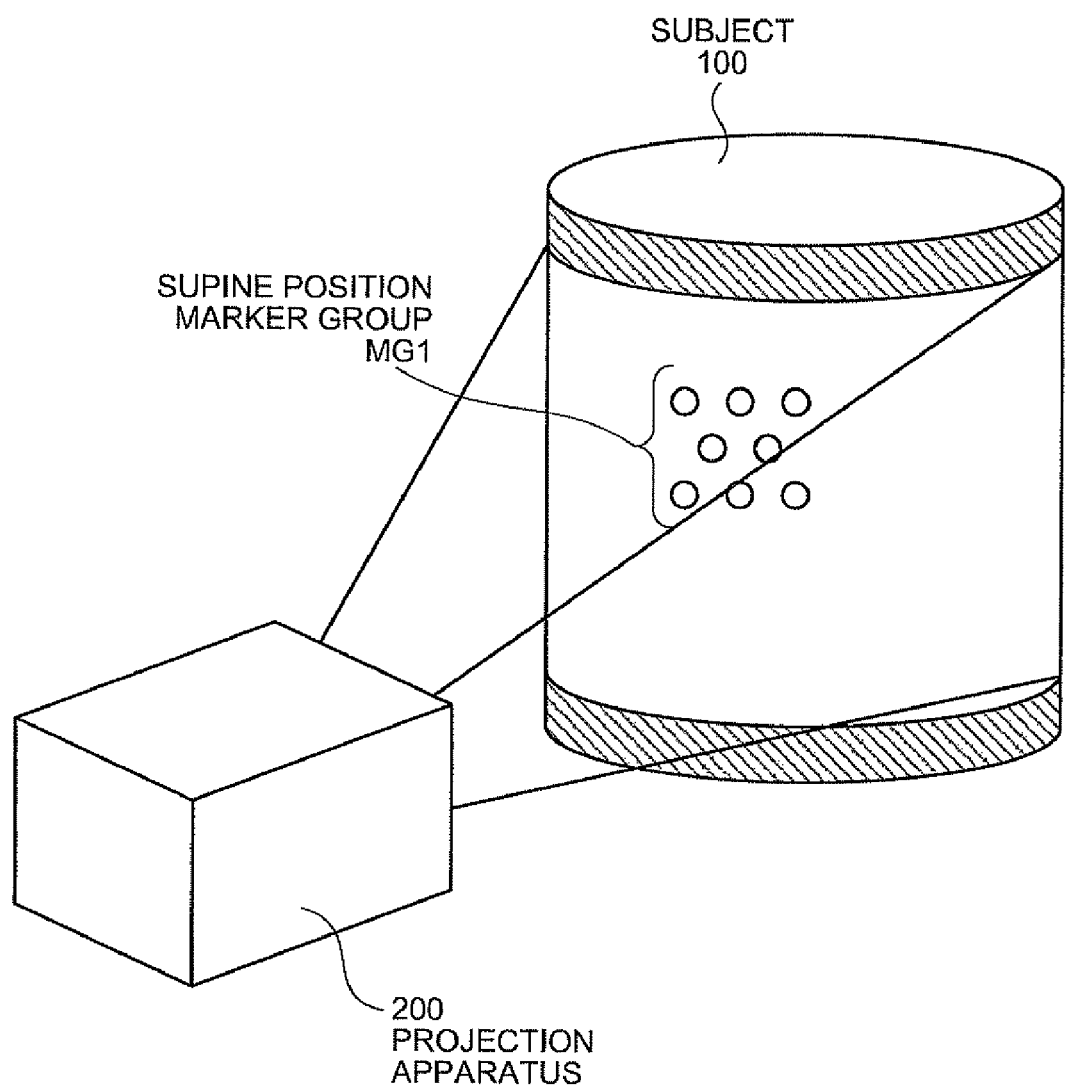
FIG. 32 is a schematic diagram illustrating a projection apparatus which projects information representing a proximity position on a subject.

Furthermore, in the first to fourth embodiments of the invention, a position indication sheet which is a sheet-like member is attached to a subject. However, the invention is not limited to this configuration, and information representing proximity positions such as markers may be projected on a subject. In this case, for example, as shown in FIG. 32, a body-insertable apparatus system including a projection apparatus 200 which projects the information representing the proximity positions in place of a position indication sheet may be structured. In this case, the projection apparatus 200 functions as a position display unit which displays the proximity positions, and the projection apparatus 200 projects, for example, the supine position marker group MG1 on the subject 100 to show proximity positions. The examiner may bring the permanent magnets close to the markers projected on the subject 100 by the projection apparatus 200.

The projection apparatus 200 may generate, on the basis of information of in-body images of subjects imaged by a CT, an MRI, or the like, projection information for projecting the in-body images of the bodies, and may project the in-body images on the subjects by using the projection information. In this case, the projection apparatus 200 can show a proximity position for a permanent magnet by the in-body image projected on the subject. As a result, information in the subject can be more correctly recognized, and a magnet which changes at least one of the position and an posture of the capsule endoscope in a gastrointestinal tract by a magnetism can be easily operated. Due to this operation, an image of a desired position in a gastrointestinal tract of a patient or the like can be easily picked by the capsule endoscope, and the subject can be appropriately diagnosed.

Figure 33:
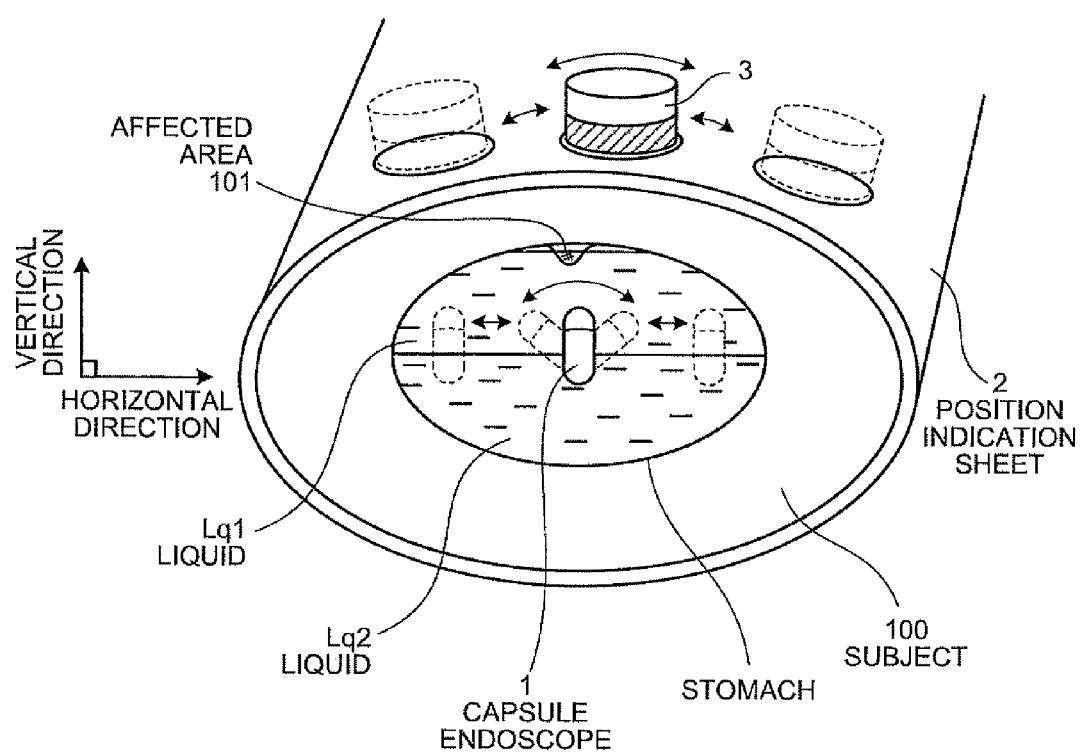
FIG. 33 is a schematic diagram illustrating a state in which a capsule endoscope is floated at the interface between two types of liquids inserted into a gastrointestinal tract.

In the first to fourth embodiments of the invention, a liquid Lq1 of one type is inserted into a gastrointestinal tract of a subject to float a capsule endoscope on the liquid Lq1. However, the invention is not limited to the configuration. Two types of liquids may be inserted into the gastrointestinal tract of the subject to float the capsule endoscope near an interface between the two types of liquids. In this case, the liquids Lq1 and Lq2 of two types to be inserted into the subject have specific gravities different from each other. More specifically, the liquid Lq1, as described above, has a specific gravity which is almost equal to or less than the specific gravity of the capsule endoscope 1, and the liquid Lq2 has a specific gravity larger than the specific gravity of the capsule endoscope 1. When the liquids Lq1 and Lq2 are inserted into the subject 100, for example, as shown in FIG. 33, the capsule endoscope 1 floats near the interface between the liquids Lq1 and Lq2 inside the stomach of the subject 100. The capsule endoscope 1 floating near the interface, as in the case of the first embodiment, changes at least one of the position and the posture by a magnetism of the permanent magnet 3 brought close to a proximity position.

Figure 34:
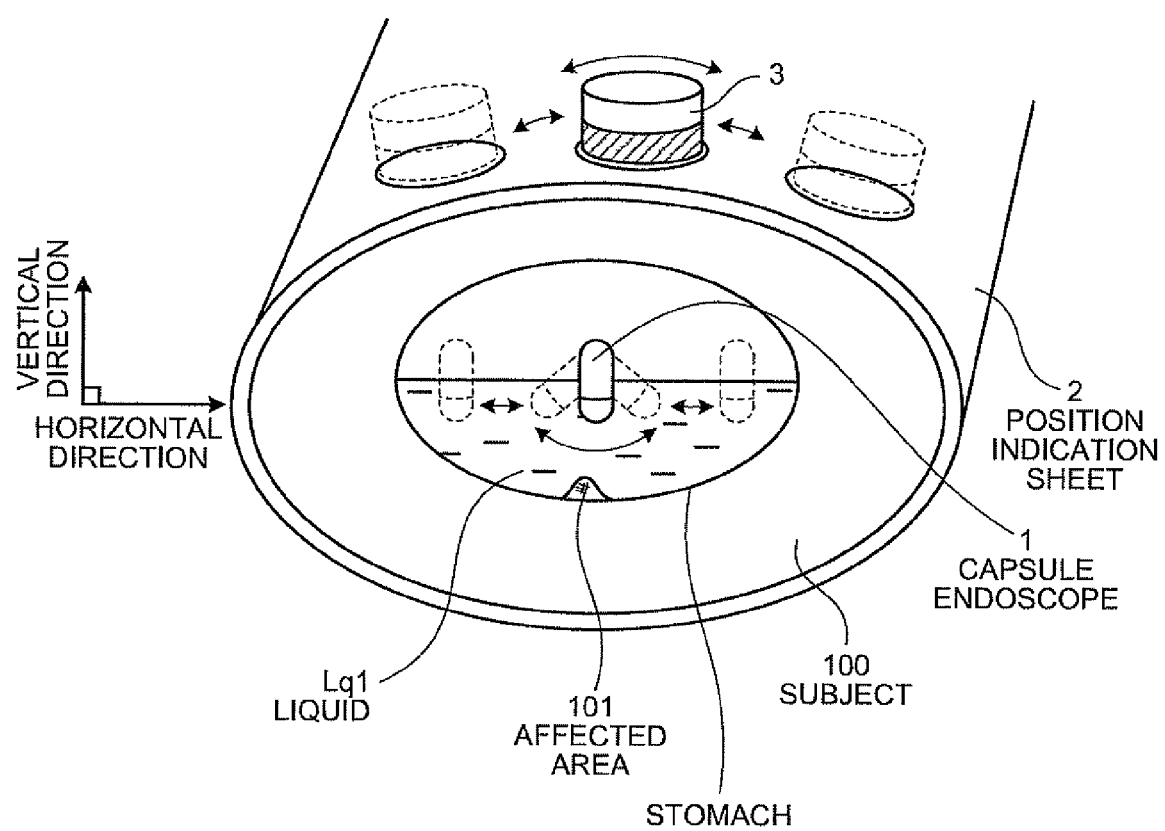
FIG. 34 is a schematic diagram illustrating a capsule endoscope having a center of gravity on a front-end side of a casing is inserted into the gastrointestinal tract.

Furthermore, in the first to fourth embodiments, the center of gravity of the capsule endoscope 1 is located on a rear-end side of the casing, and the capsule endoscope 1 floating on the liquid Lq1 in the gastrointestinal tract directs the imaging field of view on an upward side vertical to a liquid level of the liquid Lq1. However, the present invention is not limited to the configuration. The capsule endoscope 1 floating on the liquid Lq1 in the gastrointestinal tract may direct the imaging field of view on a downward side vertical to the liquid level of the liquid Lq1. In this case, the capsule endoscope 1 is structured to have a center of gravity on the front-end side of the casing. The capsule endoscope 1 structured as described above, as shown in FIG. 34, floats on the liquid Lq1 in the stomach of the subject 100, and directs the imaging field of view on the downward side vertical to the liquid level of the liquid Lq1. The capsule endoscope 1 which directs the imaging field of view on the vertically downward side can be changed in at least one of position and posture by the magnetic field of the permanent magnet 3 brought close to, for example, a proximity position. Since the capsule endoscope 1 can image the inside of the stomach stretched by the liquid Lq1 through the liquid Lq1, a detailed image of the inside of, for example, the stomach can be more photographically picked without stretching the biomedical tissue by the effervescent agent.

Figure 35:
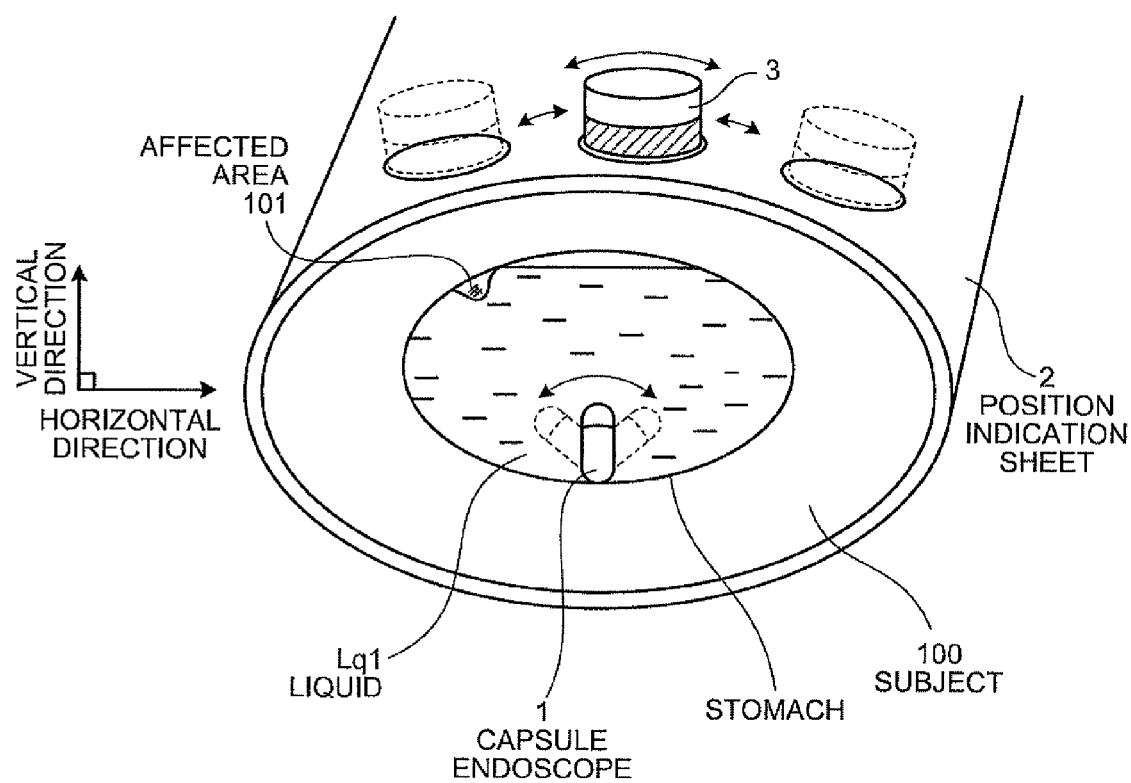
FIG. 35 is a schematic diagram illustrating a state in which a capsule endoscope having a specific gravity larger than that of a liquid in the gastrointestinal tract is inserted into the gastrointestinal tract.

In the first to fourth embodiments of the invention, the capsule endoscope is floated on a liquid inserted into a gastrointestinal tract of a subject. However, the invention is not limited to this configuration. The capsule endoscope may be sunk in a liquid inserted into the gastrointestinal tract of the subject. More specifically, for example, the capsule endoscope 1 is structured to have a specific gravity larger than that of the liquid Lq1 by adding a weight or the like or reducing an internal space to increase the density. In this case, the position of the center of gravity of the capsule endoscope 1 is kept on the rear-end side of the casing. The capsule endoscope 1 structured as described above, for example, as shown in FIG. 35, sinks down on the bottom of the liquid Lq1 in the stomach of the subject 100 and directs an imaging field of view on an upward side vertical to the liquid level of the liquid Lq1. The capsule endoscope 1 which directs the imaging filed on the vertically upward side can be changed in at least one of position and posture by the magnetism of the permanent magnet 3 brought close to, for example, a proximity position. Since the capsule endoscope 1 can image the inside of the stomach stretched by the liquid Lq1 through the liquid Lq1, for example, a detailed image of the inside of the stomach can be more clearly picked without stretching the biomedical tissue by the effervescent agent. Although not shown, in place of stretching of the stomach by the liquid Lq1, the stomach may be stretched by using the effervescent agent and small amount of water. In this case, since the stomach can be stretched by using a small amount of effervescent agent and small amount of water, a high ingestion rate can be achieved. In FIG. 35, the direction of the capsule endoscope 1 is changed by changing the position of the permanent magnet 3. However, the invention is not limited to this configuration, and the direction of the capsule endoscope 1 by changing the direction of the permanent magnet 3 without changing the position of the permanent magnet 3. At this time, the direction of the permanent magnet 3 can be represented by a marker or the like on the position indication sheet 2. In this case, since the position of the permanent magnet need not be changed, the operationality is improved.

Furthermore, in the third and fourth embodiments of the invention, at least one of the position and the posture of the capsule endoscope in a gastrointestinal tract is changed by a magnetic field of a permanent magnet. However, the invention is not limited to this configuration. An electromagnet may be brought close to a proximity position in place of the permanent magnet to change at least one of the position and the posture of the capsule endoscope in the gastrointestinal tract by the magnetic field of the electromagnet. In this case, the body-insertable apparatus system may be configured by a combination of the second and third embodiments or the second and fourth embodiments described above.

In the first to fourth embodiments of the invention, an image signal from the capsule endoscope is directly received by the workstation through the antenna connected to the workstation. However, the invention is not limited to this configuration. A predetermined receiving device which receives and accumulates an image signal from the capsule endoscope through an antenna arranged on a body surface of a subject may be used, and the image signal accumulated in the receiving device may be acquired by the workstation. In this case, an exchange of information between the receiving device and the workstation may be performed by using, for example, a portable recording medium.

Furthermore, in the first to fourth embodiments, the acceleration sensor and the angular velocity sensor are used as a unit which detects the position and the posture of the capsule endoscope inserted into a subject. However, the invention is not limited to this configuration. More specifically, as the unit which detects the position and the posture of the capsule endoscope, a unit which detects the position and the posture of the capsule endoscope in the gastrointestinal tract on the basis of a tomogram of the subject acquired by ultrasonic scanning may be used, or a unit which transmits a sonic wave from a predetermined position to the capsule endoscope in the subject to detect the position and the posture of the capsule endoscope in the gastrointestinal tract on the basis of the strength of the sonic wave detected by the capsule endoscope may be used. A magnetic field may be generated from the outside of the subject to the capsule endoscope in the subject, and the position and the posture of the capsule endoscope in the gastrointestinal tract may be detected on the basis of the magnetic field strength detected by the capsule endoscope. A magnetic field output from the capsule endoscope in the subject may be detected, and the position and the posture of the capsule endoscope in the gastrointestinal tract may be detected on the strength of the magnetic field.

In the first to fourth embodiments of the invention, the position of the capsule endoscope is detected by using the acceleration sensor, and the posture (direction of the major axis C1) of the capsule endoscope is detected by using the angle velocity sensor. However, the invention is not limited to this configuration. The position and the posture of the capsule endoscope may be magnetically detected by using an oscillating coil which oscillates an AC magnetic field.

Figure 36:
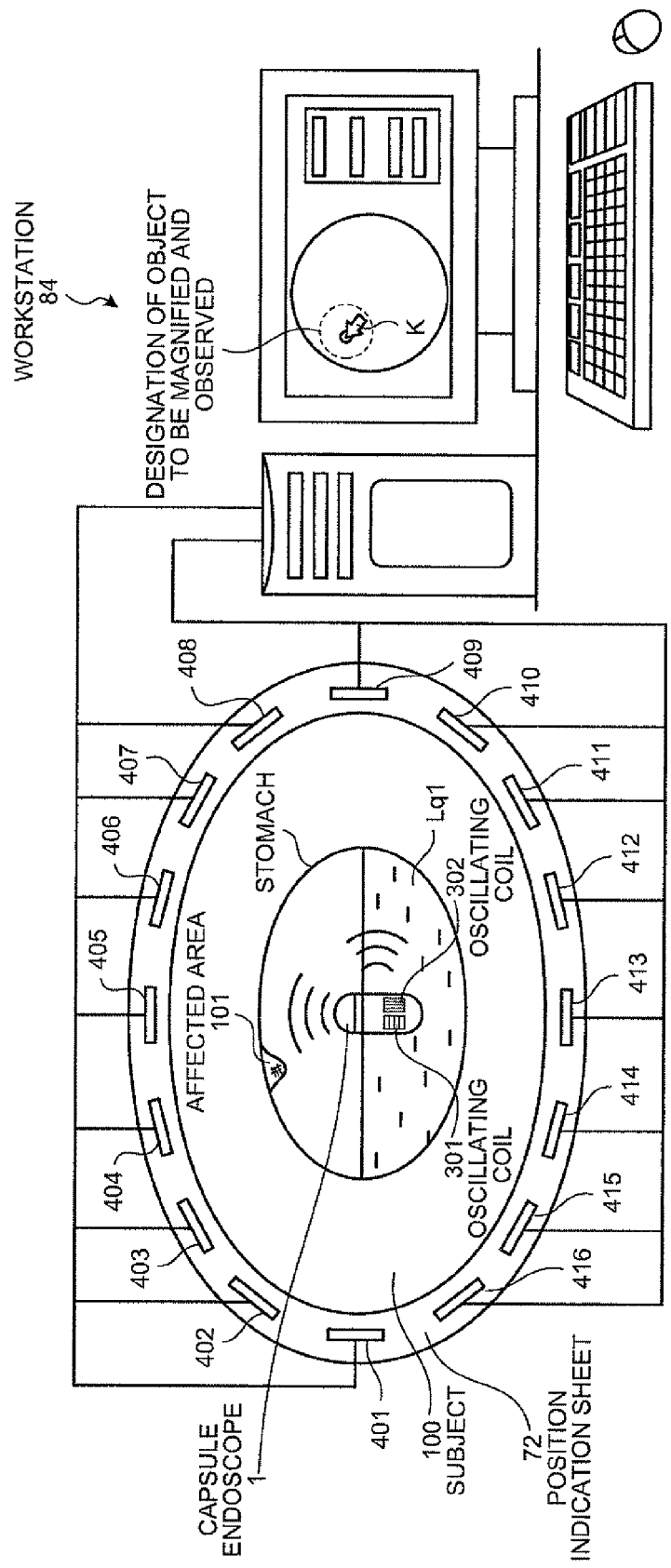
FIG. 36 is a schematic diagram showing one configuration of a body-insertable apparatus system according to a modification of the fourth embodiment of the invention.

For example, a modification of the body-insertable apparatus system according to the fourth embodiment described above, as shown in FIG. 36, includes a capsule endoscope 1 having two oscillating coils 301 and 302 which oscillate an AC magnetic field in a direction orthogonal to the outside of the body, a plurality of detection coils 401 to 416 which detect AC magnetic fields oscillated from the oscillating coils 301 and 302, a position indication sheet 72, and a workstation 84. The number of arranged detection coils may be two or more, and the number is not limited to 16. The detection coils 401 to 416 may be arranged inside the position indication sheet 72 as shown in FIG. 36. However, the detection coils 401 to 416 may be arranged outside the position indication sheet 72 and near the body surface of the subject 100.

The oscillating coil 301 generates an AC magnetic field in the direction of the major axis C1 on the basis of the control of the control unit 18 of the capsule endoscope 1. The oscillating coil 302 generates an AC magnetic field in a direction (for example, the direction of the radial axis C2a) perpendicular to the major axis C1 on the basis of the control of the control unit 18 of the capsule endoscope 1. On the other hand, the detection coils 401 to 416 are arranged inside, for example, the position indication sheet 72 and connected to the workstation 84 through a cable or the like. The detection coils 401 to 416 detect the AC magnetic fields oscillated by the oscillating coils 301 and 302 of the capsule endoscope 1 and output detection results to the workstation 84. The position/posture detector 89f of the workstation 84 calculates the positions and the directions of the oscillating coils 301 and 302 with respect to the position indication sheet 72 on the basis of the detection results of the AC magnetic fields (for example, current values corresponding to the strengths of the AC magnetic fields). On the basis of the calculation results, the position/posture detector 89f detects the position and the posture of the capsule endoscope 1 in the stomach of, for example, the subject 100.

Figure 37:
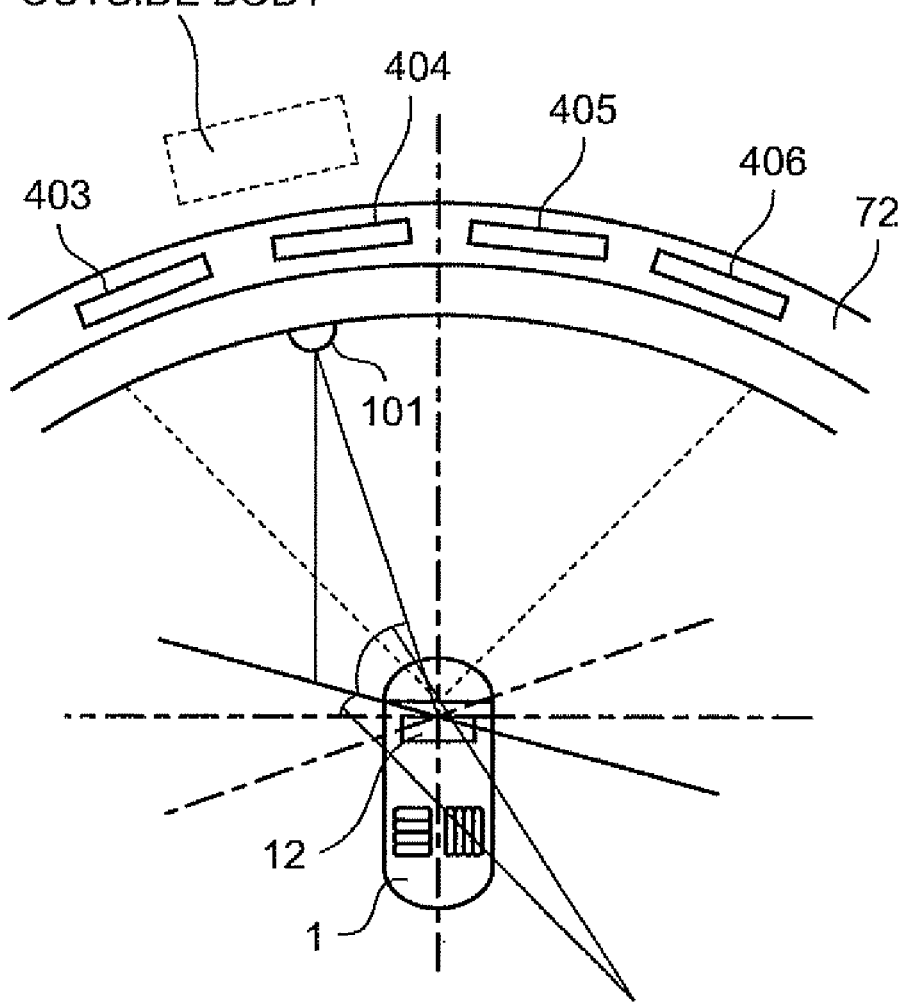
FIG. 37 is a schematic diagram illustrating a direction of a shortest distance for magnifying observation to an imaging device.

When the affected area 101 in the stomach is to be magnified and observed, an examiner matches the cursor K with a position (image position of the affected area 101) to be magnified and observed to select the position on the basis of an image displayed on the display unit 7 of the workstation 84. In this case, the input unit 6 inputs designated position information corresponding to the image position of the affected area 101 to the control unit 89. The position specifying unit 89h of the control unit 89 calculates a specific direction of the designated position (affected area 101) with respect to the imaging unit 12 of the capsule endoscope 1 based on the input designated position information and image. In this case, the position specifying unit 89h, as shown in FIG. 37, calculates a direction (direction of the shortest distance for magnifying observation to the imaging device) in which a distance between the imaging unit 12 of the capsule endoscope 1 and the affected area 101 is shortest. The position specifying unit 89h calculates a proximity position of the permanent magnet 3 to be brought close to the upper side of the position indication sheet 72 on the basis of the positions and the directions (i.e., the position and the posture of the capsule endoscope 1) of the oscillating coils 301 and 302 detected by the position/posture detector 89f, the positional relationships between the oscillating coils 301 and 302 and the imaging unit 12, and the direction of the shortest distance for magnifying observation to the imaging device, and the position specifying unit 89h specifies the proximity position corresponding to the affected area 101 in the proximity positions on the position indication sheet 72.

In the first to fourth embodiments of the invention, a permanent magnet is brought close to the inside of the casing of the capsule endoscope. However, the invention is not limited to this configuration. In order to control at least one of the position and the posture of the capsule endoscope by a magnetic field, a magnetic body may be present in the casing of the capsule endoscope. The magnetic member may be a ferromagnetic body, an electric component such as a battery, or an electromagnet.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A housing apparatus comprising:
a plurality of housing units in which a plurality of permanent magnets are housed, respectively;
a plurality of binding units which are arranged in the plurality of housing units, respectively, and bind the plurality of permanent magnets in the plurality of housing units, respectively;
a plurality of permanent magnet detectors which are arranged in the plurality of housing units, respectively, and detect whether the plurality of permanent magnets are housed in the plurality of housing units, respectively; and
a control unit which controls the plurality of binding units to selectively keep the plurality of permanent magnets in a binding state or a nonbinding state on the basis of detection results of the plurality of permanent magnet detectors.

2. The housing apparatus according to claim 1, wherein when some of the plurality of permanent magnet detectors detects the permanent magnet, the control unit controls the binding unit to bind the permanent magnet housed in the housing unit.

3. The housing apparatus according to claim 2, wherein when the detection result of some of the plurality of permanent magnet detectors changes from a detection result representing that the permanent magnet in the housing unit is not detected into a detection result representing that the permanent magnet in the housing unit is detected, the control unit controls the binding unit to bind the permanent magnet housed in the housing unit.

4. The housing apparatus according to claim 1, wherein when the plurality of permanent magnet detectors detect the plurality of permanent magnets in the housing units, the control unit controls the plurality of binding units to cancel a binding state of at least one of the plurality of permanent magnets bound in the plurality of housing units.

5. The housing apparatus according to claim 4, further comprising:
a permanent magnet selector which selects any one of the plurality of permanent magnets housed in the plurality of housing units, wherein
the control unit controls the plurality of binding units to cancel a binding state of the permanent magnet selected by the permanent magnet selector.

6. The housing apparatus according to claim 1, wherein the plurality of binding units are a plurality of adsorptive power generators which change adsorptive powers which adsorb the plurality of permanent magnets, respectively.

7. The housing apparatus according to claim 6, wherein each of the plurality of adsorptive power generators includes
a ferromagnetic body which adsorbs the permanent magnet in the housing unit; and
a distance changing unit which changes a distance between the permanent magnet in the housing unit and the ferromagnetic material.

8. The housing apparatus according to claim 6, wherein each of the plurality of adsorptive power generators is an electromagnet which adsorbs the permanent magnet in the housing unit.

9. The housing apparatus according to claim 1, wherein the plurality of binding units are a plurality of fixing units which mechanically fix the plurality of permanent magnets in the plurality of housing units.

10. The housing apparatus according to claim 1, wherein each of the plurality of housing units is a housing unit on which an opening from or into which the permanent magnet is inserted or pulled is formed, and
the plurality of binding units are a plurality of lids which openably close the openings of the plurality of housing units.

11. The housing apparatus according to claim 1, wherein each of the plurality of housing units includes a lid which openably closes the opening near the opening from or into which the permanent magnet is pulled or inserted, and
the plurality of binding units are a plurality of lock units which lock the plurality of lids, respectively.

12. The housing apparatus according to claim 11, wherein each of the plurality of housing units includes an opening/closing state detector which detects an opening/closing state of the lid, and
the control unit controls the plurality of lock units on the basis of detection results of the plurality of opening/closing detectors.

13. The housing apparatus according to claim 12, wherein when the plurality of permanent magnet detectors detect the plurality of permanent magnets in the housing units, respectively, and when the plurality of opening/closing state detectors detect closing states of the plurality of lids, the control unit controls the plurality of lock units to a locking state.

14. The housing apparatus according to claim 13, wherein when the plurality of permanent magnet detectors detect the plurality of permanent magnets in the plurality of housing units, and when detection results of the plurality of opening/closing state detectors are changed from detection results of the opening states of the lids into detection results of the closing states of the lids, the control unit controls the plurality of lock units in locking states.

15. The housing apparatus according to claim 12, wherein when the plurality of permanent magnet detectors detect the plurality of permanent magnets in the housing units, respectively, and when the plurality of opening/closing state detectors detect closing states of the plurality of lids, the control unit controls the plurality of lock units to cancel a locking state of any one of the plurality of lock units.

16. The housing apparatus according to claim 11, further comprising:
a permanent magnet selector which selects any one of the plurality of permanent magnets housed in the plurality of housing units, wherein
the control unit controls the plurality of lock units to cancel a locking state of the lid which closes the opening of the housing unit which houses the permanent magnet selected by the permanent magnet selector.

17. The housing apparatus according to claim 1, further comprising a magnetic shield which reduces an amount of leakage of a magnetic field of the permanent magnet.

18. A method for housing permanent magnets, comprising:
individually binding a plurality of permanent magnets respectively housed in a plurality of housing units;
displaying information indicating at least one of the plurality of permanent magnets a binding state of which is to be canceled; and
canceling the binding state of the permanent magnet displayed.

\* \* \* \* \*